(12) United States Patent
Askari et al.

(10) Patent No.: US 9,149,560 B2
(45) Date of Patent: Oct. 6, 2015

(54) SOLID POLYGLYCOL-BASED BIOCOMPATIBLE PRE-FORMULATION

(71) Applicant: Medicus Biosciences LLC, San Jose, CA (US)

(72) Inventors: Syed H. Askari, San Jose, CA (US); Yeon S. Choi, Emeryville, CA (US); Paul YuJen Wan, Norco, CA (US)

(73) Assignee: Medicus Biosciences LLC, San Jose, CA (US)

( * ) Notice: Subject to any disclaimer, the term of this patent is extended or adjusted under 35 U.S.C. 154(b) by 0 days.

(21) Appl. No.: 14/618,804

(22) Filed: Feb. 10, 2015

(65) Prior Publication Data

US 2015/0190544 A1    Jul. 9, 2015

Related U.S. Application Data

(62) Division of application No. 14/212,457, filed on Mar. 14, 2014, now Pat. No. 8,987,339.

(60) Provisional application No. 61/785,477, filed on Mar. 14, 2013.

(51) Int. Cl.

| A61L 27/52 | (2006.01) |
| --- | --- |
| A61L 26/00 | (2006.01) |
| A61L 27/18 | (2006.01) |
| A61L 27/54 | (2006.01) |
| A61K 31/00 | (2006.01) |
| A61K 45/06 | (2006.01) |
| A61K 33/00 | (2006.01) |

(52) U.S. Cl.
CPC .............. *A61L 26/0019* (2013.01); *A61K 31/00* (2013.01); *A61K 33/00* (2013.01); *A61K 45/06* (2013.01); *A61L 26/008* (2013.01); *A61L 26/0066* (2013.01); *A61L 27/18* (2013.01); *A61L 27/52* (2013.01); *A61L 27/54* (2013.01); *A61L 2300/206* (2013.01); *A61L 2300/404* (2013.01); *A61L 2300/41* (2013.01); *A61L 2400/06* (2013.01)

(58) Field of Classification Search
CPC ... A61K 2300/00; A61K 33/00; A61K 31/00; A61K 45/06; A61K 49/0457; A61K 9/06; A61L 27/18; A61L 26/0019; A61L 26/008; C08L 71/02
See application file for complete search history.

(56) References Cited

U.S. PATENT DOCUMENTS

| 5,037,384 | A | 8/1991 | Chang et al. |
| --- | --- | --- | --- |
| 5,336,175 | A | 8/1994 | Mames |
| 5,858,345 | A | 1/1999 | Charles et al. |
| 5,874,500 | A | 2/1999 | Rhee et al. |
| 6,051,648 | A | 4/2000 | Rhee et al. |
| 6,135,118 | A | 10/2000 | Dailey |
| 6,149,931 | A | 11/2000 | Schwartz et al. |
| 6,153,211 | A | 11/2000 | Hubbell et al. |
| 6,180,687 | B1 | 1/2001 | Hammer et al. |
| 6,207,772 | B1 | 3/2001 | Hatsuda et al. |
| 6,312,725 | B1 | 11/2001 | Wallace et al. |
| 6,458,889 | B1 | 10/2002 | Trollsas et al. |
| 6,475,508 | B1 | 11/2002 | Schwartz et al. |
| 6,547,714 | B1 | 4/2003 | Dailey |
| 6,566,406 | B1 | 5/2003 | Pathak et al. |
| 6,605,294 | B2 | 8/2003 | Sawhney |
| 6,624,245 | B2 | 9/2003 | Wallace et al. |
| 6,632,457 | B1 | 10/2003 | Sawhney |
| 6,703,037 | B1 | 3/2004 | Hubbell et al. |
| 6,703,378 | B1 | 3/2004 | Kunzler et al. |
| 6,818,018 | B1 | 11/2004 | Sawhney |
| 7,009,343 | B2 | 3/2006 | Lim et al. |
| 7,255,874 | B1 | 8/2007 | Bobo et al. |
| 7,332,566 | B2 | 2/2008 | Pathak et al. |
| 7,553,810 | B2 | 6/2009 | Gong et al. |
| 7,592,418 | B2 | 9/2009 | Pathak et al. |
| 8,388,995 | B1 | 3/2013 | Ali et al. |
| 2001/0003126 | A1 | 6/2001 | Rhee et al. |
| 2001/0055615 | A1 | 12/2001 | Wallace et al. |
| 2002/0042473 | A1 | 4/2002 | Trollsas et al. |
| 2002/0106409 | A1 | 8/2002 | Sawhney et al. |
| 2002/0114775 | A1 | 8/2002 | Pathak |
| 2002/0165337 | A1 | 11/2002 | Wallace et al. |
| 2003/0195113 | A1 | 10/2003 | Nakamura et al. |

(Continued)

FOREIGN PATENT DOCUMENTS

| WO | WO-9722371 A1 | 6/1997 |
| --- | --- | --- |
| WO | WO-9903454 A1 | 1/1999 |

(Continued)

OTHER PUBLICATIONS

3M Company. 3M™ Vetbond™ Veterinary Tissue Adhesive. Material Safety Data Sheet, Jun. 1, 2009.

Abbott Animal Health. GLUture®, Information Brochure. Feb. 2009.

Baino. Towards an ideal biomaterial for vitreous replacement: Historical overview and future trends. Acta Biomaterialia 7:921-935 (2011).

Brandi et al. Biodegradable hydrogels for time-controlled release of tethered peptides or proteins. Biomacromolecules 11:496-504 (2010).

(Continued)

*Primary Examiner* — Anna Falkowitz

(74) *Attorney, Agent, or Firm* — Wilson Sonsini Goodrich & Rosati

(57) ABSTRACT

Provided herein are pre-formulations forming a biocompatible hydrogel polymer comprising at least one nucleophilic compound or monomer unit, at least one electrophilic compound or monomer unit, and optionally a therapeutic agent and/or viscosity enhancer. In some embodiments, the biocompatible hydrogel polymer covers a wound in a mammal and adheres to the surrounding skin tissue. In other embodiments, the hydrogel polymer is delivered into a joint space to treat joint disease or navicular disease.

20 Claims, 24 Drawing Sheets

(56) References Cited

U.S. PATENT DOCUMENTS

| | | |
|---|---|---|
| 2003/0223957 A1 | 12/2003 | Schwartz et al. |
| 2004/0009205 A1 | 1/2004 | Sawhney |
| 2004/0018228 A1 | 1/2004 | Fischell et al. |
| 2004/0023842 A1 | 2/2004 | Pathak et al. |
| 2004/0033264 A1 | 2/2004 | Sawhney |
| 2005/0027069 A1 | 2/2005 | Rhee et al. |
| 2005/0191277 A1 | 9/2005 | Fisher |
| 2005/0200295 A1 | 9/2005 | Lim et al. |
| 2005/0203333 A1 | 9/2005 | Dailey et al. |
| 2005/0255039 A1 | 11/2005 | Desai |
| 2005/0281802 A1 | 12/2005 | Gong et al. |
| 2005/0281883 A1 | 12/2005 | Daniloff et al. |
| 2006/0057208 A1 | 3/2006 | Holzer et al. |
| 2006/0065199 A1 | 3/2006 | Davis |
| 2006/0115457 A1 | 6/2006 | Hnojewyj |
| 2006/0147409 A1 | 7/2006 | Pathak et al. |
| 2006/0159771 A1 | 7/2006 | Kadrmas et al. |
| 2006/0222596 A1 | 10/2006 | Askari et al. |
| 2007/0110813 A1 | 5/2007 | Ingenito et al. |
| 2008/0095736 A1 | 4/2008 | Pathak et al. |
| 2008/0115787 A1 | 5/2008 | Ingenito |
| 2008/0214695 A1 | 9/2008 | Pathak et al. |
| 2008/0261884 A1 | 10/2008 | Tsai et al. |
| 2008/0279944 A1 | 11/2008 | Sawhney |
| 2008/0281352 A1 | 11/2008 | Ingenito et al. |
| 2009/0170811 A1 | 7/2009 | Garvey et al. |
| 2009/0196928 A1 | 8/2009 | Hnojewyj |
| 2009/0215923 A1 | 8/2009 | Carnahan et al. |
| 2013/0108711 A1 | 5/2013 | Askari et al. |
| 2013/0116341 A1 | 5/2013 | Askari et al. |
| 2014/0248231 A1 | 9/2014 | Askari et al. |
| 2014/0271528 A1 | 9/2014 | Askari et al. |
| 2014/0271767 A1 | 9/2014 | Askari et al. |
| 2014/0302051 A1 | 10/2014 | Askari et al. |

FOREIGN PATENT DOCUMENTS

| | | | |
|---|---|---|---|
| WO | WO-0110416 A1 | 2/2001 | |
| WO | WO-02053526 A1 | 7/2002 | |
| WO | WO-2004021983 A2 | 3/2004 | |
| WO | WO-2006030431 A2 | 3/2006 | |
| WO | WO-2008141059 A2 | 11/2008 | |
| WO | WO-2009123768 A2 | 10/2009 | |
| WO | WO-2009132153 A2 | 10/2009 | |
| WO | WO-2011057131 A1 | 5/2011 | |
| WO | WO-2011066291 A2 | 6/2011 | |
| WO | WO 2011/140517 * | 10/2011 | ............. A61K 49/04 |
| WO | WO-2011140517 A2 | 11/2011 | |
| WO | WO-2011140519 A2 | 11/2011 | |

OTHER PUBLICATIONS

Campbell et al. Evaluation of the PleuraSeal™ Lung Sealant System as a Thoracic Sealant in a Canine Lung Resection Model. Covidien (2007).

Creative PEGWorks. Multiarm PEG materials. PEG product Catalog. last updated Dec. 31, 2012.

Dango et al. Initial experience with a synthetic sealant PleuraSeal™ after pulmonary resections: a prospective study with retrospective case matched controls. Journal of Cardiothoracic Surgery 5:50-58 (2010).

EP1317998.3 Search Report dated Feb. 13, 2014.

Ethicon, Inc. Ethicon™ Dermabond Advanced™ Instructions for Use. Status Mar. 2011.

Jemyork Biotechnology. Multiarm PEG materials, web pages printed from www.jemyork.com/proshow.aspx?id=131 on Feb. 12, 2013.

JenKem Technology USA. Multi-arm PEG Derivatives, accessed Oct. 7, 2013 http://www.jenkemusa.com/Pages/MultiarmPEGs.aspx.

JenKem Technology USA. Multiarm PEG materials. PEG Products Catalog, 2011.

Lazzarin et al. Efficacy of Enfuvirtide in Patients Infected with Drug-Resistant HIV-1 in Europe and Australia. N. Engl. J. Med. 348(22):2186-2195 (2003).

Marcus et al. The skeletal Response to Teriparatide is Largely Independent of Age, Initial bone Mineral Density, and Prevalent Vertebral Fractures in Postmenopausal Women With Osteoporisis. J. Bone Miner. Res. 18:18-23 (2003).

NanoCS, Inc. Multiarm PEG Derivatives. web pages printed from http://www.nanocs.com/PEG/MAPEG.htm on Feb. 12, 2013.

Neer et al. Effect of Parathyroid Hormone (1-34) on Fractures and Bone Mineral Density in Postmenopausal Women with Osteoporosis. New Engl. J. Med. 344(19):1434-1441 (2001).

NeoMend, Inc. ProGEL®, Instructions for Use and Product Labeling. Jan. 4, 2012.

NOF Corporation. Drug Delivery Systems. Catalogue Ver. 13. Prepared Oct. 2011.

PCT/US2011/035640 International Search Report and Written Opinion dated Jan. 19, 2012.

PCT/US2011/035643 International Search Report and Written Opinion dated Jan. 19, 2012.

PCT/US2013/40619 International Search Report dated Sep. 27, 2013.

PCT/US2014/028622 International Search Report dated Jul. 7, 2014.

PCT/US2014/028798 International Search Report dated Aug. 26, 2014.

Preul et al. Application of a new hydrogel dural sealant that reduces epidural adhesion formation: evaluation in a large animal laminectomy model. J Neurosurg Spine 12:381-390 (2010).

U.S. Appl. No. 13/696,028 Office Action dated Dec. 31, 2013.
U.S. Appl. No. 13/696,028 Office Action dated Jun. 12, 2014.
U.S. Appl. No. 13/696,028 Office Action dated Nov. 7, 2014.
U.S. Appl. No. 13/696,032 Office Action dated Dec. 10, 2014.
U.S. Appl. No. 13/696,032 Office Action dated Jun. 12, 2014.
U.S. Appl. No. 13/696,032 Office Action dated Oct. 22, 2013.
U.S. Appl. No. 14/212,457 Office Action dated Jun. 9, 2014.
U.S. Appl. No. 14/213,520 Office Action dated Dec. 15, 2014.
U.S. Appl. No. 14/213,520 Office Action dated Jul. 3, 2014.
U.S. Appl. No. 14/273,408 Office Action dated Aug. 29, 2014.
U.S. Appl. No. 14/273,408 Office Action dated Nov. 18, 2014.

* cited by examiner

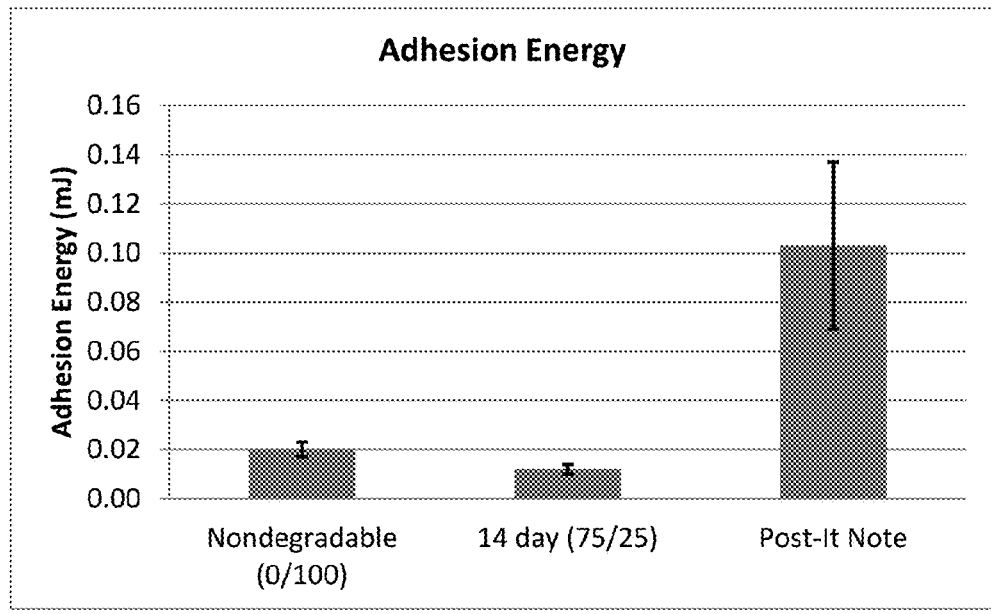
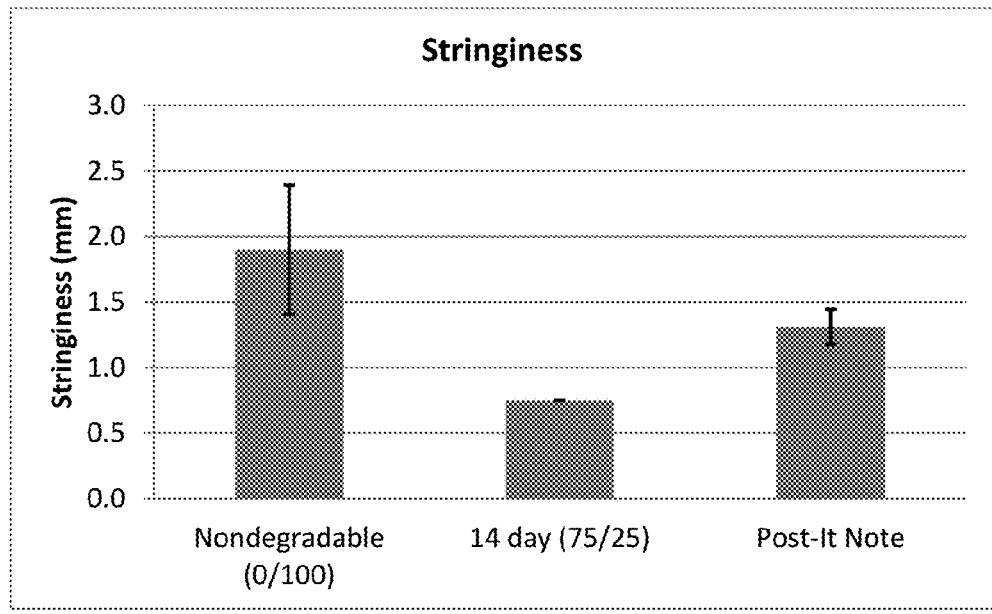

SOLID POLYGLYCOL-BASED BIOCOMPATIBLE PRE-FORMULATION

CROSS-REFERENCE

This application is a divisional of U.S. application Ser. No. 14/212,457, filed Mar. 14, 2014, and issued Mar. 24, 2015, as U.S. Pat. No. 8,987,339, which claims the benefit of and right of priority to U.S. Provisional Application No. 61/785,477, filed Mar. 14, 2013, the contents of which are hereby incorporated herein by reference in their entirety.

BACKGROUND OF THE INVENTION

During surgery in animals such as dogs, cats and horses etc. postsurgical and other wounds need to be sealed. Many commercially available bandages are scratched away or pulled off by animals and are dislodged from the location resulting in serious risk of infections. It is estimated that over 90% of the animals are back a second time after the surgery due to wound infection.

Animals also commonly develop arthritis in small "low motion" joints. These joints can cause a significant of pain causing lameness and owner distress. The most common treatment for this issue is an intra-articular joint injection of a corticosteroid.

Navicular disease is degeneration of the distal sesamoid bone in the horse. This disease causes millions of dollars lost in the equine community.

SUMMARY OF THE INVENTION

In one aspect, provided herein is a solid polyglycol-based, fully synthetic, pre-formulation, comprising at least one solid first compound comprising more than two nucleophilic groups; and at least one solid second compound comprising more than two electrophilic groups; wherein the solid polyglycol-based, fully synthetic, pre-formulation polymerizes and/or gels to form a polyglycol-based, fully synthetic, biocompatible hydrogel polymer in after addition of a liquid component. In some embodiments, the solid polyglycol-based, fully synthetic, pre-formulation, further comprises a solid buffer component. In some embodiments, the liquid component comprises water, saline, a buffer, a therapeutic agent or a combination thereof. In certain embodiments, the liquid component comprises water. In certain embodiments, the liquid component comprises saline. In certain embodiments, the liquid component comprises a buffer. In certain embodiments, the liquid component comprises a therapeutic agent. In some embodiments, the polyglycol-based, fully synthetic, biocompatible hydrogel polymer at least partially adheres to a target site.

In certain embodiments, the solid polyglycol-based, fully synthetic, pre-formulation further comprises a viscosity enhancer. In some embodiments, the viscosity enhancer is selected from hydroxyethylcellulose, hydroxypropylmethylcellulose, methylcellulose, polyvinyl alcohol, or polyvinylpyrrolidone.

In some embodiments, the nucleophilic group comprises a thiol or amino group. In certain embodiments, the nucleophilic group comprises an amino group. In some embodiments, the solid first compound is a polyol derivative. In some embodiments, solid first compound is a trimethylolpropane, diglycerol, pentaerythritol, sorbitol, hexaglycerol, tripentaerythritol, or polyglycerol derivative. In certain embodiments, the solid first compound is a trimethylolpropane, pentaerythritol, hexaglycerol, or tripentaerythritol derivative. In some embodiments, the solid first compound is a pentaerythritol or hexaglycerol derivative. In certain embodiments, the solid first compound is selected from the group consisting of ethoxylated pentaerythritol ethylamine ether, ethoxylated pentaerythritol propylamine ether, ethoxylated pentaerythritol amino acetate, ethoxylated hexaglycerol ethylamine ether, ethoxylated hexaglycerol propylamine ether, and ethoxylated hexaglycerol amino acetate. In some embodiments, the solid first compound is a MULTIARM (5k-50k) polyol derivative comprising polyglycol subunits and more than two nucleophilic groups. In some embodiments, MULTIARM is 3ARM, 4ARM, 6ARM, 8ARM, 10ARM, 12ARM. In some embodiments, MULTIARM is 4ARM or 8ARM. In some embodiments, the solid first compound is a MULTIARM-(5-50k)-SH, a MULTIARM-(5-50k)-NH2, a MULTIARM-(5-50k)-AA, or a combination thereof. In certain embodiments, the solid first compound is 4ARM-(5k-50k)-SH, 4ARM-(5k-50k)-NH2, 4ARM-(5k-50k)-AA, 8ARM-(5k-50k)-NH2, 8ARM-(5k-50k)-AA, or a combination thereof. In some embodiments, the solid first compound is 4ARM-5k-SH, 4ARM-2k-NH2, 4ARM-5k-NH2, 8ARM-20k-NH2, 4ARM-20k-AA, 8ARM-20k-AA, or a combination thereof.

In some embodiments, the solid first compound further comprises a solid second first compound comprising more than two nucleophilic groups. In some embodiments, the solid first compound further comprises a solid second first compound that is a MULTIARM-(5k-50k) polyol derivative comprising polyglycol subunits and more than two nucleophilic groups. In some embodiments, the solid second first compound is MULTIARM-(5-50k)-SH, MULTIARM-(5k-50k)-NH2, MULTIARM-(5k-50k)-AA. In some embodiments, the solid first compound is water soluble.

In certain embodiments, the electrophilic group is an epoxide, N-succinimidyl succinate, N-succinimidyl glutarate, N-succinimidyl succinamide or N-succinimidyl glutaramide. In some embodiments, the electrophilic group is N-succinimidyl glutaramide. In some embodiments, the solid second compound is a polyol derivative. In certain embodiments, the second compound is a trimethylolpropane, diglycerol, pentaerythritol, sorbitol, hexaglycerol, tripentaerythritol, or polyglycerol derivative. In some embodiments, the second compound is a trimethylolpropane, pentaerythritol, or hexaglycerol derivative. In certain embodiments, the solid second compound is selected from the group consisting of ethoxylated pentaerythritol succinimidyl succinate, ethoxylated pentaerythritol succinimidyl glutarate, ethoxylated pentaerythritol succinimidyl glutaramide, ethoxylated hexaglycerol succinimidyl succinate, ethoxylated hexaglycerol succinimidyl glutarate, and ethoxylated hexaglycerol succinimidyl glutaramide. In some embodiments, the solid second compound is a MULTIARM-(5k-50k) polyol derivative comprising polyglycol subunits and more than two electrophilic groups. In certain embodiments, the solid second compound is a MULTIARM-(5-50k)-SG, MULTIARM-(5-50k)-SGA, MULTIARM-(5-50k)-SS, MULTIARM-(5-50k)-SSA, or a combination thereof. In certain embodiments, the solid second compound is 4ARM-(5-50k)-SG, 4ARM-(5-50k)-SGA, 4ARM-(5-50k)-SS, 8ARM-(5-50k)-SG, 8ARM-(5-50k)-SGA, 8ARM-(5-50k)-SS, or a combination thereof. In some embodiments, the solid second compound is 4ARM-10k-SG, 8ARM-15k-SG, 4ARM-20k-SGA, 4ARM-10k-SS, or a combination thereof.

In some embodiments, the solid first compound is a MULTIARM-(5-50k)-SH, a MULTIARM-(5-50k)-NH2, a MULTIARM-(5-50k)-AA, or a combination thereof, and the solid second compound is a MULTIARM-(5-50k)-SG, a MULTIARM-(5-50k)-SGA, a MULTIARM-(5-50k)-SS, or a combination thereof. In other embodiments, the solid first compound is 4ARM-5k-SH, 4ARM-2k-NH2, 4ARM-5k-NH2, 8ARM-20k-NH2, 4ARM-20k-AA, 8ARM-20k-AA, or a combination thereof, and the solid second compound is 4ARM-10k-SG, 8ARM-15k-SG, 4ARM-20k-SGA, 4ARM-10k-SS, or a combination thereof. In certain embodiments, the solid first compound is 8ARM-20k-NH2 and/or 8ARM-20k-AA, and the solid second compound is 4ARM-20k-SGA. In some embodiments, the solid second compound is water soluble.

In some embodiments, the solid polyglycol-based, fully synthetic, pre-formulation gels at a predetermined time to form the polyglycol-based, fully synthetic, biocompatible hydrogel polymer. In certain embodiments, the polyglycol-based, fully synthetic, biocompatible hydrogel polymer is bioabsorbable. In some embodiments, the polyglycol-based, fully synthetic, biocompatible hydrogel polymer is bioabsorbed within about 1 to 70 days. In certain embodiments, the polyglycol-based, fully synthetic, biocompatible hydrogel polymer is substantially non-bioabsorbable.

In some embodiments, the solid polyglycol-based, fully synthetic, pre-formulation further comprises a radiopaque material or a pharmaceutically acceptable dye. In certain embodiments, the radiopaque material is selected from sodium iodide, barium sulfate, tantalum, Visipaque®, Omnipaque®, or Hypaque®, or combinations thereof.

In some embodiments, the solid polyglycol-based, fully synthetic, pre-formulation further comprises one or more therapeutic agents. In certain embodiments, the therapeutic agent is an antibacterial agent, an antifungal agent, an immunosuppressant agent, an anti-inflammatory agent, a bisphosphonate, gallium nitrate, stem cells, an antiseptic agent, or a lubricity agent. In some embodiments, the anti-inflammatory agent is a corticosteroid or a TNF-α inhibitor. In some embodiments, the anti-inflammatory agent is a corticosteroid. In certain embodiments, the corticosteroid is trimacinolone or methylprednisolone. In some embodiments, the therapeutic agent is an antiseptic agent. In certain embodiments, the antiseptic agent is chlorhexidine. In some embodiments, the therapeutic agent is a lubricity agent. In certain embodiments, the lubricity agent is hyaluronic acid. In some embodiments, the therapeutic agent is released from the polyglycol-based, fully synthetic, biocompatible hydrogel polymer through diffusion, osmosis, degradation of the polyglycol-based, fully synthetic, biocompatible hydrogel polymer, or any combination thereof. In certain embodiments, the therapeutic agent is initially released from the polyglycol-based, fully synthetic, biocompatible hydrogel polymer through diffusion and later released through degradation of the polyglycol-based, fully synthetic, biocompatible hydrogel polymer. In some embodiments, the therapeutic agent is substantially released from the polyglycol-based, fully synthetic, biocompatible hydrogel polymer within 180 days. In certain embodiments, the therapeutic agent is substantially released from the polyglycol-based, fully synthetic, biocompatible hydrogel polymer within 14 days. In some embodiments, the therapeutic agent is substantially released from the polyglycol-based, fully synthetic, biocompatible hydrogel polymer within 24 hours. In certain embodiments, the therapeutic agent is substantially released from the polyglycol-based, fully synthetic, biocompatible hydrogel polymer within one hour. In some embodiments, the first compound and the second compound do not react with the therapeutic agent during formation of the polyglycol-based, fully synthetic, biocompatible hydrogel polymer. In certain embodiments, the polyglycol-based, fully synthetic, biocompatible hydrogel polymer interacts with the therapeutic agent, and wherein more than 10% of the therapeutic agent is released through degradation of the polyglycol-based, fully synthetic, biocompatible hydrogel polymer. In some embodiments, more than 30% of the therapeutic agent is released through degradation of the polyglycol-based, fully synthetic, biocompatible hydrogel polymer. In certain embodiments, the polyglycol-based, fully synthetic, biocompatible hydrogel polymer interacts with the therapeutic agent by forming covalent bonds between the polyglycol-based, fully synthetic, biocompatible hydrogel polymer and the therapeutic agent. In some embodiments, the polyglycol-based, fully synthetic, biocompatible hydrogel polymer interacts with the therapeutic agent by forming a non-covalent bond between the polyglycol-based, fully synthetic, biocompatible hydrogel polymer and the therapeutic agent. In some embodiments, the therapeutic agent is released while the polyglycol-based, fully synthetic, biocompatible hydrogel polymer degrades. In certain embodiments, the release of the therapeutic agent is essentially inhibited until a time that the polyglycol-based, fully synthetic, biocompatible hydrogel polymer starts to degrade. In some embodiments, the time the polyglycol-based, fully synthetic, biocompatible hydrogel polymer starts to degrade is longer the higher a degree of cross-linking of the polyglycol-based, fully synthetic, biocompatible hydrogel polymer. In certain embodiments, the time the polyglycol-based, fully synthetic, biocompatible hydrogel polymer starts to degrade is shorter the higher a concentration of ester groups in the first or second compound.

In one aspect, provided herein is a method of treating wounds of a mammal by delivering a liquid polyglycol-based, fully synthetic, biocompatible formulation formed by adding a liquid component to the solid polyglycol-based, fully synthetic, pre-formulation to a target site of the wound of the mammal, wherein the liquid polyglycol-based, fully synthetic, biocompatible formulation gels at the target site of the wound to form a polyglycol-based, fully synthetic, biocompatible hydrogel polymer. In another aspect, provided herein, is a method of treating arthritis in a mammal by delivering a liquid polyglycol-based, fully synthetic, biocompatible formulation formed by adding a liquid component to the solid polyglycol-based, fully synthetic, pre-formulation into a target site in a joint space, wherein the liquid polyglycol-based, fully synthetic, biocompatible formulation gels at the target site in the joint space to form a polyglycol-based, fully synthetic, biocompatible hydrogel polymer. In a further aspect, provided herein is a method of treating navicular disease in a horse by delivering a liquid polyglycol-based, fully synthetic, biocompatible formulation formed by adding a liquid component to the solid polyglycol-based, fully synthetic, pre-formulation to a target site in a hoof of the horse, wherein the liquid polyglycol-based, fully synthetic, biocompatible formulation gels at the target site in the hoof of the horse to form a polyglycol-based, fully synthetic, biocompatible hydrogel polymer. In certain embodiments of methods described herein, the polyglycol-based, fully synthetic, biocompatible hydrogel polymer closes the wound. In some embodiments, the polyglycol-based, fully synthetic, biocompatible hydrogel polymer covers the wound and adheres to surrounding skin. In some embodiments, the mammal is a human. In certain embodiments, the mammal is an animal. In some embodiments, the animal is a dog, cat, cow, pig, or horse.

In some embodiments, the polyglycol-based, fully synthetic, biocompatible hydrogel polymer of the synthetic, pre-formulation as described herein.

In another aspect, provided herein is a polyglycol-based, fully synthetic, biocompatible polymer, is formed by contacting a solid polyglycol-based, fully synthetic, pre-formulation with a liquid component, comprising at least one solid first compound comprising more than two nucleophilic groups; and at least one solid second compound comprising more than two electrophilic groups. In some embodiments, the solid polyglycol-based, fully synthetic, pre-formulation further comprises a solid buffer component. In some embodiments, the polyglycol-based, fully synthetic, pre-formulation further comprises a therapeutic agent. In certain embodiments, the liquid component comprises water, saline, a buffer, a therapeutic agent or a combination thereof. In some embodiments, the liquid component comprises water. In other embodiments, the liquid component comprises saline. In some embodiments, the liquid component comprises a buffer. In certain embodiments, the liquid component comprises a therapeutic agent. In some embodiments, the liquid component comprises of water. In some embodiments, the polyglycol-based, fully synthetic solid pre-formulation further comprises a viscosity enhancer. In some embodiments, the polyglycol-based fully synthetic, pre-formulation further comprises a therapeutic agent.

In another aspect, described herein is a solid pre-formulation, comprising at least one solid first compound comprising more than two nucleophilic groups; and at least one solid second compound comprising more than two electrophilic groups; wherein the pre-formulation polymerizes and/or gels form a biocompatible hydrogel polymer in the presence of a liquid component. In some embodiments, the solid pre-formulation further comprises a solid buffer component. In certain embodiments, the liquid component comprises water, saline, a buffer, a therapeutic agent or a combination thereof. In some embodiments, the liquid component comprises water. In certain embodiments, the liquid component comprises saline. In some embodiments, the liquid component comprises a buffer. In some embodiments, the liquid component comprises a therapeutic agent. In certain embodiments, the hydrogel polymer at least partially adheres to a target site. In some embodiments, the solid pre-formulation further comprises a viscosity enhancer. In certain embodiments, the viscosity enhancer is selected from hydroxyethylcellulose, hydroxypropylmethylcellulose, methylcellulose, polyvinyl alcohol, or polyvinylpyrrolidone In certain embodiments, the solid pre-formulation further comprises a therapeutic agent. In some embodiments, the therapeutic agent is an antibacterial agent, an antifungal agent, an immunosuppressant agent, an anti-inflammatory agent, a bisphosphonate, gallium nitrate, stem cells, an antiseptic agent, or a lubricity agent. In certain embodiments, anti-inflammatory is s a corticosteroid or a TNF-α inhibitor. In some embodiments, the therapeutic agent is an antiseptic agent.

In some embodiments, the solid pre-formulation is polyglycol-based. In other embodiments, the solid pre-formulation is fully synthetic. In certain embodiments, the solid pre-formulation is PEG-based. In some embodiments, the solid pre-formulation is fully synthetic and polyglycol based. In other embodiments, the solid pre-formulation is fully synthetic and PEG-based.

In another aspect described herein is a solid biocompatible hydrogel polymer, comprising at least one solid first monomeric unit bound through at least one amide, thioester, or thioether linkage to at least one solid second monomeric unit; and at least one solid second monomeric unit bound to at least one solid first monomeric unit; wherein biocompatible hydrogel polymer is formed from contacting a solid pre-formulation with a liquid component. In some embodiments, the liquid component comprises water, saline solution, therapeutic agent, or a combination thereof. In certain embodiments, the liquid component comprises water. In some embodiments, the liquid component comprises a saline solution. In certain embodiments, the liquid component comprises a therapeutic agent. In some embodiments, the solid first monomeric unit is a polyol derivative. In certain embodiments, the solid first monomeric unit is a glycol, trimethylolpropane, pentaerythritol, hexaglycerol, or tripentaerythritol derivative. In some embodiments, the solid first monomeric unit further comprises one or more polyethylene glycol sections. In certain embodiments, the solid first monomeric unit is a pentaerythritol or hexaglycerol derivative. In some embodiments, the solid second monomeric unit is a polyol derivative. In certain embodiments, the solid second monomeric unit is a trimethylolpropane, glycerol, diglycerol, pentaerythritol, sorbitol, hexaglycerol, tripentaerythritol, or polyglycerol derivative. In some embodiments, the solid second monomeric further comprises one or more polyethylene glycol sections. In certain embodiments, the solid second monomeric unit is a trimethylolpropane, pentaerythritol, or hexaglycerol derivative.

In another aspect described herein is a biocompatible hydrogel polymer, comprising: at least one solid first monomeric unit bound through at least one amide linkage to at least one solid second monomeric unit; and at least one solid second monomeric unit bound to at least one solid first monomeric unit; wherein the biocompatible hydrogel polymer is formed from contacting a solid pre-formulation with a liquid component. In some embodiments, the liquid component comprises water, saline solution, saline solution, therapeutic agent, or combination thereof. In certain embodiments, the liquid component comprises water. In some embodiments, the liquid component comprises a saline solution. In certain embodiments, the liquid component comprises a therapeutic agent. In some embodiments, the solid first monomeric unit is a polyol derivative. In certain embodiments, the solid first monomeric unit is a glycol, trimethylolpropane, pentaerythritol, hexaglycerol, or tripentaerythritol derivative. In some embodiments, the solid first monomeric unit further comprises one or more polyethylene glycol sections. In certain embodiments, the solid first monomeric unit is a pentaerythritol or hexaglycerol derivative. In some embodiments, the solid second monomeric unit is a polyol derivative. In certain embodiments, the solid second monomeric unit is a trimethylolpropane, glycerol, diglycerol, pentaerythritol, sorbitol, hexaglycerol, tripentaerythritol, or polyglycerol derivative. In some embodiments, the solid second monomeric further comprises one or more polyethylene glycol sections. In certain embodiments, the solid second monomeric unit is a trimethylolpropane, pentaerythritol, or hexaglycerol derivative.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 10A-10D shows a comparison of the firmness (10A), tack (10B), adhesion energy (10C) and stringiness (10D) of the general polymer formulation: 8ARM-20k-AA/8ARM-20k-NH2 (x/y) & 4ARM-20k-SGA at 4.8% solution with 0.3% HPMC. The measured values for a Post-It™ note are included as a reference.

DETAILED DESCRIPTION OF THE INVENTION

Figure 1:
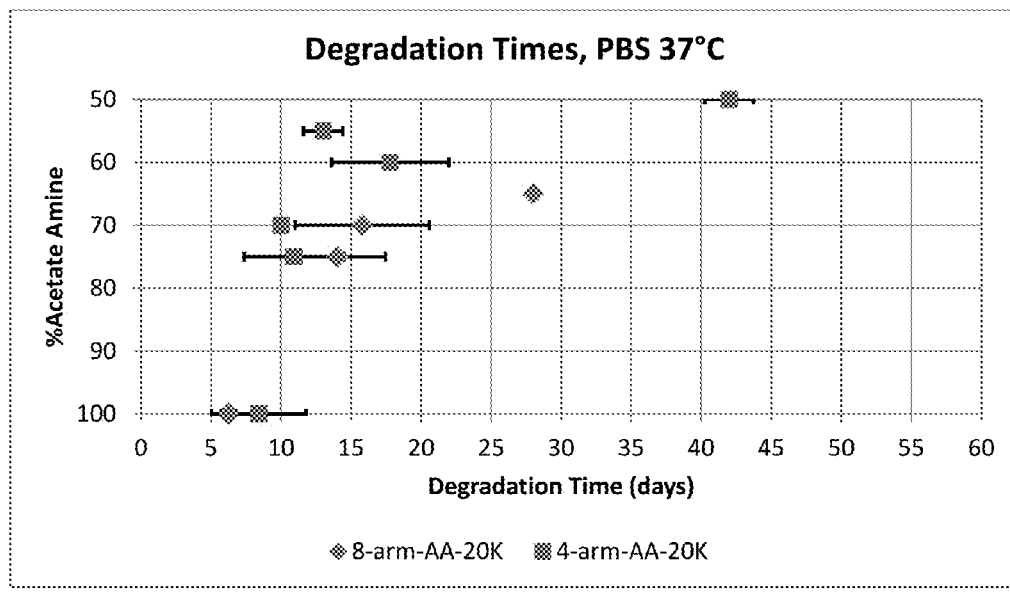
FIG. 1 shows the effect of addition of degradable acetate amine 8ARM-20k-AA or 4ARM-20k-AA on degradation times. Degradations occurred in phosphate buffered saline (PBS) at 37° C.

To help close the wounds and control infection, a cyanoacrylate based glue material is used. Even though the glue works effectively to seal the wounds, it is highly toxic and thus results in complications. Furthermore, doctors need an easily prepared and versatile formulation that can be easily adapted to different uses (external or internal) across a wide range of medical conditions, as well as optionally contain additional components like therapeutic agents or compounds that modify the physiochemical properties of the formulation.

Provided herein are solid non-toxic pre-formulations that form a biocompatible hydrogel polymer that is easily applied. The solid pre-formulation may be used to prepare and deliver a biocompatible hydrogel polymer to a target site. For instance, the target site may be a wound or a joint space. Once applied, e.g., sprayed over the wound, in the liquid form after addition of a liquid component to the solid pre-formulation, the liquid formulation gels quickly and forms a solid hydrogel polymer layer, for instance, over the wound or filling the joint space. The biocompatible hydrogel polymer seals the wound and it also sticks to the surrounding skin to form a suture. The biocompatible hydrogel polymer layer over the wound acts as a barrier to keep the wound from getting infected. In some instances, the biocompatible hydrogel polymer layer in contact with the skin makes the skin surface sticky and thus allows the bandage to stick to the skin more effectively. Most importantly, the biocompatible hydrogel polymer is non-toxic. After the wound healing has taken place, the biocompatible hydrogel polymer dissolves and is absorbed without producing toxic by-products. In certain embodiments, the wound is on a mammal. In some embodiments, the mammal is a human. In order embodiments, the mammal is an animal. In some embodiments, the animal is a dog, a cat, a cow, a pig, or a horse.

The solid pre-formulations presented herein are convenient, versatile, and adaptable, wherein the pre-formulation comprises a solid first compound and a solid second compound that only gel/polymerize to form the biocompatible hydrogel polymer after addition of a liquid component. Additionally, a buffer component, therapeutic agents, and viscosity enhancers may be added in solid form to the solid pre-formulation or may be present in the liquid component.

In some embodiments, the biocompatible hydrogel polymer is also loaded with one or more therapeutic agents, such as antibiotics. The physical and chemical nature of the biocompatible hydrogel polymer is such that a large variety of commonly available therapeutic agents can be with the pre-formulation that forms the biocompatible hydrogel polymer. In certain embodiments, the pre-formulation is applied to a wound without the therapeutic agent losing activity. In some embodiments, the therapeutic agent is an anti-infective agent, such as an aminoglycoside antibiotic, a fluoroquinolone, a macrolide antibiotic, an antifungal agent, or an antibacterial agent. In certain embodiments, the antibiotic is neomycin, bacitracin zinc or polymyxin B sulfates etc. In some embodiments, the therapeutic agent is an antibacterial agent. In certain embodiments, the therapeutic agent is an antiseptic agent, such as chlorhexidine. In other embodiments, the therapeutic agent is a lubricity agent. In specific embodiments, the lubricity agent is hyaluronic acid.

The amount of materials used for covering a wound depends on the size of the wound. Most common wounds may be about 1 $cm^2$ and up to as much as 30 $cm^2$. In certain embodiments, the biocompatible hydrogel polymer keeps the wound sealed for 24-48 hours and protects it from infection, which avoids repeat visits to the hospital and thus saving costs.

Furthermore, mammals commonly suffer from arthritis in small "low motion" joints. In both animals and humans, these arthritic joints may cause a significant amount of pain. In some instances, the arthritis causes lameness and owner distress. Provided herein, are pre-formulations that are delivered into the joint to form a biocompatible hydrogel polymer. In certain embodiments, the biocompatible hydrogel polymer acts as a "joint spacer" to decrease the amount of bone to bone pressure in these "low motion" joints. In some embodiments, the biocompatible hydrogel polymer is substantially non-absorbable. In certain embodiments, the amount of pre-formulation delivered into the joint space is about 4 mL. In some embodiments, the pre-formulation also comprises a therapeutic agent. In certain embodiments, the therapeutic agent is an antibiotic to prevent joint infection. In other embodiments, the therapeutic agent is an anti-inflammatory drug, such as an NSAID or a TNF-alpha inhibitor. In some embodiments, the therapeutic agent comprises bisphosphonates, corticosteroids, gallium nitrate or stem cells. In certain embodiments, the therapeutic agent is a corticosteroid. In some embodiments, the corticosteroid is trimacinolone or methylprednisolone. In other embodiments, the therapeutic agent comprises a lubricity agent. In specific embodiments, the lubricity agent is hyaluronic acid.

In addition, in horses Navicular disease is degeneration of the distal sesamoid bone, which causes millions of dollars lost in the equine community. Provided herein is a pre-formulation that forms a biocompatible hydrogel polymer that acts as a gel cushion between the deep digital flexor tendon and the navicular bone. In some embodiments, the biocompatible hydrogel polymer is substantially non-absorbable. In certain embodiments, the biocompatible hydrogel polymer bioabsorbs over time. In certain embodiments, the amount of pre-formulation delivered into the joint space is about 2-3 mL. In some embodiments, the pre-formulation also comprises a therapeutic agent. In certain embodiments, the therapeutic agent is an antibiotic to prevent joint infection. In other embodiments, the therapeutic agent is an anti-inflammatory drug, such as an NSAID or a TNF-alpha inhibitor. In some embodiments, the therapeutic agent comprises bisphosphonates, corticosteroids, gallium nitrate or stem cells. In certain embodiments, the therapeutic agent is a corticosteroid. In some embodiments, the corticosteroid is trimacinolone or methylprednisolone. In other embodiments, the therapeutic agent comprises a lubricity agent. In specific embodiments, the lubricity agent is hyaluronic acid.

In some instances, the therapeutic agent is released from the biocompatible hydrogel polymer over an extended period of time. In certain instances, delivery of the therapeutic agent in a biocompatible hydrogel polymer provides a depot of the therapeutic agent (e.g., under the skin), wherein the depot releases the therapeutic agent over an extended period of time (e.g., 1 day, 2 days, 3 days, 4 days, 5 days, 6 days, 7 days, 10, days, 14 days, 3 week, 4 week). In some instances, the biocompatible hydrogel polymer releases the therapeutic agent after a delay as a delayed burst.

Solid Pre-Formulations

The solid pre-formulation comprises at least one solid first compound comprising more than two nucleophilic groups and at least one solid second compound comprising more than two electrophilic groups. In some embodiments, the pre-formulation comprises two solid first compounds comprising more than two nucleophilic groups. In certain embodiments, the pre-formulation comprises two solid second compounds comprising more than two electrophilic groups. In some embodiments the pre-formulation comprises two solid first compounds comprising more than two nucleophilic groups and one solid second compound comprising more than two electrophilic groups. In certain embodiments the pre-formulation comprises one solid first compounds comprising more than two nucleophilic groups and two solid second compounds comprising more than two electrophilic groups.

In further embodiments, the solid pre-formulation comprises one or more additional components. In some embodiments, the solid pre-formulation comprises a buffer component, one or more therapeutic agents, viscosity enhancers, lubricity agents, or any combination thereof, wherein each of these identified components are added to the pre-formulation in its respective solid form. In some embodiments, the solid pre-formulation comprises a lubricity agent in its solid form. In certain embodiments, the solid pre-formulation comprises solid hyaluronic acid.

Liquid Component

The liquid component is added to the pre-formulation to form a liquid formulation, wherein the liquid formulation gels/polymerizes to form a hydrogel. In some embodiments, the liquid component is aqueous buffer. In some embodiments, the liquid component comprises buffer, one or more therapeutic agents, viscosity enhancer, water, saline, lubricity agents, or any combination thereof, wherein each of the variables identified are in its respective liquid or solution state. In some embodiments, the liquid component may also comprise a further first or second compound that is delivered in liquid or solution form.

In some embodiments, the additional components (e.g., the viscosity enhancer) improve the dissolution of the first and second compound upon addition of the liquid component. Furthermore, the viscosity of the liquid formulation formed after addition to the liquid component to the pre-formulation may be influenced by the viscosity enhancer.

Hydrogel

Once the liquid component is added to the solid pre-formulation, a liquid formulation is formed that can be delivered to a target site to form a biocompatible hydrogel polymer. The gelling time of the liquid formulation to form the biocompatible hydrogel polymer may be controlled through the selection of suitable first and second compounds and the concentration of the pre-formulation in the liquid component. In some embodiments, the gelling time is influenced by the pH of the liquid component. In some embodiments, the gelling time is influenced by the pH provided by the solid buffer component upon the addition of the liquid component. The bioabsorption of the hydrogel polymer is also controlled through the selection of first and second compounds. In some embodiments, the degradation of the hydrogel is controlled by the concentration of ester groups in the first or second compound. In some embodiments, the stickiness of the hydrogel polymer is influenced by the molar ratio of the first and second compound. In other embodiments, the stickiness of the hydrogel polymer is controlled by the percent of degradable acetate amine by mole equivalents. In some embodiments, the stickiness of the hydrogel polymer is controlled by the percent of degradable amine between the first compound and a different first compound.

Exemplary Solid Pre-Formulations

Provided herein are several types of exemplary pre-formulations, wherein the pre-formulations are in solid form. As several types of pre-formulations are presented herein, all descriptions pertaining pre-formulations are meant to encompass all the biocompatible pre-formulation presented herein. Furthermore, as the biocompatible hydrogel polymers are formed from the pre-formulations described herein, the descriptions pertaining to biocompatible hydrogel polymers are also meant to encompass all the biocompatible hydrogel polymers presented herein.

In some embodiments, the pre-formulation is polyglycol-based. In some embodiments, polyglycol-based pre-formulations include polyethylene glycol, polypropylene glycol, polybutylene glycol, polyalkyl glycols of various chain lengths, and any combination or copolymers thereof. In some embodiments, the polyglycol-based pre-formulation comprises polyethylene glycols (PEGs), methoxypolyethylene glycols (MPEGs), polypropylene glycols (PPGs), polybutylene glycols (PBGs), and polyglycol copolymers. In some embodiments, the biocompatible pre-formulation is PEG-based. In some embodiments, the pre-formulation is fully synthetic. In some embodiments, the pre-formulation is fully synthetic and PEG-based. In certain embodiments, the pre-formulation is fully synthetic and polyglycol based.

Presented herein is a solid polyglycol-based, fully synthetic, pre-formulation, comprising at least one first compound comprising more than two nucleophilic groups; and at least one second compound comprising more than two electrophilic groups; wherein the solid polyglycol based, fully synthetic, pre-formulation polymerizes and/or gels to form a polyglycol-based, fully synthetic, biocompatible hydrogel polymer in the presence of a liquid component. In some embodiments, the solid polyglycol-based, fully synthetic, pre-formulation is made by mixing the first compound and second compound to form a component. In some embodiments, the first compound further comprises a second first compound. In certain embodiments, the solid polyglycol-based, fully synthetic, pre-formulation, further comprises a solid buffer. In some embodiments, the solid polyglycol-based, fully synthetic, biocompatible hydrogel polymer at least partially adheres to a target site. In some embodiments, the solid polyglycol-based, fully synthetic, pre-formulation, further comprises a therapeutic agent. In some embodiments, the solid polyglycol-based, fully synthetic, pre-formulation, further comprises a viscosity enhancer. In some embodiments, the solid polyglycol-based, fully synthetic, pre-formulation, further comprises a radiopaque material or a pharmaceutically acceptable dye.

Also presented herein is a solid pre-formulation, comprising at least one first compound comprising more than two nucleophilic groups; and at least one second compound comprising more than two electrophilic groups; wherein the pre-formulation polymerizes and/or gels form a biocompatible hydrogel polymer in the presence of a liquid component. In some embodiments, the solid pre-formulation is made by mixing the first compound and second compound to form a solid component. In some embodiments, the first compound further comprises a second first compound. In some embodiments, the solid pre-formulation, further comprises a buffer. In some embodiments, the solid biocompatible hydrogel polymer at least partially adheres to a target site. In some embodiments, the solid pre-formulation, further comprises a therapeutic agent. In some embodiments, the solid pre-formulation, further comprises a viscosity enhancer. In some embodiments, the solid pre-formulation, further comprises a radiopaque material or a pharmaceutically acceptable dye.

Further presented herein is the pre-formulation comprising at least one first compound comprising more than one nucleophilic group, at least one second compound comprising more than one electrophilic group, and a buffer component providing pH range of about 5.0 to about 9.5, and optionally one or more therapeutic agents. In some embodiments the buffer is a solid buffer, wherein upon the addition of a liquid component as described to provide an aqueous buffer. In some embodiments, the buffer is an aqueous buffer. In certain embodiments, the pre-formulation forms a biocompatible hydrogel polymer at a target site in a human body by mixing the at least one first compound, the at least one second compound, and the optional therapeutic agent in the aqueous buffer and delivering the mixture to the target site such that the biocompatible hydrogel polymer at least in part polymerizes and/or gels at the target site. In some embodiments, the biocompatible hydrogel polymer is formed following mixing the first compound and the second compound in the aqueous buffer; and wherein the biocompatible hydrogel polymer gels at a target site. In certain embodiments, mixing the first compound, the second compound, and the optional therapeutic agent in the aqueous buffer and delivering the mixture to a target site in the human body generates the pre-formulation such that the pre-formulation at least in part polymerizes and/or gels at the target site to form a biocompatible hydrogel polymer. In some embodiments, the first compound further comprises a second first compound. In some embodiments, the first compound and second compound are combined to form a solid component where the biocompatible hydrogel polymer is formed upon the addition of the liquid component. In some embodiments, the solid component further comprises buffer. In certain embodiments, the solid component further comprises therapeutic agent. In some embodiments, the pre-formulation, further comprises a viscosity enhancer. In some embodiments, the pre-formulation, further comprises a radiopaque material or a pharmaceutically acceptable dye.

For certain embodiments of the solid pre-formulation, a liquid biocompatible formulation is formed from the addition of a liquid component to the solid pre-formulation. The liquid biocompatible formulation gels to form the biocompatible hydrogel polymer. In some embodiments, the liquid component comprises water, saline, a buffer, a therapeutic agent or a combination thereof. In certain embodiments, the liquid component comprises water. In certain embodiments, the liquid component comprises saline. In certain embodiments, the liquid component comprises a buffer. In certain embodiments, the liquid component comprises a therapeutic agent.

In some embodiments, the first or second compound comprises more than one nucleophilic or electrophilic group. In certain embodiments, the first or second compound comprises more than two nucleophilic or electrophilic groups. In some embodiments, the first or second compound is a polyol derivative. In certain embodiments, the first or second compound is a dendritic polyol derivative. In some embodiments, the first or second compound is a glycol, trimethylolpropane, glycerol, diglycerol, pentaerythritiol, sorbitol, hexaglycerol, tripentaerythritol, or polyglycerol derivative. In some embodiments, the first or second compound is a trimethylolpropane, glycerol, diglycerol, pentaerythritiol, sorbitol, hexaglycerol, tripentaerythritol, or polyglycerol derivative. In certain embodiments, the first or second compound is a glycol, trimethylolpropane, pentaerythritol, hexaglycerol, or tripentaerythritol derivative. In certain embodiments, the first or second compound is a trimethylolpropane, pentaerythritol, hexaglycerol, or tripentaerythritol derivative. In some embodiments, the first or second compound is a trimethylolpropane, glycerol, diglycerol, pentaerythritiol, sorbitol, hexaglycerol, tripentaerythritol, or polyglycerol derivative. In some embodiments, the first or second compound is a pentaerythritol, di-pentaerythritol, or tri-pentaerythritol derivative. In certain embodiments, the first or second compound is a hexaglycerol (2-ethyl-2-(hydroxymethyl)-1,3-propanediol, trimethylolpropane) derivative. In some embodiments, the first or second compound is a sorbitol derivative. In certain embodiments, the first or second compound is a glycol, propyleneglycol, glycerin, diglycerin, or polyglycerin derivative.

In some embodiments, the first and/or second compound further comprises polyethylene glycol (PEG) chains comprising one to 200 ethylene glycol subunits. In certain embodiments, the first and/or second compound further comprises polypropylene glycol (PPG) chains comprising one to 200 propylene glycol subunits. The PEG or PPG chains extending from the polyols are the "arms" linking the polyol core to the nucleophilic or electrophilic groups.

Exemplary Nucleophilic Monomers

The pre-formulation comprises at least one first compound comprising more than one nucleophilic group. In some embodiments, the pre-formulation comprises at least one first compound comprising more than two nucleophilic groups. In some embodiments, the nucleophilic group comprises a hydroxyl, thiol, or amino group. In preferred embodiments, the nucleophilic group comprises a thiol or amino group. In certain embodiments, the nucleophilic group comprises an amino group.

In certain embodiments, the nucleophilic group is connected to the polyol derivative through a suitable linker. Suitable linkers include, but are not limited to, esters (e.g., acetates) or ethers. In some instances, monomers comprising ester linkers are more susceptible to biodegradation. Examples of linkers comprising a nucleophilic group include, but are not limited to, mercaptoacetate, aminoacetate (glycin) and other amino acid esters (e.g., alanine, β-alanine, lysine, ornithine), 3-mercaptopropionate, ethylamine ether, or propylamine ether. In some embodiments, the polyol core derivative is bound to a polyethylene glycol or polypropylene glycol subunit, which is connected to the linker comprising the nucleophilic group. The molecular weight of the first compound (the nucleophilic monomer) is about 500 to 40000. In certain embodiments, the molecular weight of a first compound (a nucleophilic monomer) is about 100, about 500, about 1000, about 2000, about 3000, about 4000, about 5000, about 6000, about 7000, about 8000, about 9000, about 10000, about 12000, about 15000, about 20000, about 25000, about 30000, about 35000, about 40000, about 50000, about 60000, about 70000, about 80000, about 90000, or about 100000. In some embodiments, the molecular weight of a first compound is about 500 to 2000. In certain embodiments, the molecular weight of a first compound is about 15000 to about 40000. In some embodiments, the first compound is water soluble.

In some embodiments, the first compound is a MULTIARM-(5k-50k)-polyol derivative comprising polyglycol subunits and more than two nucleophilic groups. MULTIARM refers to number of polyglycol subunits that are attached to the polyol core and these polyglycol subunits link the nucleophilic groups to the polyol core. In some embodiments, MULTIARM is 3ARM, 4ARM, 6ARM, 8ARM, 10ARM, or 12ARM. In some embodiments, MULTIARM is 3ARM, 4ARM, 6ARM, or 8ARM. In some embodiments, the MULTIARM is 4ARM or 8ARM. In some embodiments, the first compound is MULTIARM-(5k-50k)-SH, MULTIARM-(5k-50k)-NH2, MULTIARM-(5k-50k)-AA, or a combination thereof. In certain embodiments, the first compound is 4ARM-(5k-50k)-SH, 4ARM-(5k-50k)-NH2, 4ARM-(5k-50k)-AA, 8ARM-(5k-50k)-NH2, 8ARM-(5k-50k)-AA or a combination thereof. In some embodiments, the polyol derivative is a trimethylolpropane, diglycerol, pentaerythritol, sorbitol, hexaglycerol, tripentaerythritol, or polyglycerol derivative.

Examples of the construction of monomers comprising more than one nucleophilic group are shown below with a trimethylolpropane or pentaerythritol core polyol. The compounds shown have thiol or amine electrophilic groups that are connected to variable lengths PEG subunit through acetate, propionate or ethyl ether linkers (e.g., structures below of ETTMP (A; n=1), 4ARM-PEG-NH2 (B; n=1), and 4ARM-PEG-AA (C; n=1)). Monomers using other polyol cores are constructed in a similar way.

A:

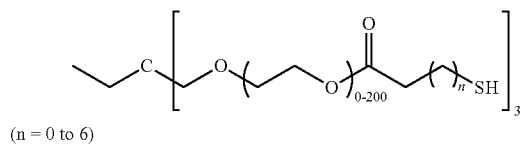

(n = 0 to 6)

B:

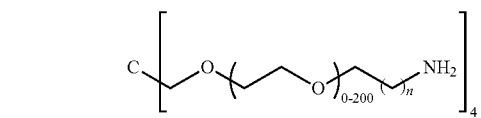

(n = 0 to 6)

C:

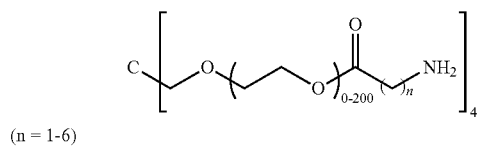

(n = 1-6)

Suitable first compounds comprising a nucleophilic group (used in the amine-ester chemistry) include, but are not limited to, pentaerythritol polyethylene glycol amine (4ARM-PEG-NH2) (molecular weight selected from about 5000 to about 40000, e.g., 5000, 10000, or 20000), pentaerythritol polyethylene glycol amino acetate (4ARM-PEG-AA) (molecular weight selected from about 5000 to about 40000, e.g., 5000, 10000, or 20000), hexaglycerin polyethylene glycol amine (8ARM-PEG-NH2) (molecular weight selected from about 5000 to about 40000, e.g., 10000, 20000, or 40000), or tripentaerythritol glycol amine (8ARM(TP)-PEG-NH2) (molecular weight selected from about 5000 to about 40000, e.g., 10000, 20000, or 40000). Within this class of compounds, 4 (or 8)ARM-PEG-AA comprises ester (or acetate) groups while the 4 (or 8)ARM-PEG-NH2 monomers do not comprise ester (or acetate) groups. In some embodiments, the first compound is 4ARM-5k-SH, 4ARM-2k-NH2, 4ARM-5k-NH2, 8ARM-20k-NH2, 4ARM-20k-AA, or 8ARM-20k-AA. In some embodiments, the first compound is 4ARM-5k-SH, 4ARM-2k-NH2, 4ARM-5k-NH2, 8ARM-20k-NH2, 4ARM-20k-AA, 8ARM-20k-AA, or a combination thereof. In certain embodiments, the first compound further comprising a second first compound is 4ARM-5k-SH, 4ARM-2k-NH2, 4ARM-5k-NH2, 8ARM-20k-NH2, 4ARM-20k-AA, or 8ARM-20k-AA.

Other suitable first compounds comprising a nucleophilic group (used in the thiol-ester chemistry) include, but not limited to, glycol dimercaptoacetate (THIOCURE® GDMA), trimethylolpropane trimercaptoacetate (THIOCURE® TMPMA), pentaerythritol tetramercaptoacetate (THIOCURE® PETMA), glycol di-3-mercaptopropionate (THIOCURE® GDMP), trimethylolpropane tri-3-mercaptopropionate (THIOCURE® TMPMP), pentaerythritol tetra-3-mercaptopropionate (THIOCURE® PETMP), polyol-3-mercaptopropionates, polyester-3-mercaptopropionates, propyleneglycol 3-mercaptopropionate (THIOCURE® PPGMP 800), propyleneglycol 3-mercaptopropionate (THIOCURE® PPGMP 2200), ethoxylated trimethylolpropane tri-3-mercaptopropionate (THIOCURE® ETTMP-700), and ethoxylated trimethylolpropane tri-3-mercaptopropionate (THIOCURE® ETTMP-1300).

Exemplary Electrophilic Monomers

The pre-formulation comprises at least one second compound comprising more than one electrophilic group. In some embodiments, the pre-formulation comprises at least one second compound comprising more than two electrophilic groups. In some embodiments, the electrophilic group is an epoxide, maleimide, succinimidyl, or an alpha-beta unsaturated ester. In preferred embodiments, the electrophilic group is an epoxide or succinimidyl. In some embodiments, the electrophilic group is N-succinimidyl glutaramide.

In certain embodiments, the electrophilic group is connected to the polyol derivative through a suitable linker. Suitable linkers include, but are not limited to, esters, amides, or ethers. In some instances, monomers comprising ester linkers are more susceptible to biodegradation. Examples of linkers comprising an electrophilic group include, but are not limited to, succinimidyl succinate, succinimidyl glutarate, succinimidyl succinamide, succinimidyl glutaramide, or glycidyl ether. In some embodiments, the polyol core derivative is bound to a polyethylene glycol or polypropylene glycol subunit, which is connected to the linker comprising the electrophilic group. The molecular weight of the second compound (the electophilic monomer) is about 500 to 40000. In certain embodiments, the molecular weight of a second compound (an electophilic monomer) is about 100, about 500, about 1000, about 2000, about 3000, about 4000, about 5000, about 6000, about 7000, about 8000, about 9000, about 10000, about 12000, about 15000, about 20000, about 25000, about 30000, about 35000, about 40000, about 50000, about 60000, about 70000, about 80000, about 90000, or about 100000. In some embodiments, the molecular weight of a second compound is about 500 to 2000. In certain embodiments, the molecular weight of a second compound is about 15000 to about 40000. In some embodiments, the second compound is water soluble.

In some embodiments, the second compound is a MULTI-ARM-(5k-50k)-polyol derivative comprising polyglycol subunits and more than two electrophilic groups. MULTI-ARM refers to number of polyglycol subunits that are attached to the polyol core and these polyglycol subunits link the nucleophilic groups to the polyol core. In some embodiments, MULTIARM is 3ARM, 4ARM, 6ARM, 8ARM, 10ARM, or 12ARM. In some embodiments, MULTIARM is 3ARM, 4ARM, 6ARM, or 8ARM. In some embodiments, MULTIARM is 4ARM or 8ARM. In certain embodiments, the second compound MULTIARM-(5-50k)-SG, MULTI-ARM-(5-50k)-SGA, MULTIARM-(5-50k)-SS, MULTI-ARM-(5-50k)-SSA, or a combination thereof. In certain embodiments, the second compound is 4ARM-(5-50k)-SG, 4ARM-(5-50k)-SGA, 4ARM-(5-50k)-SS, 8ARM-(5-50k)-SG, 8ARM-(5-50k)-SGA, 8ARM-(5-50k)-SS, or a combination thereof. In some embodiments, the polyol derivative is a trimethylolpropane, diglycerol, pentaerythritol, sorbitol, hexaglycerol, tripentaerythritol, or polyglycerol derivative.

Examples of the construction of monomers comprising more than one electrophilic group are shown below with a pentaerythritol core polyol. The compounds shown have a succinimidyl electrophilic group, a glutarate or glutaramide linker, and a variable lengths PEG subunit (e.g., structures below of 4ARM-PEG-SG (D; n=3) and 4ARM-PEG-SGA (E; n=3)). Monomers using other polyol cores or different linkers (e.g., succinate (SS) or succinamide (SSA) are constructed in a similar way.

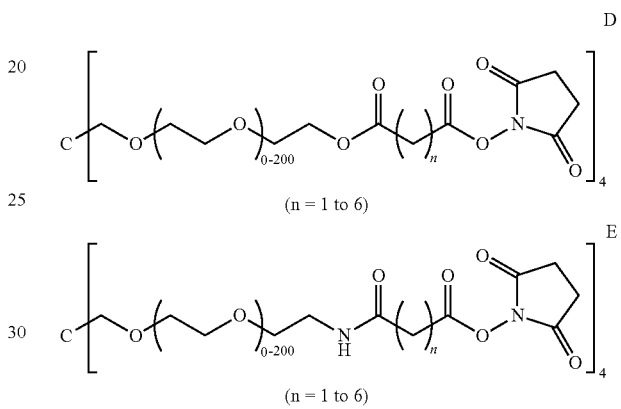

Suitable second compounds comprising an electrophilic group include, but are not limited to, pentaerythritol polyethylene glycol maleimide (4ARM-PEG-MAL) (molecular weight selected from about 5000 to about 40000, e.g., 10000 or 20000), pentaerythritol polyethylene glycol succinimidyl succinate (4ARM-PEG-SS) (molecular weight selected from about 5000 to about 40000, e.g., 10000 or 20000), pentaerythritol polyethylene glycol succinimidyl glutarate (4ARM-PEG-SG) (molecular weight selected from about 5000 to about 40000, e.g., 10000 or 20000), pentaerythritol polyethylene glycol succinimidyl glutaramide (4ARM-PEG-SGA) (molecular weight selected from about 5000 to about 40000, e.g., 10000 or 20000), hexaglycerin polyethylene glycol succinimidyl succinate (8ARM-PEG-SS) (molecular weight selected from about 5000 to about 40000, e.g., 10000 or 20000), hexaglycerin polyethylene glycol succinimidyl glutarate (8ARM-PEG-SG) (molecular weight selected from about 5000 to about 40000, e.g., 10000, 15000, 20000, or 40000), hexaglycerin polyethylene glycol succinimidyl glutaramide (8ARM-PEG-SGA) (molecular weight selected from about 5000 to about 40000, e.g., 10000, 15000, 20000, or 40000), tripentaerythritol polyethylene glycol succinimidyl succinate (8ARM(TP)-PEG-SS) (molecular weight selected from about 5000 to about 40000, e.g., 10000 or 20000), tripentaerythritol polyethylene glycol succinimidyl glutarate (8ARM(TP)-PEG-SG) (molecular weight selected from about 5000 to about 40000, e.g., 10000, 15000, 20000, or 40000), or tripentaerythritol polyethylene glycol succinimidyl glutaramide (8ARM(TP)-PEG-SGA) (molecular weight selected from about 5000 to about 40000, e.g., 10000, 15000, 20000, or 40000). The 4 (or 8)ARM-PEG-SG monomers comprise ester groups, while the 4 (or 8)ARM-PEG-SGA monomers do not comprise ester groups. In some embodiments, the second compound is 4ARM-10k-SG, 8ARM-15k-SG, 4ARM-20k-SGA, and 4ARM-10k-SS. In some embodiments, the second compound is 4ARM-10k-SG, 8ARM-15k-SG, 4ARM-20k-SGA, 4ARM-10k-SS, or a combination thereof. In certain embodiments, the first compound is 8ARM-20k-NH2 and/or 8ARM-20k-AA, and the second compound is 4ARM-20k-SGA.

Other suitable second compounds comprising an electrophilic group are sorbitol polyglycidyl ethers, including, but not limited to, sorbitol polyglycidyl ether (DENACOL® EX-611), sorbitol polyglycidyl ether (DENACOL® EX-612), sorbitol polyglycidyl ether (DENACOL® EX-614), sorbitol polyglycidyl ether (DENACOL® EX-614B), polyglycerol polyglycidyl ether (DENACOL® EX-512), polyglycerol polyglycidyl ether (DENACOL® EX-521), diglycerol polyglycidyl ether (DENACOL® EX-421), glycerol polyglycidyl ether (DENACOL® EX-313), glycerol polyglycidyl ether (DENACOL® EX-313), trimethylolpropane polyglycidyl ether (DENACOL® EX-321), sorbitol polyglycidyl ether (DENACOL® EJ-190).

Formation of Hyrdogels

In certain embodiments, the first and second compounds comprising more than one nucleophilic or more than one electrophilic group safely undergo polymerization at a target site inside or on a mammalian body, for instance at the site of a wound or in a joint. In certain embodiments, the first and second compounds comprising more than two nucleophilic or more than two electrophilic groups safely undergo polymerization at a target site inside or on a mammalian body, for instance at the site of a wound or in a joint. In certain embodiments, the pre-formulation forms a wound patch, suture, or joint spacer after addition of a liquid component. In some embodiments, the first compound and the second compound are monomers forming a polymer through the reaction of a nucleophilic group in the first compound with the electrophilic group in the second compound. In certain embodiments, the monomers are polymerized at a predetermined time. In some embodiments, the monomers are polymerized under mild and nearly neutral pH conditions. In certain embodiments, the hydrogel polymer does not change volume after curing.

In some embodiments, the first and second compounds react to form amide, thioester, or thioether bonds. When a thiol nucleophile reacts with a succinimidyl electrophile, a thioester is formed. When an amino nucleophile reacts with a succinimidyl electrophile, an amide is formed.

In some embodiments, one or more first compounds comprising an amino group react with one or more second compounds comprising a succinimidyl ester group to form amide linked first and second monomer units. In certain embodiments, one or more first compounds comprising a thiol group react with one or more second compounds comprising a succinimidyl ester group to form thioester linked first and second monomer units. In some embodiments, one or more first compounds comprising an amino group react with one or more second compounds comprising an epoxide group to from amine linked first and second monomer units. In certain embodiments, one or more first compounds comprising a thiol group react with one or more second compounds comprising an epoxide group to form thioether linked first and second monomer units.

In some embodiments, the biocompatible hydrogel polymer comprises at least one first monomeric unit bound through at least one amide, thioester, or thioether linkage to at least one second monomeric unit; and at least one second monomeric unit bound to at least one first monomeric unit; wherein the biocompatible hydrogel polymer is formed from contacting a solid pre-formulation with a liquid component. In some embodiments, the biocompatible hydrogel polymer, comprises at least one first monomeric unit bound through at least one amide linkage to at least one second monomeric unit; and at least one second monomeric unit bound to at least one first monomeric unit; wherein biocompatible hydrogel polymer is formed from contacting a solid pre-formulation with a liquid component. In certain embodiments, the first monomeric unit is a glycol, trimethylolpropane, pentaerythritol, hexaglycerol, or tripentaerythritol derivative. In some embodiments, the first monomeric unit further comprises one or more polyethylene glycol sections. In certain embodiments, the first monomeric unit is a pentaerythritol or hexaglycerol derivative. In some embodiments, the second monomeric unit is a polyol derivative. In certain embodiments, the second monomeric unit is a trimethylolpropane, glycerol, diglycerol, pentaerythritol, sorbitol, hexaglycerol, tripentaerythritol, or polyglycerol derivative. In some embodiments, the second monomeric further comprises one or more polyethylene glycol sections. In certain embodiments, the second monomeric unit is a trimethylolpropane, pentaerythritol, or hexaglycerol derivative.

In some embodiments, a solid first compound is mixed with a different solid first compound, or solid second first compound, before addition to one or more solid second compounds. In other embodiments, a solid second compound is mixed with a different solid second compound before addition to one or more solid first compounds. In certain embodiments, the properties of the pre-formulation and the biocompatible hydrogel polymer are controlled by the properties of the at least one first and at least one second monomer mixture.

In some embodiments, one first compound is used in the biocompatible hydrogel polymer. In certain embodiments, two different first compounds are mixed and used in the biocompatible hydrogel polymer. In some embodiments, three different first compounds are mixed and used in the biocompatible hydrogel polymer. In certain embodiments, four or more different first compounds are mixed and used in the biocompatible hydrogel polymer.

In some embodiments, one second compound is used in the biocompatible hydrogel polymer. In certain embodiments, two different second compounds are mixed and used in the biocompatible hydrogel polymer. In some embodiments, three different second compounds are mixed and used in the biocompatible hydrogel polymer. In certain embodiments, four or more different second compounds are mixed and used in the biocompatible hydrogel polymer.

In some embodiments, a first compound comprising ether linkages to the nucleophilic group are mixed with a different first compound comprising ester linkages to the nucleophilic group. This allows the control of the concentration of ester groups in the resulting biocompatible hydrogel polymer. In certain embodiments, a second compound comprising ester linkages to the electrophilic group are mixed with a different second compound comprising ether linkages to the electrophilic group. In some embodiments, a second compound comprising ester linkages to the electrophilic group are mixed with a different second compound comprising amide linkages to the electrophilic group. In certain embodiments, a second compound comprising amide linkages to the electrophilic group are mixed with a different second compound comprising ether linkages to the electrophilic group.

In some embodiments, a first compound comprising an aminoacetate nucleophile is mixed with a different first compound comprising an ethylamine ether nucleophile at a specified molar ratio (x/y). In certain embodiments, the molar ratio (x/y) is 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. In certain embodiments, the mixture of two first compounds is mixed with one or more second compounds at a molar amount equivalent to the sum of x and y.

In some embodiments, the solid pre-formulation comprising first compound comprising more than one nucleophilic group and the second compound comprising more than one electrophilic group is mixed together with a liquid component comprising an aqueous buffer in the pH range of about 5.0 to about 9.5, whereby a biocompatible hydrogel polymer is formed.

In some embodiments, the solid pre-formulation comprising first or second compound comprises more than two nucleophilic or electrophilic groups. In some embodiments, the first and second compounds are combined first to form a solid component and the compounds are mixed together upon the addition of a liquid component comprising an aqueous buffer which may optionally further comprise a therapeutic agent.

In some embodiments, the buffer component is provided in solid form and an aqueous buffer is provided upon the addition of a liquid component. In some embodiments, the liquid component can be water or saline. In certain embodiments, the liquid component further comprises a therapeutic agent. In certain embodiments, the solid first compound, the solid second compound and solid buffer are combined first to form a solid component, wherein the compounds are mixed together upon the addition of a liquid component. In other embodiments, the solid first compound, the solid second compound, and at least one solid therapeutic agent are combined first to make a solid component, wherein the compounds are mixed together upon the addition of a liquid component or aqueous buffer. In other embodiments, the solid first compound, the solid second compound, solid buffer, and at least one solid therapeutic agent are combined first to make a solid component, wherein the compounds are mixed together upon the addition of a liquid component. In some embodiments, the therapeutic agent is hyaluronic acid which can be added to the solid component in solid form or added to the liquid component.

In certain embodiments, the concentration of the monomers in the aqueous is from about 1% to about 100%. In some embodiments, the dilution is used to adjust the viscosity of the monomer dilution. In certain embodiments, the concentration of a monomer in the aqueous buffer is about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the electrophilic and nucleophilic monomers are mixed in such ratio that there is a slight excess of electrophilic groups present in the mixture. In certain embodiments, this excess is about 10%, about 5%, about 2%, about 1%, about 0.9%, about 0.8%, about 0.7%, about 0.6%, about 0.5%, about 0.4%, about 0.3%, about 0.2%, about 0.1%, or less than 0.1%.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the pre-formulation. In certain embodiments, temperature influences the gelling time of the pre-formulation. In some embodiments, the type of aqueous buffer influences the gelling time of the pre-formulation. In certain embodiments, the concentration of the aqueous buffer influences the gelling time of the pre-formulation. In some embodiments, the nucleophilicity and/or electrophilicity of the nucleophilic and electrophilic groups of the monomers influences the gelling time of the pre-formulation.

In some embodiments, the gelling time or curing time of the biocompatible hydrogel polymer is controlled by the pH of the aqueous buffer. In certain embodiments, the gelling time is between about 20 seconds and 10 minutes. In some embodiments, the gelling time is less than 30 minutes, less than 20 minutes, less than 10 minutes, less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.4 minutes, less than 1.2 minutes, less than 1.0 minutes, less than 0.8 minutes, less than 0.6 minutes, or less than 0.4 minutes. In certain embodiments, the pH of the aqueous buffer is from about 5 to about 9.5. In some embodiments, the pH of the aqueous buffer is from about 7.0 to about 9.5. In specific embodiments, the pH of the aqueous buffer is about 8. In some embodiments, the pH of the aqueous buffer is about 5, about 5.5, about 6.0, about 6.5, 6.6, about 6.7, about 6.8, about 6.9, about 7.0, about 7.1, about 7.2, about 7.3, about 7.4, about 7.5, about 7.6, about 7.8, about 7.9, about 8.0, about 8.1 about 8.2 about 8.3, about 8.4, about 8.5, about 9.0, or about 9.5.

In some embodiments, the gelling time or curing time of the biocompatible hydrogel polymer is controlled by the pH provided by the buffer component. In certain embodiments, the gelling time is between about 20 seconds and 10 minutes. In some embodiments, the gelling time is less than 30 minutes, less than 20 minutes, less than 10 minutes, less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.4 minutes, less than 1.2 minutes, less than 1.0 minutes, less than 0.8 minutes, less than 0.6 minutes, or less than 0.4 minutes. In certain embodiments, the pH provided by the buffer is from about 5 to about 9.5. In some embodiments, the pH provided by the buffer is from about 7.0 to about 9.5. In specific embodiments, the pH provided by the buffer is about 8. In some embodiments, the pH of the aqueous buffer is about 5, about 5.5, about 6.0, about 6.5, about 6.6, about 6.7, about 6.8, about 6.9, about 7.0, about 7.1, about 7.2, about 7.3, about 7.4, about 7.5, about 7.6, about 7.8, about 7.9, about 8.0, about 8.1 about 8.2 about 8.3, about 8.4, about 8.5, about 9.0, or about 9.5.

In certain embodiments, the gelling time or curing time of the biocompatible hydrogel polymer is controlled by the type of buffer. In some embodiments, the aqueous buffer is a physiologically acceptable buffer. In some embodiments, a solid buffer is used in the pre-formulation and becomes an aqueous buffer after the additionof a liquid component. In certain embodiments, an aqueous buffer is used in the pre-formulation. In certain embodiments, aqueous buffers include, but are not limited to, aqueous saline solutions, phosphate buffered saline, borate buffered saline, a combination of borate and phosphate buffers wherein each component is dissolved in separate buffers, N-2-Hydroxyethylpiperazine-N'-2-hydroxypropanesulfonic acid (HEPES), 3-(N-Morpholino) propanesulfonic acid (MOPS), 2-([2-Hydroxy-1,1- bis(hydroxymethyl)ethyl]amino)ethanesulfonic acid (TES), 3-[N-tris(Hydroxy-methyl) ethylamino]-2-hydroxyethyl]-1-piperazinepropanesulfonic acid (EPPS), Tris[hydroxymethyl]-aminomethane (THAM), and Tris[hydroxymethyl] methyl aminomethane (TRIS). In some embodiments, the thiol-ester chemistry (e.g., ETTMP nucleophile with SGA or SG electrophile) is performed in borate buffer. In certain embodiments, the amine-ester chemistry (NH2 or AA nucleophile with SGA or SG electrophile) is performed in phosphate buffer.

In certain embodiments, the first compound and the second compound do not react with the therapeutic agent during formation of the biocompatible hydrogel polymer. In some embodiments, the therapeutic agent remains unchanged after polymerization of the first and second compounds (i.e., monomers). In certain embodiments, the therapeutic agent does not change the properties of the hydrogel polymer. In some embodiments, the physiochemical properties of the therapeutic agent and the hydrogel polymer formulation are not affected by the polymerization of the monomers.

In some embodiments, the hydrogel polymer formulations further comprise a viscosity enhancer. Examples of viscosity enhancer include, but are not limited to, hydroxyethylcellulose, hydroxypropylcellulose, methylcellulose, polyvinylcellulose, polyvinylpyrrolidone.

Area of for Treatment—Target Sites

In certain embodiments, the target site is inside a mammal. In some embodiments, the target site is inside a human being. In certain embodiments, the target site is on the human body. In some embodiments, the target site is accessible through surgery. In certain embodiments, the target site is accessible through minimally invasive surgery. In some embodiments, the target site is accessible through an endoscopic device. In certain embodiments, the target site is a wound on the skin of a mammal. In other embodiments, the target site is in a joint or on a bone of an animal.

In some embodiments, a pre-formulation or a biocompatible hydrogel polymer is used as a sealant or adhesive with or without a therapeutic agent. In certain embodiments, the pre-formulation or biocompatible hydrogel polymer is used to seal a wound on a mammal. In other embodiments, the pre-formulation or biocompatible hydrogel polymer is used to fill cavities in the human body, e.g., in a joint space to form a gel cushion.

Delivery of the Hydrogel Formulation to a Target Site

In some embodiments, the pre-formulation is delivered as a biocompatible formulation to a target site through a catheter or a needle to form a biocompatible hydrogel polymer at the target site. In certain embodiments, the needle or catheter is attached or part of a delivery device.

In other embodiments, the formulation is delivered to the target site in or on the mammal using a syringe and needle. In some embodiments, a delivery device is used to deliver the pre-formulation to the target site. In some embodiments, the needle has an outer diameter of about 4 mm, about 3.8 mm, about 3.6 mm, about 3.4 mm, about 3.2 mm, about 3.0 mm, about 2.8 mm, about 2.6 mm, about 2.4 mm, about 2.2 mm, about 2.0 mm, about 1.8 mm, about 1.6 mm, about 1.4 mm, about 1.2 mm, about 1.0 mm, about 0.8 mm, or about 0.6 mm. In preferred embodiments, the needle has an outer diameter of about 1.2 mm or less. In certain embodiments, the viscosity of the pre-formulation is close to the viscosity of water when delivering the mixture to the site of the tumor through the catheter. In some embodiments, the pre-formulation forming the biocompatible hydrogel further comprises a pharmaceutically acceptable viscosity enhancer to ensure that the pre-formulation stays in place at the target site during the gelling process.

In certain embodiments, between 1 and 3 mL of the pre-formulation optionally comprising a therapeutic agent is delivered to a target site. In some embodiments, about 12 mL, about 11 mL, about 10 mL, about 9 mL, about 8 mL, about 7.5 mL, about 7.0 mL, about 6.5 mL, about 6.0 mL, about 5.5 mL, about 5.0 mL, about 4.5 mL, about 4.0 mL, about 3.5 mL, about 3.0 mL, about 2.5 mL, about 2.0 mL, about 1.5 mL, about 1.0 mL, about 0.5 mL, about 0.2 mL, about 0.1 mL, about 0.05 mL or about 0.01 mL pre-formulation optionally comprising a therapeutic agent is delivered to a target site. In certain embodiments, less than 12 mL, less than 11 mL, less than 10 mL, less than 9 mL, less than 8 mL, less than 7.5 mL, less than 7.0 mL, less than 6.5 mL, less than 6.0 mL, less than 5.5 mL, less than 5.0 mL, less than 4.5 mL, less than 4.0 mL, less than 3.5 mL, less than 3.0 mL, less than 2.5 mL, less than 2.0 mL, less than 1.5 mL, less than 1.0 mL, less than 0.5 mL, less than 0.2 mL, less than 0.1 mL, less than 0.05 mL, or less than 0.01 mL pre-formulation optionally comprising a therapeutic agent is delivered to a target site. In certain embodiments, about 0.05 to 5 mL pre-formulation optionally comprising a therapeutic agent is delivered to a target site.

In some embodiments, the gelling time of the biocompatible hydrogel polymer is set according to the preference of the doctor delivering the hydrogel polymer mixture to a target site. In most instances, a physician delivers the hydrogel polymer mixture to the target within 15 to 30 seconds. In some embodiments, the hydrogel polymer mixture gels after delivery at the target site, covering the target site.

In some embodiments, the gelling time or curing time of the biocompatible hydrogel polymer is controlled by the pH of the aqueous buffer. In certain embodiments, the gelling time is between about 20 seconds and 10 minutes. In preferred embodiments, the gelling time is about 90 seconds. In some embodiments, the gelling time is less than 120 minutes, less than 90 minutes, less than 60 minutes, less than 50 minutes, less than 40 minutes, less than 30 minutes, less than 20 minutes, less than 10 minutes, less than 9 minutes, less than 8 minutes, less than 7 minutes, less than 6 minutes, less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.5 minutes, less than 1.4 minutes, less than 1.2 minutes, less than 1.0 minutes, less than 0.8 minutes, less than 0.6 minutes, or less than 0.4 minutes. In certain embodiments, the gelling time is more than 120 minutes, more than 90 minutes, more than 60 minutes, more than 50 minutes, more than 40 minutes, more than 30 minutes, more than 20 minutes, more than 10 minutes, more than 9 minutes, more than 8 minutes, more than 7 minutes, more than 6 minutes, more than 5 minutes, more than 4.8 minutes, more than 4.6 minutes, more than 4.4 minutes, more than 4.2 minutes, more than 4.0 minutes, more than 3.8 minutes, more than 3.6 minutes, more than 3.4 minutes, more than 3.2 minutes, more than 3.0 minutes, more than 2.8 minutes, more than 2.6 minutes, more than 2.4 minutes, more than 2.2 minutes, more than 2.0 minutes, more than 1.8 minutes, more than 1.6 minutes, more than 1.5 minutes, more than 1.4 minutes, more than 1.2 minutes, more than 1.0 minutes, more than 0.8 minutes, more than 0.6 minutes, or more than 0.4 minutes. In some embodiments, the gelling time is about 120 minutes, about 90 minutes, about 60 minutes, about 50 minutes, about 40 minutes, about 30 minutes, about 20 minutes, about 10 minutes, about 9 minutes, about 8 minutes, about 7 minutes, about 6 minutes, about 5 minutes, about 4.8 minutes, about 4.6 minutes, about 4.4 minutes, about 4.2 minutes, about 4.0 minutes, about 3.8 minutes, about 3.6 minutes, about 3.4 minutes, about 3.2 minutes, about 3.0 minutes, about 2.8 minutes, about 2.6 minutes, about 2.4 minutes, about 2.2 minutes, about 2.0 minutes, about 1.8 minutes, about 1.6 minutes, about 1.5 minutes, about 1.4 minutes, about 1.2 minutes, about 1.0 minutes, about 0.8 minutes, about 0.6 minutes, or about 0.4 minutes.

In some embodiments, the gelling time or curing time of the biocompatible hydrogel polymer is controlled by the pH provided by the buffer component. In certain embodiments, the gelling time is between about 20 seconds and 10 minutes. In preferred embodiments, the gelling time is about 90 seconds. In some embodiments, the gelling time is less than 120 minutes, less than 90 minutes, less than 60 minutes, less than 50 minutes, less than 40 minutes, less than 30 minutes, less than 20 minutes, less than 10 minutes, less than 9 minutes, less than 8 minutes, less than 7 minutes, less than 6 minutes, less than 5 minutes, less than 4.8 minutes, less than 4.6 minutes, less than 4.4 minutes, less than 4.2 minutes, less than 4.0 minutes, less than 3.8 minutes, less than 3.6 minutes, less than 3.4 minutes, less than 3.2 minutes, less than 3.0 minutes, less than 2.8 minutes, less than 2.6 minutes, less than 2.4 minutes, less than 2.2 minutes, less than 2.0 minutes, less than 1.8 minutes, less than 1.6 minutes, less than 1.5 minutes, less than 1.4 minutes, less than 1.2 minutes, less than 1.0 minutes, less than 0.8 minutes, less than 0.6 minutes, or less than 0.4 minutes. In certain embodiments, the gelling time is more than 120 minutes, more than 90 minutes, more than 60 minutes, more than 50 minutes, more than 40 minutes, more than 30 minutes, more than 20 minutes, more than 10 minutes, more than 9 minutes, more than 8 minutes, more than 7 minutes, more than 6 minutes, more than 5 minutes, more than 4.8 minutes, more than 4.6 minutes, more than 4.4 minutes, more than 4.2 minutes, more than 4.0 minutes, more than 3.8 minutes, more than 3.6 minutes, more than 3.4 minutes, more than 3.2 minutes, more than 3.0 minutes, more than 2.8 minutes, more than 2.6 minutes, more than 2.4 minutes, more than 2.2 minutes, more than 2.0 minutes, more than 1.8 minutes, more than 1.6 minutes, more than 1.5 minutes, more than 1.4 minutes, more than 1.2 minutes, more than 1.0 minutes, more than 0.8 minutes, more than 0.6 minutes, or more than 0.4 minutes. In some embodiments, the gelling time is about 120 minutes, about 90 minutes, about 60 minutes, about 50 minutes, about 40 minutes, about 30 minutes, about 20 minutes, about 10 minutes, about 9 minutes, about 8 minutes, about 7 minutes, about 6 minutes, about 5 minutes, about 4.8 minutes, about 4.6 minutes, about 4.4 minutes, about 4.2 minutes, about 4.0 minutes, about 3.8 minutes, about 3.6 minutes, about 3.4 minutes, about 3.2 minutes, about 3.0 minutes, about 2.8 minutes, about 2.6 minutes, about 2.4 minutes, about 2.2 minutes, about 2.0 minutes, about 1.8 minutes, about 1.6 minutes, about 1.5 minutes, about 1.4 minutes, about 1.2 minutes, about 1.0 minutes, about 0.8 minutes, about 0.6 minutes, or about 0.4 minutes.

In certain embodiments, the pH of the aqueous buffer is from about 5.0 to about 9.5. In some embodiments, the pH of the aqueous buffer is from about 6.0 to about 8.5. In specific embodiments, the pH of the aqueous buffer is about 8.0. In some embodiments, the pH is about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.9, about 9, about 9.1 about 9.2, about 9.3, about 9.4, or about 9.5.

In certain embodiments, the pH provided by the buffer is from about 5.0 to about 9.5. In some embodiments, the pH provided by the buffer is from about 6.0 to about 8.5. In specific embodiments, the pH provided by the buffer is about 8.0. In some embodiments, the pH is about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.9, about 9, about 9.1 about 9.2, about 9.3, about 9.4, or about 9.5.

In certain embodiments, the gelling time or curing time of the biocompatible hydrogel polymer is controlled by the selection of the first and second compounds. In some embodiments, the concentration of nucleophilic or electrophilic groups in the first or second compound influences the gelling time of the pre-formulation.

In some embodiments, curing of the biocompatible hydrogel polymer is verified post-administration. In certain embodiments, the verification is performed in vivo at the delivery site. In other embodiments, the verification is performed ex vivo. In some embodiments, curing of the biocompatible hydrogel polymer is verified visually. A lack of flow of the biocompatible hydrogel polymer indicates that the biocompatible hydrogel polymer has gelled and the hydrogel is sufficiently cured. In further embodiments, curing of the biocompatible hydrogel polymer is verified by evaluation of the residue in the delivery device, for instance the residue in the catheter of the bronchoscope or other endoscopic device, or the residue in the syringe used to deliver the biocompatible hydrogel polymer. In other embodiments, curing of the biocompatible hydrogel polymer is verified by depositing a small sample (e.g., ~1 mL) on a piece of paper or in a small vessel and subsequent evaluation of the flow characteristics after the gelling time has passed.

In some embodiments, the pre-formulation optionally comprising one or more therapeutic agents is delivered to the target site so that the pre-formulation mostly covers the target site. In certain embodiments, the pre-formulation substantially covers an exposed portion of diseased tissue. In some embodiments, the pre-formulation does not spread to any other location intentionally. In some embodiments, the pre-formulation substantially covers diseased tissue and does not significantly cover healthy tissue. In certain embodiments, the biocompatible hydrogel polymer does not significantly cover healthy tissue. In some embodiments, pre-formulation gels over the target site and thoroughly covers diseased tissue. In some embodiments, the biocompatible hydrogel polymer adheres to tissue.

Bioabsorbance of the Hydrogel

In some embodiments, the biocompatible hydrogel polymer is a bioabsorbable polymer. In certain embodiments, the biocompatible hydrogel polymer is bioabsorbed within about 5 to 30 days. In some embodiments, the biocompatible hydrogel polymer is bioabsorbed within about 30 to 180 days. In preferred embodiments, the biocompatible hydrogel polymer is bioabsorbed within about 1 to 70 days. In some embodiments the biocompatible hydrogel polymer is bioabsorbed within about 365 days, 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, or about 1 day. In certain embodiments the biocompatible hydrogel polymer is bioabsorbed within less than 365 days, 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, or less than 1 day. In some embodiments the biocompatible hydrogel polymer is bioabsorbed within more than 365 days, 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, or more than 1 day. In some embodiments, the biocompatible hydrogel polymer is substantially non-bioabsorbable.

The biocompatible hydrogel polymer is slowly bioabsorbed, dissolved, and or excreted. In some instances, the rate of bioabsorption is controlled by the number of ester groups in the biocompatible and/or biodegradable hydrogel polymer. In other instances, the higher the concentration of ester units is in the biocompatible hydrogel polymer, the longer is its lifetime in the body. In further instances, the electron density at the carbonyl of the ester unit controls the lifetime of the hydrogel polymer in the body. In certain instances, biocompatible hydrogel polymers without ester groups are essentially not biodegradable. In additional instances, the molecular weight of the first and second compounds controls the lifetime of the hydrogel polymer in the body. In further instances, the number of ester groups per gram of polymer controls the lifetime of the hydrogel polymer in the body.

In some instances, the lifetime of the hydrogel polymer can be estimated using a model, which controls the temperature and pH at physiological levels while exposing the hydrogel polymer to a buffer solution. In certain instances, the biodegradation of the hydrogel polymer is substantially non-enzymatic degradation.

In some embodiments, the selection of reaction conditions determines the degradation time of the hydrogel polymer. In certain embodiments, the concentration of the first compound and second compound monomers determines the degradation time of the resulting hydrogel polymer. In some instances, a higher monomer concentration leads to a higher degree of cross-linking in the resulting hydrogel polymer. In certain instances, more cross-linking leads to a later degradation of the hydrogel polymer.

In certain embodiments, the composition of the linker in the first and/or second compound influences the speed of degradation of the resulting hydrogel polymer. In some embodiments, the more ester groups are present in the hydrogel polymer, the faster the degradation of the hydrogel polymer. In certain embodiments, the higher the concentration of mercaptopropionate (ETTMP), acetate amine (AA), glutarate or succinate (SG or SS) monomers, the faster the rate of degradation.

Wound Patch or Joint Spacer in the Treatment of Veterinary Disease

In some embodiments, the pre-formulation described herein is delivered to a target site on or in an animal. In certain embodiments, the pre-formulation is delivered to a target site in a joint. In some embodiments, the pre-formulation forms a biocompatible hydrogel polymer inside a joint. In certain embodiments, the pre-formulation forms a sticky biocompatible polymer to seal a wound on or in an animal. In some embodiments, the pre-formulation forms a suture. In certain embodiments, the wound patch, joint spacer, or suture gels at least in part at the target site in or on the animal. In some embodiments, the wound patch, joint spacer, or suture polymerizes at least in part at a target site. In some embodiments, the wound patch, joint spacer, or suture adheres at least partially to the target site.

In certain embodiments, the pre-formulation is used as a "liquid suture" or as a drug delivery platform to transport medications directly to the targeted site in or on the animal or human. In some embodiments the target site is a joint, a wound or the navicular bone. In some embodiments, the spreadability, viscosity, optical clarity, and adhesive properties of the pre-formulation are optimized to create materials ideal as liquid sutures for the treatment of veterinary diseases. In certain embodiments, the gel time is controlled from 50 seconds to 15 minutes.

In some embodiments, a method of treating wounds of a mammal by delivering a liquid polyglycol-based, fully synthetic, biocompatible formulation formed by adding a liquid component to the solid polyglycol-based, fully synthetic, pre-formulation to a target site of the wound of the mammal, wherein the liquid polyglycol-based, fully synthetic, biocompatible formulation gels at the target site of the wound. In another aspect, provided herein, is a method of treating arthritis in a mammal by delivering a liquid polyglycol-based, fully synthetic, biocompatible hydrogel polymer formed by adding a liquid component to the solid polyglycol-based, fully synthetic, pre-formulation into a target site in a joint space, wherein the liquid polyglycol-based, fully synthetic, biocompatible formulation gels at the target site in the joint space. In some embodiments, the mammal is a human. In other embodiments, the mammal is an animal. In a further aspect, provided herein is a method of treating navicular disease in a horse by delivering a liquid polyglycol-based, fully synthetic, biocompatible formulation formed by adding a liquid component to the solid polyglycol-based, fully synthetic, pre-formulation to a target site in a hoof of the horse, wherein the liquid polyglycol-based, fully synthetic, biocompatible formulation gels at the target site in the hoof of the horse.

In some embodiments, a method of treating wounds of a mammal by delivering a liquid biocompatible formulation formed by adding a liquid component to the solid pre-formulation to a target site of the wound of the mammal, wherein the liquid biocompatible formulation gels at the target site of the wound. In another aspect, provided herein, is a method of treating arthritis in a mammal by by delivering a liquid biocompatible hydrogel polymer formed by adding a liquid component to the solid pre-formulation into a target site in a joint space, wherein the liquid biocompatible formulation gels at the target site in the joint space. In some embodiments, the mammal is a human. In other embodiments, the mammal is an animal. In a further aspect, provided herein is a method of treating navicular disease in a horse by delivering a liquid, biocompatible formulation formed by adding a liquid component to the solid pre-formulation to a target site in a hoof of the horse, wherein the liquid biocompatible formulation gels at the target site in the hoof of the horse.

Control of Release Rate of a Therapeutic Agent

In some embodiments, the biocompatible hydrogel polymer slowly delivers a therapeutic agent to a target site by diffusion and/or osmosis over time ranging from hours to days. In certain embodiments, the drug is delivered directly to the target site. In some embodiments, the procedure of delivering a biocompatible hydrogel polymer comprising a therapeutic agent to a target site is repeated several times, if needed. In other embodiments, the therapeutic agent is released from the biocompatible hydrogel polymer through biodegradation of the hydrogel polymer. In some embodiments, the therapeutic agent is released through a combination of diffusion, osmosis, and/or hydrogel degradation mechanisms. In certain embodiments, the release profile of the therapeutic agent from the hydrogel polymer is unimodal. In some embodiments, the release profile of the therapeutic agent from the hydrogel polymer is bimodal. In certain embodiments, the release profile of the therapeutic agent from the hydrogel polymer is multimodal.

In some embodiments, the therapeutic agent is released from the biocompatible hydrogel polymer though diffusion or osmosis. In certain embodiments, the therapeutic agent is substantially released from the biocompatible hydrogel polymer within 180 days. In some embodiments, the therapeutic agent is substantially released from the biocompatible hydrogel polymer within 14 days. In certain embodiments, the therapeutic agent is substantially released from the biocompatible hydrogel polymer within 24 hours. In some embodiments, the therapeutic agent is substantially released from the biocompatible hydrogel polymer within one hour. In certain embodiments, the therapeutic agent is substantially released from the biocompatible hydrogel polymer within about 180 days, about 150 days, about 120 days, about 90 days, about 80 days, about 70 days, about 60 days, about 50 days, about 40 days, about 35 days, about 30 days, about 28 days, about 21 days, about 14 days, about 10 days, about 7 days, about 6 days, about 5 days, about 4 days, about 3 days, about 2 days, about 1 day, about 0.5 day, about 6 hours, about 4 hours, about 2 hours, about or 1 hour. In some embodiments, the therapeutic agent is substantially released from the biocompatible hydrogel polymer within more than 180 days, more than 150 days, more than 120 days, more than 90 days, more than 80 days, more than 70 days, more than 60 days, more than 50 days, more than 40 days, more than 35 days, more than 30 days, more than 28 days, more than 21 days, more than 14 days, more than 10 days, more than 7 days, more than 6 days, more than 5 days, more than 4 days, more than 3 days, more than 2 days, more than 1 day, more than 0.5 day, more than 6 hours, more than 4 hours, more than 2 hours, more than or 1 hour. In certain embodiments, the therapeutic agent is substantially released from the biocompatible hydrogel polymer within less than 180 days, less than 150 days, less than 120 days, less than 90 days, less than 80 days, less than 70 days, less than 60 days, less than 50 days, less than 40 days, less than 35 days, less than 30 days, less than 28 days, less than 21 days, less than 14 days, less than 10 days, less than 7 days, less than 6 days, less than 5 days, less than 4 days, less than 3 days, less than 2 days, less than 1 day, less than 0.5 day, less than 6 hours, less than 4 hours, less than 2 hours, less than or 1 hour. In some embodiments, the therapeutic agent is substantially released from the biocompatible hydrogel polymer within about one day to about fourteen days. In certain embodiments, the therapeutic agent is substantially released from the biocompatible hydrogel polymer within about one day to about 70 days.

In some embodiments, the therapeutic agent is a biomolecule and the release of the biomolecule from the hydrogel polymer is controlled by the composition of the hydrogel polymer. In certain embodiments, the biomolecule is released when the hydrogel polymer starts to degrade. In some embodiments, the pore size of the hydrogel polymer is small enough to prevent the early phase release of the biomolecule (i.e., release before the degradation of the hydrogel polymer). In certain embodiments, the pore size of the hydrogel polymer is large enough to allow the early phase release of the biomolecule. In some embodiments, the ratio of the pore size of the hydrogel polymer to the size of the biomolecule determines the release rate of the biomolecule.

Exemplary Antibacterials

In some embodiments, the pre-formulation comprises an antibacterial agent as the therapeutic agent. In some embodiments, the pre-formulation comprises an antiseptic agent. An antibacterial agent is defined as an agent that inhibits the reproduction and growth of bacteria, and include antiseptics. In certain embodiments, the antiseptic agent is an alcohol, an aldehyde, a halogen-releasing compound, or a peroxide. In other embodiments, the antiseptic agent is an anilide, a biguanide, a bisphenol, a halophenol, a heavy metal, a phenol, a cresol or a quaternary ammonium compound. Examples of antiseptics include, but are not limited to, Alchols like ethanol and isopropyl alchol; Aldehydes like glutaraldehyde and formaldehyde, Halogen releasing compounds like chlorine compounds and iodine compounds; Peroxides like hydrogen peroxide, ozone, peracetic acid; Biguanides, like chlorhexidine, alexidine, and polymeric biguanides; Bisphenols like triclosan and hexachlorophene; Heavy metals like silver compounds and mercury compounds; Quaternary ammonium compounds like benzalknoium chloride, cetrimide, methylbenzethonium chloride, benzethonium chloride, cetaalkonium chloride, cetylpyridinium chloride, and dofanium chloride.

Exemplary Antifungals

In some embodiments, the pre-formulation comprises an antifungal agent as the therapeutic agent. In certain embodiments, the antifungal agent is a polyene antifungal, an imidazole, triazole, or thiazole antifungal, a triazole antifungal, a thiazole antifungal, an allylamine derivative, or an echinocandin derivative. Examples of antifungal agents include, but are not limited to, Polyene derivatives like natamycin, rimocidin, filipin, nystatin, amphotericin B, candicin, hamycin; Imidazole derivatives like miconazole, ketoconazole, clotrimazole, econazole, omoconazole, bifonazole, butoconazole, fenticonazole, isoconazole, oxiconazole, sertaconazole, sulconazole, tioconazole; Tetrazole derivatives like fluconazole, itraconazole, isavuconazole, posaconazole, voriconzaole, terconazole, albaconazole; Thiazole derivatives like abafungin; Allylamine derivative like terbifine, naftifine, butenafine; Echinocandin derivatives like anidulafungin, caspofungin, micafungin; Other antifungals like polygodial, benzoic acid, ciclopirox, tonaftate, undecylenic acid, flycytosine, griseofulvin, haloprogin, sodium bicarbonate, pirctone olamine, zinc pyrithione, selenium sulfide, tar, or tea tree oil.

Exemplary Antibiotics

In some embodiments, the pre-formulation comprises an antibiotic. In certain embodiments, the antibiotic agent is a aminoglycoside, ansamycin, carbacephem, carbapenem, cephalosporin, glycopeptide, lincosamide, lipopeptide, macrolide, monobactam, nitrofurans, penicillin, polypeptide, quinolone, sulfonamide, or tetracycline. Examples of antibiotic agents include, but are not limited to, Aminoglycoside derivatives like amikacin, gentamicin, kanamycin, neomycin, netilmicin, tobramicin, paromomycin; Ansamycin derivatives like geldanamycin, herbimycin; Carbacephem derivatives like loracarbef, Carbapenem derivatives like ertapenem, doripenem, imipenem, meropenem; Cephalosporin derivatives like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; Glycopeptide derivatives like teicoplanin, vancomycin, telavancin; Lincosamides like clindamycin, lincomycin; Lipopeptide derivatives like daptomycin; Macrolide derivatives like azithromycin, clarithromycin, dirithromycin, erythromycin, roxithromycin, troleandomycin; telithreomycin, spectinomycin; Monobactam derivatives like aztreonam; Nitrofuran derivatives like furazolidone, nitrofurantoin; Penicillin derivatives like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; Penicillin combinations like amoxicillin/clavulanate, ampicillin/sulbactam, piperacillin/tazobactam, ticarcillin/clavulanate; Polypeptide derivatives like bacitracin, colistin, polymyxin B; Quinolone derivatives like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, danofloxacin, difloxacin, enrofloxacin, ibafloxacin, marbofloxacin, orbifloxacin, sarafloxacin; Sulfonamide derivatives like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; Tetracyclin derivatives like demeclocycline, doxycycline, minocycline, oxytetracycline, tetracycline; Derivatives against mycobacteria like clofazimine, dapsone, capreomycin, cycloserine, ethambutol, ethioamide, isoniazid, pyrazinamide, rifampin, refampicin, rifabutin, rifapentine, streptomycin; or other antibiotic agents like arsphenamine, chloramphenicol, fosfomycin, fusidic acid, linezolid, metronidazole, mupirocin, platensimycin, quinupristin/dalfopristin, rifaximin, thiampheniol, tigecycline, tinidazole.

Exemplary Antiviral Agents

In some embodiments, the pre-formulation comprises an antiviral agent. In certain embodiments, the antiviral agent is a nucleoside reverse transcriptase inhibitor, a non-nucleoside reverse transcriptase inhibitor, a fusion inhibitor, an integrase inhibitor, a nucleoside analog, a protease inhibitor, a reverse transcriptase inhibitor. Examples of antiviral agents include, but are not limited to, abacavir, aciclovir, acyclovir, adefovir, amantadine, amprenavir, ampligen, arbidol, atazanavir, boceprevir, cidofovir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, interferon, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir (Valtrex), valganciclovir, vicriviroc, vidarabine, viramidine, zalcitabine, zanamivir, zidovudine.

Exemplary Immunosuppressive Agents

In some embodiments, the pre-formulation comprises an immunosuppressive agent. In certain embodiments, the immunosuppressive agent is a calcinuerin inhibitor, mTor inhibitor, an anti-proliferative agent (e.g., an alkylating agent or an antimetabolite), a glucocorticosteroid, an antibody, or an agent acting on immunophilins. Examples of immunosuppressive agents include, but are not limited to, Calcineurin inhibitors like ciclosporin, tacrolimus; mTOR inhibitors like sirolimus, everolimus; Anti-proliferatives like azathioprine, mycophenolic acid; Corticosteroids like prednisolone, hydrocortisone; Monoclonal anti-IL-2Rα receptor antibodies like basiliximab, daclizumab; Polyclonal anti-T-cell antibodies like anti-thymocyte globulin (ATG), anti-lymphocyte globulin (ALG); Monoclonal anti-CD20 antibodies like rituximab; Interleukin inhibitors like daclizumab, basiliximab, anakinra, rilonacept, ustekinumab, mepolizumab, tocilizumab, canakinumab, briakinumab; Tumor necrosis factor alpha (TNF-α) inhibitors like etanercept, infliximab, afelimomab, adalimumab, certolizumab pegol, golimumab; Selective immunosuppressants like muromonab-CD3, anti-lymphocyte immunoglobulin (horse), antithymocyte immunoglobulin (rabbit), mycophenolic acid, sirolimus, leflunomide, alefacept, everolimus, gusperimus, efalizumab, abetimus, natalizumab, abatacept, eculizumab, belimumab, fingolimod, belatacept; or Other immunosuppressants like azathioprine, thalidomide, methotrexate, lenalidomide Exemplary Hemostasis Agents In some embodiments, the pre-formulation comprises a hemostasis agent (or antihemorrhagic agent). In certain embodiments, the hemostasis agent is an antifibrinolytic (amino acid or proteinase inhibitor), a vitamin K, fibrinogen, a local hemostatic, or a blood coagulation factor. Examples of hemostasis agents include, but are not limited to, Amino acids like aminocaproic acid, tranexamic acid, aminomethylbenzoic acid; Proteinase inhibitors like aprotinin, alfal antitrypsin, Cl-inhibitor, camostat; Vitamin K like phytomenadione, menadione; Fibrinogen like Human fibrinogen; Local hemostatics like absorbable gelatin sponge, oxidized cellulose, tetragalacturonic acid hydroxymethylester, adrenalone, thrombin, collagen, calcium alginate, epinephrine, human fibrinogen; Blood coagulation factors like coagulation factor IX, II, VII and X in combination, coagulation factor VIII, factor VIII inhibitor bypassing activity, coagulation factor IX, coagulation factor VII, von Willebrand factor and coagulation factor VIII in combination, coagulation factor XIII, eptacog alfa, nonacog alfa, thrombin; Other systemic hemostatics like etamsylate, carbazochrome, batroxobin, romiplostim, eltrombopag.

Exemplary Anti Inflammatory Agents

In some embodiments, the pre-formulation comprises an anti-inflammatory agent. In certain embodiments, the anti-inflammatory agent is a non-steroidal anti-inflammatory agent. In other embodiments, the anti-inflammatory agent is a glucocorticosteroid. In some embodiments, the non-steroidal anti-inflammatory agent is a butylpyrazolidine, an acetic acid derivative, oxicam, propionic acid derivative, fenamate, or coxib. Examples of anti-inflammatory agents include, but are not limited to, Butylpyrazolidines like phenylbutazone, mofebutazone, oxyphenbutazone, clofezone, kebuzone; Acetic acid derivatives and related substances like indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, indometacin combinations, diclofenac combinations; Oxicams like piroxicam, tenoxicam, droxicam, lornoxicam, meloxicam; Propionic acid derivatives like ibuprofen, naproxen, ketoprofen, fenoprofen, fenbufen, benoxaprofen, suprofen, pirprofen, flurbiprofen, indoprofen, tioprofenoic acid, oxaprozin, ibuproxam, dexibuprofen, flunoxaprofen, alminoprofen, dexketoprofen, naproxcinod; Fenamates like mefenamic acid, tolfenamic acid, flufenamic acid, meclofenamic acid; Coxibs like celecoxib, rofecoxib, valdecoxib, parecoxib, etoricoxib, lumiracoxib; Other antiinflammatory and antirheumatic agents like nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate; Corticosteroids like the Mineralocorticoids aldosterone, fludrocortisones, desoxycortone, and the Glucocorticoids betamethasone, dexamethasone, fluocortolone, methylprednisolone, paramethasone, prednisolone, prednisone, triamcinolone, hydrocortisone, cortisone, prednylidene, rimexolone, deflazacort, cloprednol, meprednisone, cortivazol.

Exemplary Bisphosphonates

In some embodiments, the pre-formulation comprises a bisphosphonate. Examples of bisphosphonates include, but are not limited to, etidronic, clodronic acid, pamidronic acid, alendronic acid, tiludronic acid, ibandronic acid, risedronic acid, zoledronic acid.

Exemplary Analgesics and Anesthetics

In some embodiments, the pre-formulation comprises an analgesic or anesthetic agent. In certain embodiments, the analgesic or anesthetic agent comprises paracetamol, an opiate, diproqualone, phenazone, cocaine, or lidocaine. In certain embodiments, the opioid is a natural opium alkaloid, phenylpiperidine derivative, diphenylpropylamine derivative, benzomorphan derivative, oripavin derivative, or morphinan derivative. In some embodiments, the analgesic is a salicylic acid derivative, pyrazolone, or anilide. In other embodiments, the analgesic is an ergot alkaloid, corticosteroid derivative, or selective serotonin (5HT1) agonist. Examples of local anesthetics include, but are not limited to, Esters of aminobenzoic acid like metabutethamine, procaine, tetracaine, chloroprocaine, benzocaine; Amides like bupivacaine, lidocaine, mepivacaine, prilocaine, butanilicaine, cinchocaine, etidocaine, articaine, ropivacaine, levobupivacaine, tetracaine, chloroprocaine, benzocaine; Esters of benzoic acid like cocaine; Other local anesthetics like ethyl chloride, dyclonine, phenol, capsaicin.

Exemplary Proteins, Biomolecules, and Other Therapeutic Agents

In some embodiments, the pre-formulation comprises a protein or other biomolecule. Examples of proteins and other biomolecules include, but are not limited to abarelix, abatacept, acarbose, adalimumab, alglucosidase alfa, Antihemophilic Factor Recombinant, antithrombin recombinant lyophilized powder for reconstitution, belatacept, belimumab, bevacizumab, botulinum toxin type A, canakinumab, certolizumab pegol, Cetrotide, cetuximab, chorionic human recombinant gonadotropin, coagulation Factor IX (recombinant), collagenase clostridium histolyticum, conjugated estrogens, Cyanocobalamin, darbepoetin alfa, denosumab, Diphtheria and Tetanus Toxoids and Acellular Pertussis Vaccine Adsorbed, Diptheria and Tetanus Toxoids and Acellular Pertussis Vaccine Absorbed, dornase alfa, drotrecogin alfa [activated]), ecallantide, eculizumab, enfuvirtide, enoxaparin sodium, epoetin alfa, etanercept, exenatide, filgrastim, follitropin alfa, follitropin beta, Fragmin, galsulfase, gemtuzumab ozogamicin, glatiramer acetate, Glucagon, golimumab, goserelin acetate, Haemophilus b Conjugate Vaccine—Tetanus Toxoid Conjugate, histrelin acetate, ibritumomab tiuxetan, idursulfase, incobotulinumtoxin A, infliximab, Influenza Virus Vaccine, insulin derivatives, insulin aspart, insulin glargine [rDNA origin], insulin lispro, interferon alfacon-1, interferon beta-1a, Interferon beta-1b, ipilimumab, Japanese Encephalitis Vaccine—Inactivated—Adsorbed, lanreotide acetate, laronidase, leuprolide acetate for depot suspension, leuprolide acetate, linagliptin, liraglutide, mecasermin, menotropins, methoxy polyethylene glycol-epoetin beta, natalizumab, ofatumumab, omalizumab, onabotulinumtoxin A, palivizumab, pancrelipase, pancrelipase, panitumumab, pegaptanib, pegfilgrastim, peginterferon alfa-2a, peginterferon alfa-2b, pegloticase, pegvisomant, pentosan polysulfate sodium, pramlintide, quadrivalent human papillomavirus (types 6, 11, 16, 18) recombinant vaccine, ranibizumab, rasburicase, Recombinant Human Papillomavirus Bivalent (Types 16 and 18) Vaccine, recombinant Interferon alfa-2b, reteplase, Rituximab, romiplostim, sargramostim, secretin, sevelamer carbonate, sevelamer hydrochloride, sipuleucel-T, somatropin, somatropin [rDNA origin], teriparatide, tocilizumab, trastuzumab, triptorelin pamoate, ustekinumab, velaglucerase alfa for injection.

In certain embodiments, the pre-formulation comprises a protein as a pharmaceutically active biomolecule. Examples of proteins include, but are not limited to, octreotide, eptifibatide, desmopressin, leuprolide/leuprorelin, goserelin, ciclosporin, bivalirudin, glucagon, calcitonin, teriparatide, enfuvirtide, ecallantide, romiplostim. In some embodiments, the pre-formulation comprises a recombinant protein as a pharmaceutically active biomolecule. Examples of recombinant proteins include, but are not limited to, insulin, lepirudin, somatropin, aldesleukin, interferon gamma 1b, anakinra, interferon alpha 2b, interferon beta 1b, interferon beta 1a, PEG interferon alpha 2a, filgrastim, pegfilgrastim, oprelvekin, reteplase, denileukin diftitox, follitropin alfa, recFSH, thyrotropin alfa, imiglucerase, becaplermin, sargramostim, darbepoetin, erythropoietin, DNAse, Factor VIIa, Factor IX, Factor XIII, drotrecogin, alteplase, tenecteplase, moroctocog alfa (BDDrFVIII), Factor VIII-2, Factor VIII, peginteferon, ribavarin, clostridial collagenese, alglucosidase alpha2, incobotulinumtoxina, pegloticase, palifermin, galsulfase, idursulfase. In certain embodiments, the biocompatible hydrogel polymer comprises an antibody as a pharmaceutically active biomolecule. Examples of antibodies include, but are not limited to, etanercept, abciximab, gemtuzumab, rituximab, adalimumab, palivizumab, trastuzumab, bevacizumab, natalizumab, omalizumab, infliximab, alemtuzumab, efalizumab, cetuximab, golimumab, abobotulinumtoxina, canakinumab, ustekinumab, ofatumumab, certolizumab pegol, tocilizumab, denosumab, abatacept, ranibizumab, panitumumab, eculizumab, brentixumab, iplimumab, belimumab, rilonacept.

In some embodiments, the pre-formulation comprises other therapeutic agents. Examples of other therapeutic agents include, but are not limited to, stem cells and gallium nitrate. Futhermore, other therapeutic agents also include bitterants or aversive agents, which can be used to prevent accidental ingestion. Examples of bitterants include denatonium, sucrose octaacetate, brucine, and quassin.

Exemplary Lubricity Agents

In certain embodiments, the pre-formulation comprises a lubricity agent. Lubricity agents, or lubricants, are defined as substances that reduce the friction between moving surfaces. In some embodiments, lubricity agents reduce the friction between joints. In specific embodiments, the lubricity agent is hyaluronic acid. Other examples of lubricity agents, include glucosamine, chondroitin, methylsulfonylmethane (MSM), omega-3-fatty acids, hyaluronic acid, and shark cartilage.

EXAMPLES

The following specific examples are to be construed as merely illustrative, and not limitative of the remainder of the disclosure in any way whatsoever.

The following general characteristics of the monomers and polymers are needed to be successful for bonding to the skin without causing any adverse effects.

| Monomers Property | Characteristics |
| --- | --- |
| 1 In vivo polymerizable | Could be polymerized inside mammalian cavity or over the skin |
| 2 Reaction mixture pH | Physiological to 8.0 pH range |
| 3 Reaction temperature | Ambient to body temperature |
| 4 Formulation physical form | Two or three component system; Mixed immediately prior to use, may contain radiopaque agent such as barium sulphate or iodine containing organic compounds or other known radiopaque agents |
| 5 Mixing time for the reaction to start | Few seconds (~10 sec) |
| 6 Gel formation time | Gel formation time ranges from 10 seconds to 120 seconds, or could be as long as 30 minutes depending on the application |
| 7 Solution viscosity | Solution viscosity ranges from 1 to 800 cps |
| 8 Sterilization capability | ETO to E-beam sterilizable |
| 9 Localized delivery | Ideal for localized delivery for small molecules, large molecules and cells |
| 10 Stability of drugs in formulation mixture | All small molecule drugs and proteins studied so far have been found to be stable |

Below are some adhesive polymer characteristics.

| | Adhesive Property | Characteristics |
| --- | --- | --- |
| 1 | Tissue adhesion | Sticky formulations, physicochemical characteristics ideal for bonding to skin, bones, or other mammalian tissues |
| 2 | Polymer hardness | Can be controlled from soft tissues to harder cartilage like materials |
| 3 | Bioabsorption Time | About 2 weeks up to 10 years, or totally non-bioabsorbable |
| 4 | Biocompatibility | Highly biocompatible; passed all the subjected ISO 10993 tests |
| 5 | Polymer cytotoxicity | Non-cytotoxic formulations |
| 6 | Small molecule elution | Small drug molecules elution can be controlled and thus pharmaceutical drugs could also be delivered using the formulations, if needed |
| 7 | Compatibility with proteins and Cells | Highly compatible due to physiological pH of the polymers |

For applications on-site, desired gel times are under 120 seconds. Additionally, the viscosity should be high enough to prevent excessive spreading around the target treatment area, but low enough to enter any small cavities at the site. Furthermore, the reaction buffers should be close to physiological conditions. The desired degradation time and polymer pore size will vary based on the application. The polymer should be elastic and strong enough to resist fragmentation in the body.

The chemical components of the polymers are listed in Table 1. The chemical monomers will be referred to by their abbreviations. All materials were stored and handled at 20° C. unless specified. Several USP grade viscosity enhancing agents were purchased from Sigma-Aldrich and were stored at 25° C. They include methylcellulose (Methocel® MC, 10-25MPA·S) abbreviated as MC; hypromellose (hydroxypropylmethylcellulose 2910) abbreviated as HPMC; and povidone K-30 (polyvinylpyrrolidone) abbreviated as PVP. The 2% chlorhexidine solution was stored at 5° C. and allowed to warm to room temperature before use, which typically took 30 minutes. The monomers were stored at 5° C. and allowed to warm to room temperature before use, which typically took 30 minutes. After use the contents were purged with $N_2$ for approximately 30 seconds before sealing with parafilm and returning to 5° C. Alternately, the monomers were stored at −20° C. and allowed to warm to room temperature before use under the flow of inert gas, which typically took 30 minutes. The monomers were purged with inert gas for at least 30 seconds before returning to −20° C.

The indicating silica gel and oxygen absorbing packets from IMPAK were stored in vacuum-sealed foil pouches. After use, any remaining packets were resealed in fresh pouches. The oxygen absorbers were sealed with a color changing oxygen indicator tablet. The viability of the materials was checked before each use by observing the color of the silica gel and the oxygen indicator tablet.

A 0.15 M phosphate buffer was made by dissolving 9.00 g (0.075 mol) $NaH_2PO_4$ in 500 mL of distilled water at 25° C. with magnetic stirring. The pH was then adjusted to 7.99 with the dropwise addition of 50% aqueous NaOH. Several other phosphate buffers were prepared in a similar fashion: 0.10 M phosphate at pH 9, 0.10 M phosphate at pH 7.80, 0.10 M phosphate at 7.72, 0.10 M phosphate at pH 7.46, 0.15 M phosphate at pH 7.94, 0.15 M phosphate at pH 7.90, 0.4 M phosphate at pH 9, and 0.05 M phosphate at pH 7.40.

A sterile 0.10 M phosphate buffer at pH 7.58 with 0.30% HPMC was prepared for use in kits. First, 1.417 g HPMC was dissolved in 471 mL of 0.10 M phosphate buffer at pH 7.58 by vigorous shaking. The viscous solution was allowed to clarify overnight. The solution was filtered through a 0.22 μm filter (Corning #431097) with application of light vacuum. The viscosity of the resulting solution was measured to be 8.48 cSt+/−0.06 at 20° C.

A sterile 0.10 M phosphate buffer at pH 7.58 with 0.3% HPMC was prepared. First, a 0.10 M phosphate buffer was made by dissolving 5.999 g (0.05 mol) of $NaH_2PO_4$ in 500 mL of distilled water at 20° C. with magnetic stirring. The pH was then adjusted to 7.58 with the dropwise addition of 50% aqueous NaOH. Then, 1.5 g of HPMC was dissolved in 500 mL of the above buffer solution by vigorous shaking. The viscous solution was allowed to clarify overnight. The solution was filtered through a 0.22 μm filter (Corning #431097) with application of light vacuum. The viscosity of the resulting solution was measured via the procedure as described in the Viscosity Measurements section and was found to be 8.48 cSt+/−0.06 at 20° C.

Phosphate buffered saline (PBS) was prepared by dissolving two PBS tablets (Sigma Chemical, P4417) in 400 mL of distilled water at 25° C. with vigorous shaking. The solution has the following composition and pH: 0.01 M phosphate, 0.0027 M potassium chloride, 0.137 M sodium chloride, pH 7.46.

A 0.058 M phosphate buffer was made by dissolving 3.45 g (0.029 mol) of $NaH_2PO_4$ in 500 mL of distilled water at 25° C. with magnetic stirring. The pH was then adjusted to 7.97 with the dropwise addition of 50% aqueous NaOH.

A 0.05 M borate buffer was made by dissolving 9.53 g (0.025 mol) of $Na_2B_4O_7 \cdot 10 H_2O$ in 500 mL of distilled water at 25° C. with magnetic stirring. The pH was then adjusted to 7.93 or 8.35 with the dropwise addition of 6.0 N HCl.

An antiseptic liquid component was prepared in a similar fashion with a commercial 2% chlorhexidine solution. To 100 mL of 2% chlorhexidine solution was dissolved 0.3 g of HPMC. The viscous solution was allowed to clarify overnight at 5° C. The resulting clear blue solution has the following composition: 2% chlorhexidine, 0.3% HPMC and an unknown quantity of nontoxic blue dye and detergent.

Other liquid components were prepared in a similar fashion by simply dissolving the appropriate amount of the desired additive to the solution. For example, an antiseptic liquid component with 1% denatonium benzoate, a bittering agent, was prepared by dissolving 2 g of denatonium benzoate in 200 mL of 2% chlorhexidine solution.

Alternatively, commercially available drug solutions were used as the liquid component. For example, saline solution, Kenalog-10 (10 mg/mL solution of triamcinolone acetonide) and Depo-Medrol (40 mg/mL of methylprednisolone acetate) were used.

The amine or thiol component (typically in the range of 0.1 mmol arms equivalents) was added to a 50 mL centrifuge tube. A volume of reaction buffer was added to the tube via a pipette such that the final concentration of solids in solution was about 5 percent. The mixture was gently swirled to dissolve the solids before adding the appropriate amount of ester or epoxide. Immediately after adding the ester or epoxide, the entire solution was shaken for 10 seconds before letting it rest.

The gel time for all cases was measured starting from the addition of the ester or epoxide until the gelation of the solution. The gel point was noted by pipetting 1 mL of the reaction mixture and observing the dropwise increase in viscosity. Degradation of the polymers was performed by the addition of 5 to 10 mL of phosphate buffered saline to ca. 5 g of the material in a 50 mL centrifuge tube and incubating the mixture at 37° C. The degradation time was measured starting from the day of addition of the phosphate buffer to complete dissolution of the polymer into solution.

TABLE 1

Components used in formulations.

| Components | Technical Name |
|---|---|
| ETTMP-1300 | Ethoxylated trimethylolpropane tri(3-mercaptopropionate) |
| 4ARM-5k-SH | 4ARM PEG Thiol (pentaerythritol) |
| 4ARM-2k-NH2 | 4ARM PEG Amine (pentaerythritol), HCl Salt, MW 2000 |
| 4ARM-5k-NH2 | 4ARM PEG Amine (pentaerythritol), HCl Salt, MW 5000 |
| 8ARM-20k-NH2 | 8ARM PEG Amine (hexaglycerol), HCl Salt, MW 20000 |
| 4ARM-20k-AA | 4ARM PEG Acetate Amine HCl Salt, MW 20000 |
| 8ARM-20k-AA | 8ARM PEG Acetate Amine (hexaglycerol) HCl Salt, MW 20000 |
| 8ARM-20k-AA | 8ARM PEG Acetate Amine (hexaglycerol) TFA Salt, MW 20000 |
| 4ARM-10k-SG | 4ARM PEG Succinimidyl Glutarate (pentaerythritol), MW 10000 |
| 8ARM-15k-SG | 8ARM PEG Succinimidyl Glutarate (hexaglycerol), MW 15000 |
| 4ARM-20k-SGA | 4ARM PEG Succinimidyl Glutaramide (pentaerythritol), MW 20000 |
| 4ARM-10k-SS | 4ARM PEG Succinimidyl Succinate (pentaerythritol), MW 10000 |
| EJ-190 | Sorbitol polyglycidyl ether |
| MC | Methyl Cellulose (Methocel ® MC) |
| HPMC | Hypromellose (Hydroxypropylmethylcellulose) |
| PVP | Povidone (polyvinylpyrrolidone) |

Example 1

Manufacture of Hydrogel (Amine-Ester Chemistry)

A solution of 8ARM-20K-NH2 was prepared in a Falcon tube by dissolving about 0.13 g solid monomer in about 2.5 mL of sodium phosphate buffer (buffer pH 7.36). The mixture was shaken for about 10 seconds at ambient temperature until complete dissolution was obtained. The Falcon tube was allowed to stand at ambient temperature. In another Falcon tube, 0.10 g of 8ARM-15K-SG was dissolved in the same phosphate buffer as above. The mixture was shaken for about 10 seconds and at this point all the powder dissolved. The 8ARM-15K-SG solution was poured immediately into the 8ARM-20K-NH2 solution and a timer was started. The mixture was shaken and mixed for about 10 seconds and a 1 mL solution of the mixture was pipetted out using a mechanical high precision pipette. The gel time of 1 mL liquid was collected and then verified with the lack of flow for the remaining liquids. The gel time data of the formulation was recorded and was about 90 seconds.

Example 2

Manufacture of Hydrogel (Amine-Ester Chemistry)

A solution of amines was prepared in a Falcon tube by dissolving about 0.4 g solid 4ARM-20k-AA and about 0.2 g solid 8ARM-20k-NH2 in about 18 mL of sodium phosphate buffer (buffer pH 7.36). The mixture was shaken for about 10 seconds at ambient temperature until complete dissolution was obtained. The Falcon tube was allowed to stand at ambient temperature. To this solution, 0.3 g of 8ARM-15K-SG was added. The mixture was shaken to mix for about 10 seconds until all the powder dissolved. 1 mL of the mixture was pipetted out using a mechanical high precision pipette. The gel time of the formulation was collected using the process described above. The gel time was about 90 seconds.

Example 3

Manufacture of Hydrogel (Thiol-Ester Chemistry

A solution of ETTMP-1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.20 g of 8ARM-15K-SG was added. The mixture was shaken for about 10 seconds until the powder dissolved. 1 mL of the mixture was pipetted out using a mechanical high precision pipette. The gel time was found to be about 70 seconds.

Example 4

Manufacture of Hydrogel (Thiol-Epoxide Chemistry)

A solution of ETTMP-1300 was prepared in a Falcon tube by dissolving about 0.04 g monomer in about 5 mL of sodium borate buffer (buffer pH 8.35). The mixture was shaken for about 10 seconds at ambient temperature until complete dissolution was obtained. The Falcon tube was allowed to stand at ambient temperature. To this solution, 0.10 g of EJ-190 was added. The mixture was shaken for about 10 seconds until complete dissolution is obtained. 1 mL of the mixture was pipetted out using a mechanical high precision pipette. The gel time was found to be about 6 minutes.

Example 5

In vitro Bioabsorbance Testing

A 0.10 molar buffer solution of pH 7.40 was prepared with deionized water. A 50 mL portion of this solution was transferred to a Falcon tube. A sample polymer was prepared in a 20 cc syringe. After curing, a 2-4 mm thick slice was cut from the polymer slug and was placed in the Falcon tube. A circulating water bath was prepared and maintained at 37° C. The Falcon tube with polymer was placed inside the water bath and time was started. The dissolution of the polymer was monitored and recorded. The dissolution time ranged from 1-90 days depending on the type of sample polymer.

Example 6

Gelling and Degradation Times of Amine-Ester Polymers

Amines studied were 8ARM-20k-NH2 and 4ARM-5k-NH2. The formulation details and material properties are given in Table 2. With 8ARM-20k-NH2, it was found that a phosphate buffer with 0.058 M phosphate and pH of 7.97 was necessary to obtain acceptable gel times of around 100 seconds. Using a 0.05 M phosphate buffer with a pH of 7.41 resulted in a more than two-fold increase in gel time (270 seconds).

With the 8ARM-20k-NH2, the ratio of 4ARM-10k-SS to 4ARM-20k-SGA was varied from 50:50 to 90:10. The gel time remained consistent, but there was a marked shift in degradation time around a ratio of 80:20. For formulations with ratios of 75:25 and 50:50, degradation times spiked to one month and beyond. Using lower amounts of 4ARM-20k-SGA (80:20, 85:15, 90:10) resulted in degradation times of less than 7 days.

As a comparison, the 4ARM-5k-NH2 was used in a formulation with a ratio of 4ARM-10k-SS to 4ARM-20k-SGA of 80:20. As was expected, the degradation time remained consistent, which suggests that the mechanism of degradation was unaffected by the change in amine. However, the gel time increased by 60 seconds, which may reflect the relative accessibility of reactive groups in a high molecular weight 8ARM amine and a low molecular weight 4ARM amine.

TABLE 2

Gel and degradation times for varying 4ARM-10k-SS/ 4ARM-20k-SGA ratios with 8ARM-15k-SG ester.

| Components | Ratio of 4ARM-10k-SS/4ARM-20k-SGA | Phosphate Reaction Buffer Concentration and pH | Gel Time (s) | Degradation Time (days) |
|---|---|---|---|---|
| 8ARM-20k-NH2 4ARM-10k-SS, 4ARM-20k-SGA | 50/50 | 0.05M pH 7.41 | 270 | N/A |
| 8ARM-20k-NH2 4ARM-10k-SS, 4ARM-20k-SGA | 50/50 | 0.058M pH 7.97 | 100 | >41 |
| 8ARM-20k-NH2 4ARM-10k-SS, 4ARM-20k-SGA | 75/25 | 0.058M pH 7.97 | 90 | 29 |
| 8ARM-20k-NH2 4ARM-10k-SS, 4ARM-20k-SGA | 80/20 | 0.058M pH 7.97 | 100 | 7 |
| 4ARM-5k-NH2 4ARM-10k-SS, 4ARM-20k-SGA | 80/20 | 0.058M pH 7.97 | 160 | 6 |
| 8ARM-20k-NH2 4ARM-10k-SS, 4ARM-20k-SGA | 85/15 | 0.058M pH 7.97 | 100 | 5 |
| 8ARM-20k-NH2 4ARM-10k-SS, 4ARM-20k-SGA | 90/10 | 0.058M pH 7.97 | 90 | 6 |

Example 7

Gelling and Degradation Times of Thiol-Ester Polymers

Thiols studied were 4ARM-5k-SH and ETTMP-1300. The formulation details and material properties are given in Table 3. It was found that a 0.05 M borate buffer with a pH of 7.93 produced gel times of around 120 seconds. Increasing the amount of 4ARM-20k-SGA in the formulation increased the gel time to 190 seconds (25:75 ratio of 4ARM-10k-SS to 4ARM-20k-SGA) up to 390 seconds (0:100 ratio of 4ARM-10k-SS to 4ARM-20k-SGA). Using a 0.05 M borate buffer with a pH of 8.35 resulted in a gel time of 65 seconds, about a two-fold decrease in gel time. Thus, the gel time may be tailored by simply adjusting the pH of the reaction buffer.

The ratio of 4ARM-10k-SS to 4ARM-20k-SGA was varied from 0:100 to 100:0. In all cases, the degradation time did not vary significantly and was typically between 3 and 5 days. It is likely that degradation is occurring via alternate pathways.

TABLE 3

Gel and degradation times for varying 4ARM-10k-SS/4ARM-20k-SGA ratios with 4ARM-5k-SH and ETTMP-1300 thiols.

| Components | Ratio of 4ARM-10k-SS/4ARM-20k-SGA | Phosphate Reaction Buffer Concentration and pH | Gel Time (s) | Degradation Time (days) |
|---|---|---|---|---|
| 4ARM-5k-SH 4ARM-10k-SS, 4ARM-20k-SGA | 50/50 | 0.05M pH 8.35 | 65 | N/A |
| 4ARM-5k-SH 4ARM-10k-SS, 4ARM-20k-SGA | 50/50 | 0.05M pH 7.93 | 120 | 4 |
| 4ARM-5k-SH 4ARM-10k-SS, 4ARM-20k-SGA | 75/25 | 0.05M pH 7.93 | 125 | 4 |
| 4ARM-5k-SH 4ARM-10k-SS, 4ARM-20k-SGA | 90/10 | 0.05M pH 7.93 | 115 | 4 |
| 4ARM-5k-SH 4ARM-10k-SS, 4ARM-20k-SGA | 25/75 | 0.05M pH 7.93 | 190 | 4 |
| 4ARM-5k-SH 4ARM-10k-SS, 4ARM-20k-SGA | 10/90 | 0.05M pH 7.93 | 200 | 4 |
| ETTMP-1300 4ARM-20k-SGA | 0/100 | 0.05M pH 7.93 | 390 | 3 |
| 4ARM-5k-SH 4ARM-10k-SS | 100/0 | 0.05M pH 7.93 | 120 | 4 |

Example 8

Gelling and Degradation Times of Amine-Ester and Thiol-Ester Polymers

An amine (4ARM-5k-NH2) and a thiol (4ARM-5k-SH) were studied with the ester 4ARM-10k-SG. The formulation details and material properties are given in Table 4. A 0.058 M phosphate buffer with a pH of 7.97 yielded a gel time of 150 seconds with the amine. A 0.05 M borate buffer with a pH of 8.35 produced a gel time of 75 seconds with the thiol.

The amine-based polymer appeared to show no signs of degradation, as was expected from the lack of degradable groups. However, the thiol-based polymer degraded in 5 days. This suggests that degradation is occurring through alternate pathways, as was observed in the thiol formulations with 4ARM-10k-SS and 4ARM-20k-SGA (vida supra).

TABLE 4

Gel and degradation times for amines and thiols with 4ARM-10k-SG formulations.

| Components | Reaction Buffer Type, Concentration, and pH | Gel Time (s) | Degradation Time (days) |
|---|---|---|---|
| 4ARM-5k-NH2 & 4ARM-10k-SG | Phosphate (0.058M, pH 7.97) | 150 | Indefinite |
| 4ARM-5k-SH & 4ARM-10k-SG | Borate (0.05M, pH 8.35) | 75 | 5 |

Example 9

Gelling and Degradation Times of Thiol-Sorbitol Polyglycidyl Ether Polymers

With ETTMP-1300 conditions such as high pH (10), high solution concentration (50%), or high borate concentration (0.16 M) were necessary for the mixture to gel. Gel times ranged from around 30 minutes to many hours. The conditions that were explored include: pH from 7 to 12; solution concentration from 5% to 50%; borate concentration from 0.05 M to 0.16 M; and thiol to epoxide ratios from 1:2 to 2:1.

The high pH necessary for the reaction to occur could result in degradation of the thiol. Thus, a polymer with EJ-190 and 4ARM-5k-SH was prepared. A 13% solution formulation exhibited a gel time of 230 seconds at a pH of between 9 and 10. The degradation time was 32 days. At a lower pH of around 8, the mixture exhibited gel times in the range of 1 to 2 hours.

Example 10

General Procedure for the Preparation of Polymerizable Pre-Formulations

Several representative sticky formulations are listed in Table 5 along with specific reaction details for the preparation of polymerizable pre-formulations. The hydrogel polymers were prepared by first dissolving the amine component in phosphate buffer or the thiol component in borate buffer. The appropriate amount of the ester component was then added and the entire solution was mixed vigorously for 10 to 20 seconds. The gel time was measured starting from the addition of the ester until the gelation of the solution.

TABLE 5

(A) Summary of the reaction details for several representative sticky formulations without viscosity enhancer; (B) more detailed tabulation of a selection of the reaction details including moles (degradation times were measured in phosphate buffered saline (PBS) at 37° C.).

(A)

| Components | Amine or Thiol/Ester Molar Ratio | Buffer | % Solution | Gel Time (s) | Degradation Time (days) |
|---|---|---|---|---|---|
| 8ARM-20k-NH2 4ARM-20K-SGA | 3 | 0.15M phosphate, pH 7.99 | 3 | 130 | N/A |
| 8ARM-20k-NH2 4ARM-20K-SGA | 1/3 | 0.15M phosphate, pH 7.99 | 3 | 300 | N/A |
| 8ARM-20k-NH2 4ARM-10K-SS | 3 | 0.15M phosphate, pH 7.99 | 8 | 50 | N/A |
| 8ARM-20k-NH2 4ARM-10K-SS | 1/3 | 0.15M phosphate, pH 7.99 | 8 | 80 | N/A |
| 4ARM-20K-AA/ 8ARM-20k-NH2 (75/25) 4ARM-20K-SGA | 3 | 0.15M phosphate, pH 7.99 | 5 | 210 | 1 to 3 |
| 4ARM-20K-AA/ 8ARM-20k-NH2 (75/25) 4ARM-20K-SGA | 5 | 0.15M phosphate, pH 7.99 | 10 | 180 | 1 to 3 |
| 4ARM-5K-NH2 4ARM-10K-SG | 5 | 0.10M phosphate, pH 7.80 | 10 | 160 | 7 |
| 4ARM-5K-NH2 4ARM-10K-SS | 5 | 0.10M phosphate, pH 7.80 | 20 | 160 | 1 to 3 |
| 4ARM-5K-NH2 4ARM-10K-SG | 3 | 0.10M phosphate, pH 7.80 | 5 | 160 | 13 |
| 4ARM-5K-NH2 4ARM-10K-SG | 5 | 0.15M phosphate, pH 7.99 | 20 | 80 | 7 |
| 4ARM-5K-NH2 4ARM-10K-SG | 5 | 0.15M phosphate, pH 7.99 | 30 | 70 | 10 |
| 4ARM-5K-NH2 4ARM-20K-SGA | 5 | 0.15M phosphate, pH 7.99 | 19 | 60 | 53 |
| 4ARM-5K-NH2 4ARM-20K-SGA | 5 | 0.15M phosphate, pH 7.99 | 12 | 70 | 53 |
| 4ARM-5K-NH2 4ARM-10K-SG | 1/5 | 0.15M phosphate, pH 7.99 | 19 | 160 | 15 |
| 4ARM-SH-5K 4ARM-10K-SG | 5 | 0.05M borate, pH 7.93 | 20 | 120 | 2 to 4 |
| 4ARM-NH2-2K 8ARM-15K-SG | 5 | 0.10M phosphate, pH 7.46 | 10 | 120 | 15 |
| 4ARM-NH2-2K 4ARM-20K-SGA | 7 | 0.10M phosphate, pH 7.80 | 30 | 150 | N/A |

TABLE 5-continued (A) Summary of the reaction details for several representative sticky formulations without viscosity enhancer; (B) more detailed tabulation of a selection of the reaction details including moles (degradation times were measured in phosphate buffered saline (PBS) at 37° C.).

(B)

| Components | MW | Mmoles | Wt (g) | Arm | mmoles | Arms Eq | Polymer % Solution (w/v) |
|---|---|---|---|---|---|---|---|
| 8ARM-20k-NH2 | 20000 | 1000 | 0.075 | 8 | 0.00375 | 0.03 | |
| 4ARM-20k-SGA | 20000 | 1000 | 0.05 | 4 | 0.0025 | 0.01 | |
| Buffer Volume (phosphate) | | | 4.1 | | | | 3.0 |
| 8ARM-20k-NH2 | 20000 | 1000 | 0.025 | 8 | 0.00125 | 0.01 | |
| 4ARM-20k-SGA | 20000 | 1000 | 0.15 | 4 | 0.0075 | 0.03 | |
| Buffer Volume (phosphate) | | | 5.8 | | | | 3.0 |
| 8ARM-20k-NH2 | 20000 | 1000 | 0.3 | 8 | 0.015 | 0.12 | |
| 4ARM-10k-SS | 10000 | 1000 | 0.1 | 4 | 0.01 | 0.04 | |
| Buffer Volume (phosphate) | | | 5 | | | | 8.0 |
| 8ARM-20k-NH2 | 20000 | 1000 | 0.1 | 8 | 0.005 | 0.04 | |
| 4ARM-10k-SS | 10000 | 1000 | 0.3 | 4 | 0.03 | 0.12 | |
| Buffer Volume (phosphate) | | | 5 | | | | 8.0 |

TABLE 6

Gel times for the 8ARM-20k-NH2/4ARM-20k-SGA(1/1) sticky polymers including HPMC as viscosity enhancer with varying buffers and concentrations.

| Components | Amine/Ester Molar Ratio | Buffer | % Solution | Gel Time (min) |
|---|---|---|---|---|
| 8ARM-20k-NH2 4ARM-20K-SGA 0.3% HPMC | 1 | 0.10M phosphate, pH 7.80 | 4.8 | 1.5 |
| 8ARM-20k-NH2 4ARM-20K-SGA 0.3% HPMC | 1 | 0.10M phosphate, pH 7.46 | 4.8 | 3.5 |
| 8ARM-20k-NH2 4ARM-20K-SGA 0.3% HPMC | 1 | 0.05M phosphate, pH 7.42 | 4.8 | 4.5 |
| 8ARM-20k-NH2 4ARM-20K-SGA 0.3% HPMC | 1 | 0.05M phosphate, pH 7.42 | 4 | 5.5 |
| 8ARM-20k-NH2 4ARM-20K-SGA 0.3% HPMC | 1 | 0.05M phosphate, pH 7.42 | 3 | 8.5 |
| 8ARM-20k-NH2 4ARM-20K-SGA 0.3% HPMC | 1 | 0.05M phosphate, pH 7.24 | 4.8 | 6.75 |
| 8ARM-20k-NH2 4ARM-20K-SGA 0.3% HPMC | 1 | 0.05M phosphate, pH 7.24 | 3 | 12 |
| 8ARM-20k-NH2 4ARM-20K-SGA 0.3% HPMC | 1 | 0.05M phosphate, pH 7.24 | 2.5 | 15.5 |

Gel times ranged from 60 to 300 seconds and were found to be easily tuned by adjusting the reaction buffer pH, buffer concentration, or polymer concentration. An example of gel time control for a single formulation is shown in Table 6, where the gel time for the 8ARM-20k-NH2/4ARM-20k-SGA (1/1) polymer was varied from 1.5 to 15.5 minutes.

In some instances, the stickiness of the polymers originates from a mismatching in the molar equivalents of the components. A variety of sticky materials using combinations of 4 or 8 armed amines of molecular weights between 2 and 20 thousand and 4 or 8 armed esters of molecular weights between 10 and 20 thousand were created. It was found that in comparison with the 8 armed esters, the 4 armed esters resulted in stickier materials. For the amine component, it was found that smaller molecular weights led to stickier materials and higher amine to ester molar ratios.

A mismatch (amine to ester molar ratio) of at least 3 was required to qualitatively sense stickiness. More preferably, a ratio of around 5 produced a desirable level of stickiness combined with polymer strength. Polymers with amine to ester molar ratios higher than 5 may be formed as well, but some reaction conditions, such as the polymer concentration, may need to be adjusted to obtain a reasonable gel time. Furthermore, it was found that the use of a viscosity enhanced solution improves the polymers by increasing their strength and elasticity, allowing for higher amine to ester molar ratios (Example 11; Table 9).

The materials formed were typically transparent and elastic. Stickiness was tested for qualitatively by touch. Thus, a sticky material adhered to a human finger or other surface and remained in place until removed. Degradation times varied from 1 to 53 days. In certain instances, he polymer properties, such as gel and degradation times, pore sizes, swelling, etc. may be optimized for different applications without losing the stickiness.

Example 11

General Procedure for the Preparation of Solutions with Enhanced Viscosity

Polymer solutions with enhanced viscosities were prepared by the addition of a viscosity enhancing agent to the reaction buffer. Table9B lists the viscosity enhancing agents studied, including observations on the properties of the formed polymers. Stock solutions of reaction buffers were prepared with varying concentrations of methylcellulose (MC), hypromellose (HPMC) or polyvinylpyrrolidone (PVP). As an example, a 2% (w/w) HPMC solution in buffer was made by adding 0.2 g of HPMC to 9.8 mL of 0.10 M phosphate buffer at pH 7.80, followed by vigorous shaking. The solution was allowed to stand overnight. Buffer solutions with HPMC concentrations ranging from 0.01% to 2.0% were prepared in a similar fashion. Buffer solutions with PVP concentrations ranging from 5% to 20% and buffer solutions with MC concentrations ranging from 1.0 to 2.0% were also prepared by a similar method.

The polymers were formed in the same method as described above in the general procedures for the preparation of the sticky materials (Example 10). A typical procedure involved first dissolving the amine component in the phosphate buffer containing the desired concentration of viscosity enhancing agent. The appropriate amount of the ester component was then added and the entire solution was mixed vigorously for 10 to 20 seconds. The gel time was measured starting from the addition of the ester until the gelation of the solution.

Several representative formulations are listed in Table 7 and Table 8 along with specific reaction details. The percent of degradable acetate amine component by mole equivalents is represented by a ratio designated in parenthesis. For example, a formulation with 75% degradable amine will be written as 8ARM-20k-AA/8ARM-20k-NH2 (75/25). The polymer was prepared by first dissolving the amine component in phosphate buffer. The appropriate amount of the ester component was then added and the entire solution was mixed vigorously for 10 to 20 seconds. The gel time was measured starting from the addition of the ester until the gelation of the solution.

The gel time is dependent on several factors: pH, buffer concentration, polymer concentration, temperature and the monomers used. Previous experiments have shown that the extent of mixing has little effect on the gel time once the components are in solution, which typically takes up to 10 seconds. The effect of monomer addition on buffer pH was measured. For the 8ARM-20k-NH2 & 4ARM-20k-SGA formulation, the buffer pH drops slightly from 7.42 to 7.36 upon addition of the monomers. For the 8ARM-20k-AA/8ARM-20k-NH2 (70/30) & 4ARM-20k-SGA formulation, the buffer pH drops from 7.4 to 7.29 upon addition of the monomers. The additional decrease in the pH was found to originate from acidic residues in the degradable acetate amine. The same pH drop phenomenon was observed for the 4ARM-20k-AA amine. In certain instances, a quality control specification on the acetate amine solution pH may be required to improve the consistency of degradable formulations.

The effect of reaction buffer pH on gel times was determined. The gel times increase with an increase in the concentration of hydronium ions in an approximately linear fashion. More generally, the gel times decrease with an increase in the buffer pH. In addition, the effect of reaction buffer phosphate concentration on gel times was investigated. The gel times decrease with an increase in the phosphate concentration. The effect of polymer concentration on gel times was reviewed. The gel times decrease significantly with an increase in the polymer concentration. At low polymer concentrations where the gel time is greater than 5 minutes, hydrolysis reactions of the ester begin to compete with the formation of the polymer. The effect of temperature on gel times appears to follow the Arrhenius equation. The gel time is directly related to the extent of reaction of the polymer solution and so this behavior is not unusual.

The rheology of the polymers during the gelation process was measured as a function of the percent time to the gel point. When 100% represents the gel point and 50% represents half the time before the gel point, the viscosity of the reacting solution remains relatively constant until about 80% of the gel point. After that point, the viscosity increases dramatically, representing the formation of the solid gel.

The gel time stability of a single formulation using the same lot of monomers over the course of about a year was investigated. The monomers were handled according to the standard protocol outlined above. The gel times remained relatively stable; some variations in the reaction buffer may account for differences in the gel times.

The gel times for the polymer in the single syringe system used with various liquids was reviewed. The gel times remained consistent with the use of distilled water, Nolvasan, Kenalog-10 and Depo-Medrol. The large increase in gel time with the use of saline may be attributed to the preservatives and buffer in the saline, which was formulated for use as a nasal spray. Pure medical saline for use in IV or irrigation is expected to yield gel times in line with the current results.

TABLE 7

(A) Summary of the reaction details for several representative sticky formulations; (B) more detailed tabulation of a selection of the reaction details including moles (degradation times were measured in phosphate buffered saline (PBS) at 37° C.).

(A)

| Components | Buffer | % Solution | Gel Time (s) | Degradation Time (days) |
|---|---|---|---|---|
| 4ARM-20k-AA/8ARM-20k-NH2 (60/40) 4ARM-20k-SGA | 0.10M phosphate, pH 7.80 | 5 | 150 | 21 |
| 4ARM-20k-AA/8ARM-20k-NH2 (60/40) 4ARM-20k-SGA 0.3% HPMC | 0.10M phosphate, pH 7.80 | 5 | 150 | 21 |
| 8ARM-20k-NH2 4ARM-20k-SGA 0.3% HPMC | 0.10M phosphate, pH 7.80 | 4.8 | 100 | N/A |
| 8ARM-20k-NH2 8ARM-15k-SG 0.3% HPMC | 0.10M phosphate, pH 7.80 | 4.8 | 70 | 48 |
| 4ARM-20k-AA/8ARM-20k-NH2 (60/40) 8ARM-15k-SG 0.3% HPMC | 0.10M phosphate, pH 7.80 | 4.8 | 110 | 12 |
| 4ARM-20k-AA/8ARM-20k-NH2 (60/40) 4ARM-20k-SGA 0.3% HPMC | 0.10M phosphate, pH 7.80 | 20 | 160 | 21 |
| 8ARM-20k-NH2 4ARM-20k-SGA | 0.10M phosphate, pH 7.80 | 4.8 | 90 | N/A |
| 8ARM-20k-NH2 4ARM-20k-SGA 1.0% HPMC | 0.10M phosphate, pH 7.80 | 4.8 | 80 | N/A |

TABLE 7-continued (A) Summary of the reaction details for several representative sticky formulations; (B)
more detailed tabulation of a selection of the reaction details including moles (degradation times
were measured in phosphate buffered saline (PBS) at 37° C.).

| Formulation | Buffer | | | |
|---|---|---|---|---|
| 8ARM-20k-NH2 4ARM-20k-SGA 0.3% HPMC | 0.10M phosphate, pH 7.46 | 4.8 | 210 | N/A |
| 8ARM-20k-NH2 4ARM-20k-SGA 0.3% HPMC | 0.05M phosphate, pH 7.42 | 4.8 | 270 | N/A |
| 8ARM-20k-NH2 4ARM-20k-SGA 0.3% HPMC | 0.05M phosphate, pH 7.42 | 4 | 330 | N/A |
| 8ARM-20k-NH2 4ARM-20k-SGA 0.3% HPMC | 0.05M phosphate, pH 7.42 | 3 | 510 | N/A |
| 8ARM-20k-NH2 4ARM-20k-SGA 0.3% HPMC | 0.05M phosphate, pH 7.24 | 4.8 | 405 | N/A |
| 8ARM-20k-NH2 4ARM-20k-SGA 0.3% HPMC | 0.05M phosphate, pH 7.24 | 3 | 720 | N/A |
| 8ARM-20k-NH2 4ARM-20k-SGA 0.3% HPMC | 0.05M phosphate, pH 7.24 | 2.5 | 930 | N/A |
| 8ARM-20k-AA 4ARM-20k-SGA HPMC (0.3%) | 0.10M phosphate, pH 7.46 | 4.8 | 90 | 6 |
| 8ARM-20k-AA/8ARM-20k-NH2 (75/25) 4ARM-20k-SGA HPMC (0.3%) | 0.10M phosphate, pH 7.46 | 4.8 | 100 | 16 |
| 8ARM-20k-AA/8ARM-20k-NH2 (60/40) 4ARM-20k-SGA HPMC (0.3%) | 0.10M phosphate, pH 7.46 | 4.8 | 95 | 256 (estimated) |
| 8ARM-20k-AA/8ARM-20k-NH2 (50/50) 4ARM-20k-SGA HPMC (0.3%) | 0.10M phosphate, pH 7.46 | 4.8 | 120 | N/A |
| 8ARM-20k-AA/8ARM-20k-NH2 (70/30) 4ARM-20k-SGA HPMC (0.3%) | 0.10M phosphate, pH 7.46 | 4.8 | 100 | 21 |
| 8ARM-20k-AA/8ARM-20k-NH2 (65/35) 4ARM-20k-SGA HPMC (0.3%) | 0.10M phosphate, pH 7.46 | 4.8 | 100 | 28 |
| 8ARM-20k-NH2 4ARM-20k-SGA 1.5% HPMC | 0.10M phosphate, 7.80 pH | 4.8 | 90 | N/A |
| 8ARM-20k-AA/8ARM-20k-NH2 (75/25) 4ARM-20k-SGA HPMC (0.3%) | 0.10M phosphate, pH 7.46 | 4.8 | 90 | 16 |
| 8ARM-20k-AA/8ARM-20k-NH2 (70/30) 4ARM-20k-SGA HPMC (0.3%) | 0.10M phosphate, pH 7.46 | 4.8 | 105 | 21 |
| 8ARM-20k-AA/8ARM-20k-NH2 (50/50) 4ARM-20k-SGA HPMC (0.3%) | 0.10M phosphate, pH 7.46 | 4.8 | 120 | N/A |
| 8ARM-20k-AA/8ARM-20k-NH2 (70/30) 8ARM-15k-SG HPMC (0.3%) | 0.10M phosphate, pH 7.46 | 4.8 | 70 | 7 |
| 4ARM-20k-AA/8ARM-20k-NH2 (70/30) 4ARM-20k-SGA HPMC (0.3%) | 0.10M phosphate, pH 7.46 | 4.8 | 260 | 10 |
| 8ARM-20k-AA/8ARM-20k-NH2 (60/40) 8ARM-15k-SG HPMC (0.3%) | 0.10M phosphate, pH 7.46 | 4.8 | 70 | 17 |
| 8ARM-20k-AA 4ARM-20k-SGA HPMC (0.3%) | 0.10M phosphate, pH 7.46 | 4.8 | 85 | 7 |

TABLE 7-continued (A) Summary of the reaction details for several representative sticky formulations; (B) more detailed tabulation of a selection of the reaction details including moles (degradation times were measured in phosphate buffered saline (PBS) at 37° C.).

| | | | | |
|---|---|---|---|---|
| 8ARM-20k-AA/8ARM-20k-NH2 (70/30) 4ARM-20k-SGA HPMC (0.3%) | 0.10M phosphate, pH 7.46 | 4.8 | 95 | 13 |
| 8ARM-20k-AA/8ARM-20k-NH2 (75/25) 4ARM-20k-SGA HPMC (0.3%) | 0.10M phosphate, pH 7.46 | 4.8 | 95 | 10 |
| 8ARM-20k-AA/8ARM-20k-NH2 (75/25) 4ARM-20k-SGA HPMC (0.3%) | 0.10M phosphate, pH 7.58 | 4 | 110 | In Progress |
| 8ARM-20k-AA/8ARM-20k-NH2 (75/25) 4ARM-20k-SGA HPMC (0.3%) | 0.10M phosphate, pH 7.58 | 3.5 | 150 | In Progress |
| 8ARM-20k-AA/8ARM-20k-NH2 (75/25) 4ARM-20k-SGA HPMC (0.3%) | 0.10M phosphate, pH 7.58 | 3 | 190 | In Progress |

(B)

| Components | MW | Mmoles | Wt (g) | Arm | mmoles | Arms Eq | Polymer % Solution (w/v) |
|---|---|---|---|---|---|---|---|
| 8ARM-20k-NH2 | 20000 | 1000 | 0.04 | 8 | 0.002 | 0.016 | |
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 8ARM-20k-NH2 | 20000 | 1000 | 0.08 | 8 | 0.004 | 0.032 | |
| 8ARM-15k-SG | 15000 | 1000 | 0.06 | 8 | 0.004 | 0.032 | |
| Buffer Volume (phosphate) | | | 2.9 | | | | 4.8 |
| Viscosity Enhancer | | | | 0.3% HPMC | | | |
| 8ARM-20k-AA | 20000 | 1000 | 0.04 | 8 | 0.002 | 0.016 | |
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 4ARM-20k-AA | 20000 | 1000 | 0.06 | 4 | 0.003 | 0.012 | |
| 8ARM-20k-NH2 | 20000 | 1000 | 0.02 | 8 | 0.001 | 0.008 | |
| 4ARM-20k-SGA | 20000 | 1000 | 0.1 | 4 | 0.005 | 0.02 | |
| Buffer Volume (phosphate) | | | 3.6 | | | | 5.0 |
| Viscosity Enhancer | | | | 0.3% HPMC | | | |
| 4ARM-20k-AA | 20000 | 1000 | 0.12 | 4 | 0.006 | 0.024 | |
| 8ARM-20k-NH2 | 20000 | 1000 | 0.04 | 8 | 0.002 | 0.016 | |
| 8ARM-15k-SG | 15000 | 1000 | 0.075 | 4 | 0.005 | 0.02 | |
| Buffer Volume (phosphate) | | | 4.9 | | | | 4.8 |
| Viscosity Enhancer | | | | 0.3% HPMC | | | |
| 8ARM-20k-AA | 20000 | 1000 | 0.06 | 8 | 0.003 | 0.024 | |
| 8ARM-20k-NH2 | 20000 | 1000 | 0.02 | 8 | 0.001 | 0.008 | |
| 4ARM-20k-SGA | 20000 | 1000 | 0.16 | 4 | 0.008 | 0.032 | |
| Buffer Volume (phosphate) | | | 5 | | | | 4.8 |
| Viscosity Enhancer | | | | 0.3% HPMC | | | |
| 8ARM-20k-AA | 20000 | 1000 | 0.03 | 8 | 0.0015 | 0.012 | |
| 8ARM-20k-NH2 | 20000 | 1000 | 0.02 | 8 | 0.001 | 0.008 | |
| 4ARM-20k-SGA | 20000 | 1000 | 0.1 | 4 | 0.005 | 0.02 | |
| Buffer Volume (phosphate) | | | 3.1 | | | | 4.8 |
| Viscosity Enhancer | | | | 0.3% HPMC | | | |
| 8ARM-20k-AA | 20000 | 1000 | 0.02 | 8 | 0.001 | 0.008 | |
| 8ARM-20k-NH2 | 20000 | 1000 | 0.02 | 8 | 0.001 | 0.008 | |
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 8ARM-20k-AA | 20000 | 1000 | 0.035 | 8 | 0.00175 | 0.014 | |
| 8ARM-20k-NH2 | 20000 | 1000 | 0.015 | 8 | 0.00075 | 0.006 | |
| 4ARM-20k-SGA | 20000 | 1000 | 0.1 | 4 | 0.005 | 0.02 | |
| Buffer Volume (phosphate) | | | 3.1 | | | | 4.8 |
| Viscosity Enhancer | | | | 0.3% HPMC | | | |
| 8ARM-20k-AA | 20000 | 1000 | 0.039 | 8 | 0.00195 | 0.0156 | |
| 8ARM-20k-NH2 | 20000 | 1000 | 0.021 | 8 | 0.00105 | 0.0084 | |
| 4ARM-20k-SGA | 20000 | 1000 | 0.12 | 4 | 0.006 | 0.024 | |
| Buffer Volume (phosphate) | | | 3.75 | | | | 4.8 |
| Viscosity Enhancer | | | | 0.3% HPMC | | | |
| 8ARM-20k-AA | 20000 | 1000 | 0.09 | 8 | 0.0045 | 0.036 | |
| 8ARM-20k-NH2 | 20000 | 1000 | 0.03 | 8 | 0.0015 | 0.012 | |

TABLE 7-continued (A) Summary of the reaction details for several representative sticky formulations; (B)
more detailed tabulation of a selection of the reaction details including moles (degradation times
were measured in phosphate buffered saline (PBS) at 37° C.).

| | | | | | | | |
|---|---|---|---|---|---|---|---|
| 4ARM-20k-SGA | 20000 | 1000 | 0.24 | 4 | 0.012 | 0.048 | |
| Buffer Volume (phosphate) | | | 9 | | | | 4.0 |
| Viscosity Enhancer | | | | 0.3% HPMC | | | |
| 8ARM-20k-AA | 20000 | 1000 | 0.075 | 8 | 0.00375 | 0.03 | |
| 8ARM-20k-NH2 | 20000 | 1000 | 0.025 | 8 | 0.00125 | 0.01 | |
| 4ARM-20k-SGA | 20000 | 1000 | 0.2 | 4 | 0.01 | 0.04 | |
| Buffer Volume (phosphate) | | | 8.55 | | | | 3.5 |
| Viscosity Enhancer | | | | 0.3% HPMC | | | |
| 8ARM-20k-AA | 20000 | 1000 | 0.06 | 8 | 0.003 | 0.024 | |
| 8ARM-20k-NH2 | 20000 | 1000 | 0.02 | 8 | 0.001 | 0.008 | |
| 4ARM-20k-SGA | 20000 | 1000 | 0.16 | 4 | 0.008 | 0.032 | |
| Buffer Volume (phosphate) | | | 8 | | | | 3.0 |
| Viscosity Enhancer | | | | 0.3% HPMC | | | |

TABLE 8

(A) Summary of the reaction details for several representative sticky formulations; (B)
more detailed tabulation of a selection of the reaction details including moles (degradation times
were measured in phosphate buffered saline (PBS) at 37° C.).

(A)

| Components (Arm Equiv. Mol %) | | Poly. Conc. | Buffer Type & Components | | Estim. Deg. Time | Appr. Gel Time |
|---|---|---|---|---|---|---|
| 4ARM-20k-SGA | 100% | 5% | Liquid 2.5 mL | 0.10M Phosphate, pH 7.58 | 2 to 4 weeks | 125 s |
| 8ARM-20k-AA | 65% | | | | | |
| 8ARM-20k-NH2 | 35% | | | | | |
| HPMC | 0.3% | | | | | |
| 4ARM-20k-SGA | 100% | 5% | Liquid 2.5 mL | 0.10M Phosphate, pH 7.58 | 2 weeks | 115 s |
| 8-ARM-20k-AA | 75% | | | | | |
| 8ARM-20k-NH2 | 25% | | | | | |
| HPMC | 0.3% | | | | | |
| 4ARM-20k-SGA | 100% | 5% | Liquid 2.5 mL | 0.10M Phosphate, pH 7.58 | 2 weeks | 155 s |
| 8ARM-20k-AA | 70% | | | | | |
| 8ARM-20k-NH2 | 30% | | | | | |
| HPMC | 0.3% | | | | | |
| 4ARM-20k-SGA | 100% | 5% | Liquid 2.5 mL | 0.10M Phosphate, pH 7.58 | 2 weeks | 110 s to 125 s |
| 8ARM-20k-AA | 75% | | | | | |
| 8ARM-20k-NH2 | 25% | | | | | |
| HPMC | 0.3% | | | | | |
| 4ARM-20k-SGA | 100% | 5% | Liquid 2.5 mL | 0.10M Phosphate, pH 7.58 | 2 weeks | 122 s |
| 8ARM-20k-AA | 75% | | | | | |
| 8ARM-20k-NH2 | 25% | | | | | |
| HPMC | 0.3% | | | | | |
| 4ARM-20k-SGA | 100% | 5% | Liquid 2.5 mL 1000 ppm Denatonium benzoate | 0.10M Phosphate, pH 7.58 | 2 weeks | 90 s to 120 s |
| 8ARM-20k-AA | 75% | | | | | |
| 8ARM-20k-NH2 | 25% | | | | | |
| HPMC | 0.3% | | | | | |
| 4ARM-20k-SGA | 100% | 5% | Liquid 2.5 mL 500 ppm Denatonium benzoate | 0.10M Phosphate, pH 7.58 | 2 weeks | 90 s to 120s |
| 8ARM-20k-AA | 75% | | | | | |
| 8ARM-20k-NH2 | 25% | | | | | |
| HPMC | 0.3% | | | | | |
| 4ARM-20k-SGA | 100% | 5% | Liquid 2.5 mL 100 ppm Denatonium benzoate | 0.10M Phosphate, pH 7.58 | 2 weeks | 90 s to 120s |
| 8ARM-20k-AA | 75% | | | | | |
| 8ARM-20k-NH2 | 25% | | | | | |
| HPMC | 0.3% | | | | | |
| 4ARM-20k-SGA | 100% | 5% | Liquid 2.5 mL | 0.10M Phosphate, pH 7.58 | 2 weeks | 130 s |
| 8ARM-20k-AA | 70% | | | | | |
| 8ARM-20k-NH2 | 30% | | | | | |
| HPMC | 0.3% | | | | | |
| 4ARM-20k-SGA | 100% | 4% | Liquid 2.25 mL | 0.10M Phosphate, pH 7.46 | 2 weeks | 205 s to 230 s |
| 8ARM-20k-AA | 60% | | | | | |
| 8-ARM-20k-NH2 | 40% | | | | | |
| HPMC | 0.3% | | | | | |
| 4ARM-20k-SGA | 100% | 6% | Solid Freeze-dried (Aldrich) Suggested use w/2 mL drug solution | 0.10M Phosphate, pH 7.4 | 30-60 days | 90 s |
| 8ARM-20k-AA | 65% | | | | | |
| 8ARM-20k-NH2 | 35% | | | | | |

TABLE 8-continued (A) Summary of the reaction details for several representative sticky formulations; (B) more detailed tabulation of a selection of the reaction details including moles (degradation times were measured in phosphate buffered saline (PBS) at 37° C.).

| | | | | | | |
|---|---|---|---|---|---|---|
| 4ARM-20k-SGA | 100% | 5% | Liquid | 0.10M | 2 weeks | 90 s |
| 8ARM-20k-AA | 75% | | 2.5 mL | Phosphate, | | to |
| 8ARM-20k-NH2 | 25% | | | pH 7.58 | | 120 s |
| HPMC | 0.3% | | 10000 ppm | | | |
| | | | Denatonium benzoate | | | |
| 4ARM-20k-SGA | 100% | 5% | Liquid | 0.10M | 2 weeks | 115 s |
| 8ARM-20k-AA | 75% | | 2.5 mL | Phosphate, | | |
| 8ARM-20k-NH2 | 25% | | | pH 7.58 | | |
| HPMC | 0.3% | | | | | |
| 4ARM-20k-SGA | 100% | 5% | Liquid | 0.10M | 2 weeks | 150 s |
| 8ARM-20k-AA | 75% | | 2.5 mL | Phosphate, | | |
| 8ARM-20k-NH2 | 25% | | Using freeze-dried | pH 7.4 | | |
| | | | phosphate | | | |
| | | | 1% Denatonium | | | |
| | | | benzoate, 2% | | | |
| | | | Chlorhexidine | | | |
| 4ARM-20k-SGA | 100% | 6% | Solid | 0.10M | 2 weeks | 110 s |
| 8ARM-20k-AA | 75% | | Freeze-dried (Aldrich) | Phosphate, | | |
| 8ARM-20k-NH2 | 25% | | Suggested use w/2 mL | pH 7.4 | | |
| | | | drug solution | | | |
| 4ARM-20k-SGA | 100% | 6% | Liquid | 0.01M | 2 weeks | 27 min |
| 8ARM-20k-AA | 70% | | 2.0 mL | Phosphate, | | to |
| 8ARM-20k-NH2 | 30% | | Phosphate Buffered | 0.137M | | 31 min |
| HPMC | 0.3% | | Saline (PBS) | NaCl, | | |
| | | | | 0.0027M | | |
| | | | | KCl, | | |
| | | | | pH 7.2 | | |
| 4ARM-20k-SGA | 100% | 5% | Liquid | 0.10M | 2 weeks | 158 s |
| 8ARM-20k-AA | 70% | | 2.5 mL | Phosphate, | | |
| 8ARM-20k-NH2 | 30% | | Nolvasan (2% | pH 7.4 | | |
| | | | Chlorhexidine) | | | |

(B)

| Components | MW | Mmoles | Wt (g) | Arm | mmoles | Arms Eq | Polymer % Solution (w/v) |
|---|---|---|---|---|---|---|---|
| 8ARM-20k-AA | 20000 | 1000 | 0.03 | 8 | 0.0015 | 0.012 | |
| 8ARM-20k-NH2 | 20000 | 1000 | 0.01 | 8 | 0.0005 | 0.004 | |
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 8ARM-20k-AA | 20000 | 1000 | 0.03 | 8 | 0.0015 | 0.012 | |
| 8ARM-20k-NH2 | 20000 | 1000 | 0.01 | 8 | 0.0005 | 0.004 | |
| 4ARM-20k-SGA | 20000 | 1000 | 0.08 | 4 | 0.004 | 0.016 | |
| Buffer Volume (phosphate) | | | 2.5 | | | | 4.8 |
| Denatonium benzoate | | | | 1000 ppm | | | |
| Viscosity Enhancer | | | | 0.3% HPMC | | | |
| 8ARM-20k-AA | 20000 | 1000 | 0.03 | 8 | 0.0015 | 0.012 | |
| 8ARM-20k-NH2 | 20000 | 1000 | 0.01 | 8 | 0.0005 | 0.004 | |
| 4ARM-20k-SGA | 20000 | 1000 | 0.08 | 4 | 0.004 | 0.016 | |
| Buffer Volume (phosphate) | | | 2.5 | | | | 4.8 |
| Denatonium benzoate | | | | 500 ppm | | | |
| Viscosity Enhancer | | | | 0.3% HPMC | | | |
| 8ARM-20k-AA | 20000 | 1000 | 0.03 | 8 | 0.0015 | 0.012 | |
| 8ARM-20k-NH2 | 20000 | 1000 | 0.01 | 8 | 0.0005 | 0.004 | |
| 4ARM-20k-SGA | 20000 | 1000 | 0.08 | 4 | 0.004 | 0.016 | |
| Buffer Volume (phosphate) | | | 2.5 | | | | 4.8 |
| Denatonium benzoate | | | | 100 ppm | | | |
| Viscosity Enhancer | | | | 0.3% HPMC | | | |
| 8ARM-20k-AA | 20000 | 1000 | 0.03 | 8 | 0.0015 | 0.012 | |
| 8ARM-20k-NH2 | 20000 | 1000 | 0.01 | 8 | 0.0005 | 0.004 | |
| 4ARM-20k-SGA | 20000 | 1000 | 0.08 | 4 | 0.004 | 0.016 | |
| Buffer Volume (phosphate) | | | 2.5 | | | | 4.8 |
| Denatonium benzoate | | | | 10000 ppm | | | |
| Viscosity Enhancer | | | | 0.3% HPMC | | | |
| 8ARM-20k-AA | 20000 | 1000 | 0.03 | 8 | 0.0015 | 0.012 | |
| 8ARM-20k-NH2 | 20000 | 1000 | 0.01 | 8 | 0.0005 | 0.004 | |
| 4ARM-20k-SGA | 20000 | 1000 | 0.08 | 4 | 0.004 | 0.016 | |
| Solid Phosphate | | | 0.043 | | | | |
| Nolvasan Volume (2% chlorhexidine) | | | 2.5 | | | | 4.8 |
| Denatonium benzoate | | | | 10000 ppm | | | |
| 8ARM-20k-AA | 20000 | 1000 | 0.026 | 8 | 0.0013 | 0.0104 | |
| 8ARM-20k-NH2 | 20000 | 1000 | 0.014 | 8 | 0.0007 | 0.0056 | |

TABLE 8-continued (A) Summary of the reaction details for several representative sticky formulations; (B)
more detailed tabulation of a selection of the reaction details including moles (degradation times
were measured in phosphate buffered saline (PBS) at 37° C.).

| | | | | | | | |
|---|---|---|---|---|---|---|---|
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 8ARM-20k-AA | 20000 | 1000 | 0.028 | 8 | 0.0014 | 0.0112 | |
| 8ARM-20k-NH2 | 20000 | 1000 | 0.012 | 8 | 0.0006 | 0.0048 | |
| 4ARM-20k-SGA | 20000 | 1000 | 0.08 | 4 | 0.004 | 0.016 | |
| Buffer Volume (phosphate) | | | 2.5 | | | | 4.8 |
| Viscosity Enhancer | | | | 0.3% HPMC | | | |
| 8ARM-20k-AA | 20000 | 1000 | 0.018 | 8 | 0.0009 | 0.0072 | |
| 8ARM-20k-NH2 | 20000 | 1000 | 0.012 | 8 | 0.0006 | 0.0048 | |
| 4ARM-20k-SGA | 20000 | 1000 | 0.06 | 4 | 0.003 | 0.012 | |
| Buffer Volume (phosphate) | | | 2.25 | | | | 4 |
| Viscosity Enhancer | | | | 0.3% HPMC | | | |
| 8ARM-20k-AA | 20000 | 1000 | 0.026 | 8 | 0.0013 | 0.0104 | |
| 8ARM-20k-NH2 | 20000 | 1000 | 0.014 | 8 | 0.0007 | 0.0056 | |
| 4ARM-20k-SGA | 20000 | 1000 | 0.08 | 4 | 0.004 | 0.016 | |
| Solid Phosphate | | | 0.035 | | | | 6 |
| Drug Solution | | | | 2.0 mL | | | |
| 8ARM-20k-AA | 20000 | 1000 | 0.027 | 8 | 0.00135 | 0.0108 | |
| 8ARM-20k-NH2 | 20000 | 1000 | 0.009 | 8 | 0.00045 | 0.0036 | |
| 4ARM-20k-SGA | 20000 | 1000 | 0.072 | 4 | 0.0036 | 0.0144 | |
| Solid Phosphate | | | 0.035 | | | | 5.4 |
| Drug Solution | | | | 2.0 mL | | | |
| 8ARM-20k-AA | 20000 | 1000 | 0.028 | 8 | 0.0014 | 0.0112 | |
| 8ARM-20k-NH2 | 20000 | 1000 | 0.012 | 8 | 0.0006 | 0.0048 | |
| 4ARM-20k-SGA | 20000 | 1000 | 0.08 | 4 | 0.004 | 0.016 | |
| Buffer Volume (phosphate) | | | 2 | | | | 6 |
| Viscosity Enhancer | | | | 0.3% HPMC | | | |
| 8ARM-20k-AA | 20000 | 1000 | 0.028 | 8 | 0.0014 | 0.0112 | |
| 8ARM-20k-NH2 | 20000 | 1000 | 0.012 | 8 | 0.0006 | 0.0048 | |
| 4ARM-20k-SGA | 20000 | 1000 | 0.08 | 4 | 0.004 | 0.016 | |
| Solid Phosphate | | | 0.043 | | | | |
| Nolvasan Volume (2% chlorhexidine) | | | 2.5 | | | | 4.8 |
| Denatonium benzoate | | | | 1% | | | |

Cytotoxicity & Hemolysis Evaluation

Several polymer samples were sent out to NAMSA for cytotoxicity and hemolysis evaluation. Cytotoxic effects were evaluated according to ISO 10993-5 guidelines. Hemolysis was evaluated according to procedures based on ASTM F756 and ISO 10993-4.

The polymer 8ARM-20k-NH2 & 4ARM-20k-SGA at 4.8% solution with 0.3% HPMC was found to be non-cytotoxic and non-hemolytic. The polymer 8ARM-20k-AA/8ARM-20k-NH2 (70/30) & 4ARM-20k-SGA at 4.8% solution with 0.3% HPMC was found to be non-cytotoxic and non-hemolytic. In addition, formulations involving 4ARM-20kAA and 8ARM-15k-SG were also non-cytotoxic and non-hemolytic.

Gel and Degradation Time Measurements

The gel time for all cases was measured starting from the addition of the ester until the gelation of the solution. The gel point was noted by pipetting 1 mL of the reaction mixture and observing the dropwise increase in viscosity until the mixture ceased to flow. Degradation of the polymers was performed by the addition of 1 to 10 mL of phosphate buffered saline per 1 g of the material in a 50 mL centrifuge tube and incubating the mixture at 37° C. A digital water bath was used to maintain the temperature. The degradation time was measured starting from the day of addition of the phosphate buffer to complete dissolution of the polymer into solution.

The effect of reaction buffer pH, phosphate concentration, polymer concentration and reaction temperature on the gel times were characterized. The buffer pH was varied from 7.2 to 8.0 by the dropwise addition of either 50% aqueous NaOH or 6.0 N HCl. Phosphate concentrations of 0.01, 0.02 and 0.05 M were prepared and adjusted to pH 7.4. Polymer concentrations from 2 to 20% solution were studied. Reaction temperatures of 5, 20, and 37° C. were tested by keeping the monomers, buffers, and reaction mixture at the appropriate temperature. The 5° C. environment was provided by a refrigerator and the 37° C. temperature was maintained via the water bath. Room temperature was found to be 20° C.

The effect of degradation buffer pH and the proportion of degradable amine in the polymer formulation on the degradation times were explored. The degradation buffer pH was varied from 7.2 to 9.0 by the dropwise addition of either 50% aqueous NaOH or 6.0 N HCl. The degradable amine components studied were either the 4ARM-20k-AA or the 8ARM-20k-AA, and the percent of degradable amine relative to the non-degradable amine was varied from 50 to 100%.

The degradation time is largely dependent on the buffer pH, temperature, and the monomers used. Degradation occurs primarily through ester bond hydrolysis; in biological systems, enzymatic pathways may also play a role. FIG. 1 compares the degradation times of formulations with 4ARM-20k-AA and 8ARM-20k-AA in varying amounts. In general, increasing the amount of degradable acetate amine in relation to the non-degradable amine decreases the degradation times. Additionally, in some instances, the 8ARM-20k-AA exhibits a longer degradation time than the 4ARM-20k-AA per mole equivalent, which becomes especially apparent when the percent of acetate amine drops below 70%.

The effect of the buffer pH on the degradation time was measured. The pH range between 7.2 and 9.0 was studied. In general, a high pH environment results in a greatly accelerated degradation. For example, an increase in pH from approximately 7.4 to 7.7 decreases the degradation time by about half.

The degradation time of different Acetate Amine formulations was investigated. A pre-formulation with 70% Acetate Amine has a degradation time of approximately 14 days whereas a pre-formulation with 62.5% Acetate Amine has a degradation time of approximately 180 days.

Figure 2:
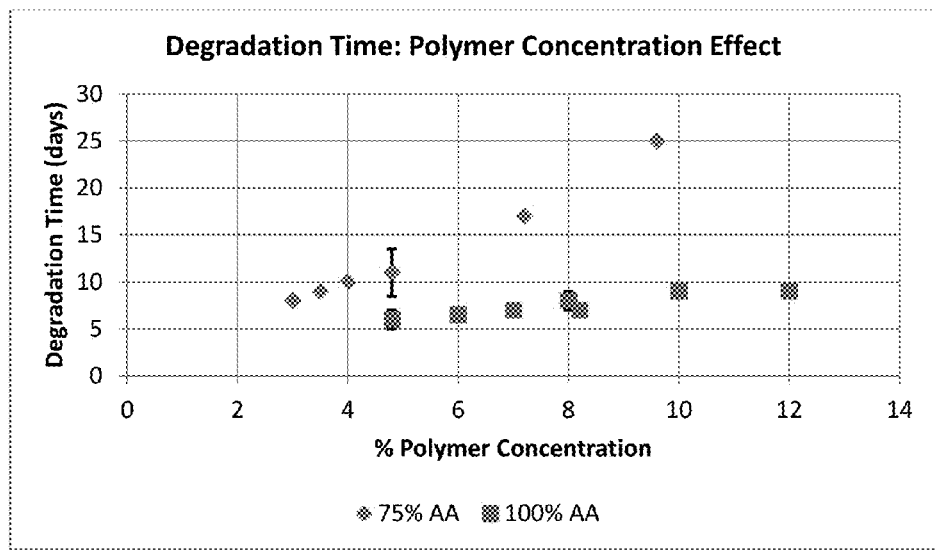
FIG. 2 shows the effect of polymer concentration on degradation time for 75% Acetate Amine formulation and 100% Acetate Amine formulation.

FIG. 2 shows the effect of polymer concentration on degradation time for different Acetate Amine formulations, where increasing polymer concentration slightly increases the degradation time (75% Acetate Amine formulation). This effect is less apparent for 100% Acetate Amine formulation, where the rate of ester hydrolysis is more significant.

The monomers used in the formulations have also been found to play a role in the way the polymer degrades. For the 8ARM-20k-AA/8ARM-20k-NH2 (70/30) & 4ARM-20k-SGA polymer, degradation occurred homogeneously throughout the material, resulting in a "smooth" degradation process. The polymer absorbed water and swelled slightly over the initial few days. Then, the polymer became gradually softer yet maintained its shape. Finally, the polymer lost its shape and became a highly viscous fluid.

When the amount of degradable amine becomes low, non-degradable regions in the polymer may occur. The 8ARM-20k-AA/8ARM-20k-NH2 (60/40) & 4ARM-20k-SGA formulation after approximately 80 days was compared with the 4ARM-20k-AA/8ARM-20k-NH2 (70/30) & 4ARM-20k-SGA formulation. The 4ARM-20k-AA/8ARM-20k-NH2 (70/30) & 4ARM-20k-SGA formulation degraded into several large fragments. For applications where the polymers are subjected to great forces, fragmentation may also occur as the polymer becomes softer and weaker over time.

Polymer Concentration

Figure 3A:
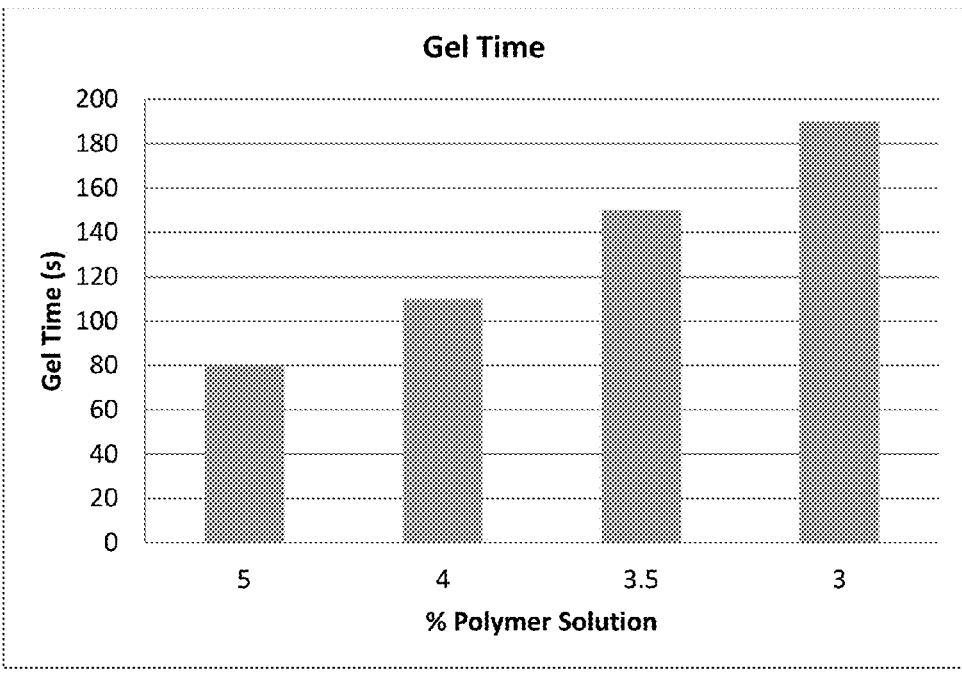
FIG. 3A-3D shows the effect of polymer solution on gel time (3A), firmness (3B), tack (3C), and elastic modulus (3D) for the formulation: 8ARM-20k-AA/8ARM-20k-NH2 (75/25) & 4ARM-20k-SGA with 0.3% HPMC. The error bars represent the standard deviations of 3 samples.
Figure 3B:
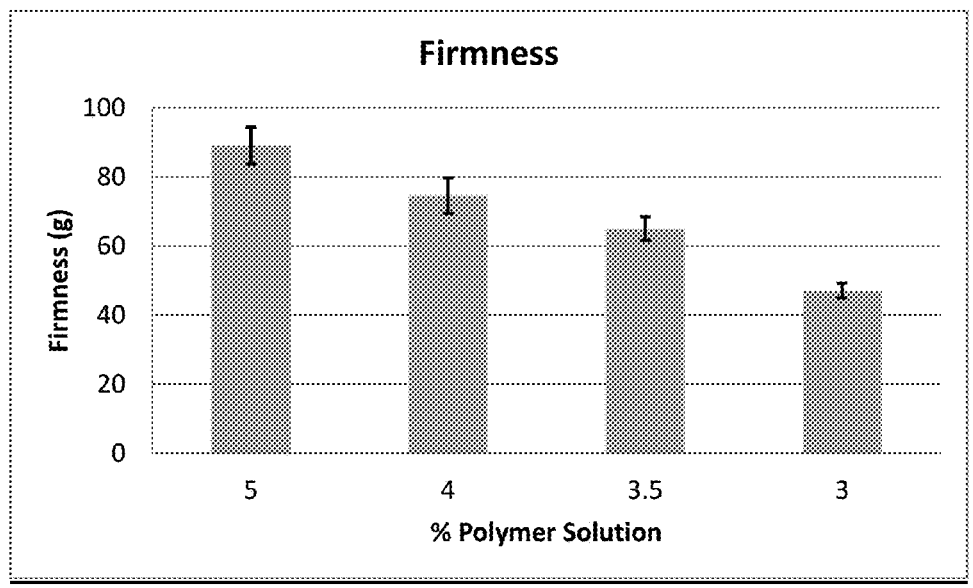
Figure 3C:
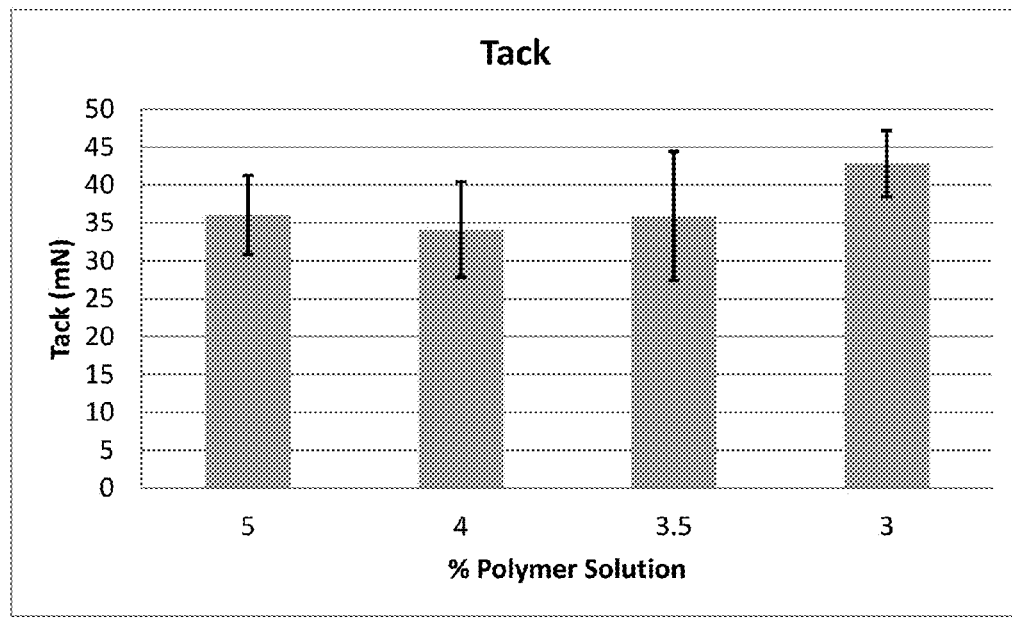
Figure 3D:
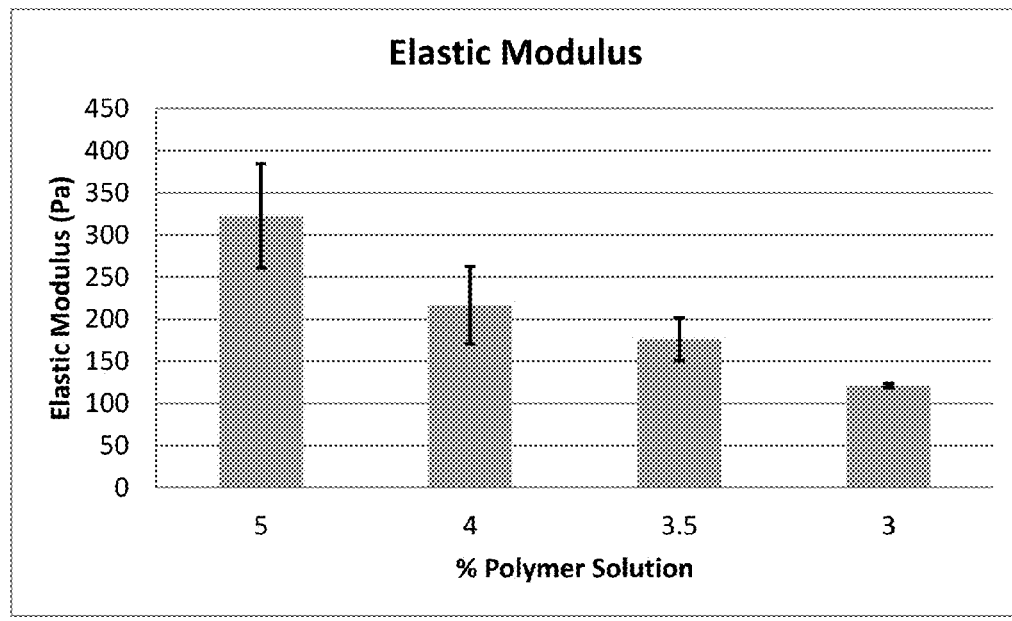

More dilute polymer solutions may be employed with minimal changes in the mechanical properties. For the formulation 8ARM-20k-AA-20K/8ARM-20k-NH2 (75/25) with 4ARM-20k-SGA and 0.3% HPMC, polymer concentrations of 3.0, 3.5 and 4.0% were studied. FIG. 3A shows the gel times, which increased steadily as the polymer concentration was lowered. The firmness decreased slightly as the polymer concentration was lowered (FIG. 3B). The tack is shown in FIG. 3C. There was essentially no change in the polymer adhesive properties. The elastic modulus decreased slightly as the polymer concentration was lowered (FIG. 3D).

TABLE 9

(A) Reaction details for specific sticky formulation; (B) formulation results for a specific sticky formulation with a variety of viscosity enhancing agents (the hydrogel surface spread test is conducted on a hydrophilic hydrogel surface composed of 97.5% water at an angle of approximately 30°; one drop of the polymer solution from a 22 gauge needle is applied to the surface before gelation); (C) the clarity of solutions containing a variety of viscosity enhancing agents, as measured by the % transmission at 650 nm.

(A)

| Components | MW | wt (g) | Arm | mmoles | Arms Eq | % Solution |
|---|---|---|---|---|---|---|
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate buffer | | | 2.5 mL 0.10M, pH 7.80 | | | 4.8 |

(B)

| Viscous Agent % (w/w) | Approx. Viscosity (cP) | Gel Time (s) | Hydrogel Surface Spread Test Category | Notes |
|---|---|---|---|---|
| 0 (Original Formulation) | 1.1 | 80 | 2 | Rigid, has "bounce". Slight elasticity. |
| 5% PVP | 1 to 5 | 90 | 2 to 3 | No change, except for a slight increase in elasticity. |
| 10% PVP | 3 to 5 | 90 | 2 to 3 | Slightly opaque, moderate increase in elasticity. Slippery. |
| 15% PVP | 5 to 10 | 100 | 2 to 3 | Opaque, definite increase in elasticity. Slippery when wet, slightly sticky when dry. |
| 20% PVP | 10 | 110 | 2 | Opaque, definite increase in elasticity. Slippery when wet, very sticky when dry. |
| 0.3% HPMC | 8.4 | 80 | 2 | No change. |
| 1.0% HPMC | 340.6 | 90 | 1 | No change. |
| 1.25% HPMC | 1,000 | 90 | 1 | No change. |
| 1.5% HPMC | 2,000 | 100 | 1 | Slightly softer, lacks "bounce". |
| 2.0% HPMC | 4,000 | 100 | 1 | Slightly softer, lacks "bounce". Slippery. |

(C)

| Sample | % Transmission @ 650 nm |
|---|---|
| 0.10M phosphate buffer, pH 7.80 | 100.0% |
| 10% PVP | 99.9% |
| 1.5% HPMC | 95.7% |
| 1.0% HPMC | 96.8% |
| 0.5% HPMC | 99.1% |
| 0.1% HPMC | 99.6% |

Hydrogel Surface Spread Test Categories:
1) No spreading, tight drops that stay in place;
2) Mild spreading, drops drip slowly down;
3) Severe spreading, drops completely wet surface. Water is in category 3.

Methylcellulose (MC) was found to behave similarly to hypromellose (HPMC) and provided workable viscous solutions in the concentration range of 0 to 2% (w/w). However, the HPMC dissolved more readily than the MC, and the HPMC solutions possessed greater optical clarity; thus the use of HPMC was favored. Povidone (PVP) dissolved easily in the buffer, but provided minimal viscosity enhancement even at 20% (w/w). Higher molecular weight grades of PVP are available, but have not yet been explored.

For the most part, the polymers remain unchanged by the addition of low concentrations of HPMC or PVP. However, there was a noticeable change in the polymer around 0.3% HPMC that was characterized by an enhanced elasticity, as evidenced by the ability of the material to elongate more than usual without breakage. Above 1.5% HPMC, the polymer became slightly softer and exhibited less bounce. The gel times also remained within 10 seconds of the gel time for the formulation with no viscous agent. In the case of PVP, significant changes in the polymer occurred above 10% PVP. The polymer became more opaque with a noticeable increase in elasticity and stickiness. At 15% to 20% PVP, the polymer became similar to the sticky materials, but with a better mechanical strength. The gel times also increased by roughly 20 seconds relative to the formulation with no viscous agent. Thus, the addition of lower concentrations of PVP or HPMC to the polymer solutions may be beneficial in improving the polymer's elasticity and lubricity.

The results of the hydrogel surface spread test show that most formulations belong in category 2.

Based on the these observations, a formulation utilizing 0.3% HPMC was chosen for further evaluation. Above 1.0% HPMC, the solutions became significantly more difficult to mix and dissolution of the monomers became an issue. At 0.5% HPMC and above, the formation of air bubbles during mixing became significant. Furthermore, the solutions were not easily filtered through a 0.5 μm syringe filter to remove the bubbles. However, the 0.3% HPMC solution was easily filtered even after moderate mixing, resulting in a bubble-free, optically clear polymer.

Viscosity Measurements

The viscosities of the resulting buffer solutions were measured with the appropriately sized Cannon-Fenske viscometer tube from Ace Glass. Viscometer sizes used ranged from 25 to 300. Measurements of select solutions were performed in triplicate at both 20° C. and 37° C. The results are shown in Table 9B. To calculate the approximate dynamic viscosities, it was assumed that all the buffer solutions had the same density as water.

To characterize the rheology of the polymers during the gelation process, a size 300 viscometer was used with a formulation that was designed to gel after approximately 15 minutes. The formulation used involved the 8ARM-20k-NH2 with the 4ARM-20k-SGA ester at 2.5% solution and 0.3% HPMC. The reaction occurred in a 0.05 M phosphate buffer at a pH of 7.2. Thus, one viscosity measurement with the size 300 viscometer was obtained in about one minute and subsequent measurements may be obtained in quick succession up to the gel point.

Hydro Gel Surface Spread Test

To model the performance of the polymer solutions on a hydrophilic surface the extent of spreading and dripping of droplets on a high water content hydrogel surface at an incline of about 30° was recorded. The hydrogel was made by dissolving 0.10 g (0.04 mol arm eq.) of 8ARM-20k-NH2 in 7 mL 0.05 M phosphate buffer at pH 7.4 in a Petri-dish, followed by the addition of 0.075 g (0.04 mol arm eq.) of 8ARM-15k-SG ester. The solution was stirred with a spatula for 10 to 20 seconds and allowed to gel, which typically took 5 to 10 minutes. The water content of the resulting polymer was 97.5%.

The test was performed by first preparing the polymer solution in the usual fashion. After thorough mixing, the polymer solution was dispensed dropwise through a 22 gauge needle onto the hydrogel surface. The results are shown in Table 9B and were divided into three general categories: 1) no spreading, tight drops that stay in place; 2) mild spreading, drops drip slowly down; 3) severe spreading, drops completely wet surface. Water is in category 3.

Swelling & Drying Measurements

The extent of swelling in the polymers during the degradation process was quantified as the liquid uptake of the polymers. A known mass of the polymer was placed in PBS at 37° C. At specified time intervals, the polymer was isolated from the buffer solution, patted dry with paper towels and weighed. The percent increase in the mass was calculated from the initial mass.

The fate of the polymers in air under ambient conditions was quantified as the weight loss over time. A polymer film of about 1 cm thickness was placed on a surface at 20° C. Mass measurements were performed at set intervals. The percent weight loss was calculated from the initial mass value.

The percent of water uptake by the 8ARM-20k-NH2/4ARM-20k-SGA polymers with 0, 0.3 and 1.0% HPMC was measured. The 1.0% HPMC polymer absorbed up to 30% of its weight in water until day 20. After day 20, the polymer returned to about 10% of its weight in water. In comparison, the 0% HPMC polymer initially absorbed up to 10% of its weight in water, but began to lose water gradually, hovering about 5% of its weight in water. The 0.3% HPMC polymer behaved in an intermediate fashion. It initially absorbed up to 20% of its weight in water, but returned to about 10% of its weight in water after a week and continued to slowly lose water.

Figure 4:
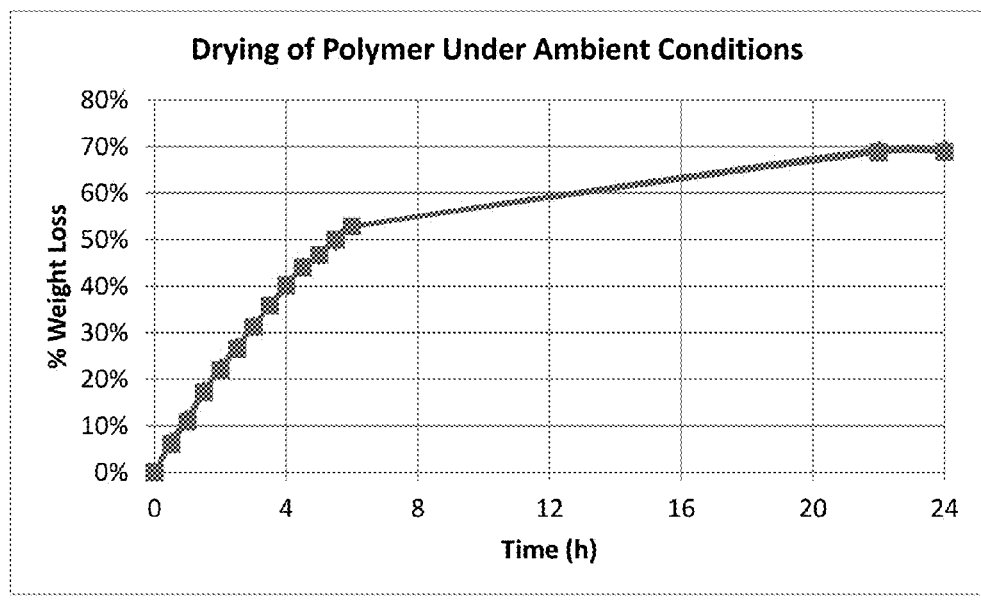
FIG. 4 shows the effect of the polymer of Example 13A left in the air as the percent of water weight loss over time.

The percent of weight loss under ambient conditions over 24 hours by the 8ARM-20k-AA/8ARM-20k-NH2 (75/25) & 4ARM-20k-SGA polymer with 0.3% HPMC and 1.0% HPMC is shown in FIG. 4. Ambient conditions were roughly 20° C. and 30 to 50% relative humidity. The rate of water loss was fairly constant over 6 hours at about 10% per hour. After 6 hours, the rate slowed significantly as the polymer weight approached a constant value. The rate of water loss is expected to vary based on the polymer shape and thickness, as well as the temperature and humidity.

Specific Gravity Measurements

The specific gravity of the polymers was obtained by preparing the polymer solution in the usual fashion and pipetting 1.00 mL of the thoroughly mixed solution onto an analytical balance. The measurements were performed in triplicate at 20° C. The specific gravity was calculated by using the density of water at 4° C. as the reference.

The specific gravity of the polymers did not differ significantly from that of the buffer solution only, both of which were essentially the same as the specific gravity of water. Exceptions may occur when the polymer solution is not filtered and air bubbles become embedded in the polymer matrix.

Barium Sulfate Suspensions

For imaging purposes, barium sulfate was added to several polymer formulations as a radiocontrast agent. Barium sulfate concentrations of 1.0, 2.0, 5.0 and 10.0% (w/v) were explored. The viscosity of the resulting polymer solutions was measured and the effect of barium sulfate addition on the polymer gel times and syringability characteristics were also studied.

Barium sulfate concentrations of 1.0, 2.0, 5.0 and 10.0% (w/v) were explored. The opaque, milky white suspensions formed similarly opaque and white polymers. No changes in the gel times were observed. Qualitatively, the polymers appeared to have similar properties to that of polymers without barium sulfate. All formulations were able to be readily dispensed through a 22 gauge needle.

The viscosity barium sulfate concentrations of 1.0, 2.0, 5.0 and 10.0% remained relatively stable up to 2.0%; at 5.0%, the viscosity increased slightly to about 2.5 cP. There was a sharp increase in the viscosity to nearly 10 cP as the concentration approached 10.0%. Thus, a barium sulfate concentration of 5.0% was chosen as a balance between high contrast strength and similarity to unmodified polymer formulations.

Hydrogel Firmness, Elastic Modulus, and Adhesion

Figure 5:
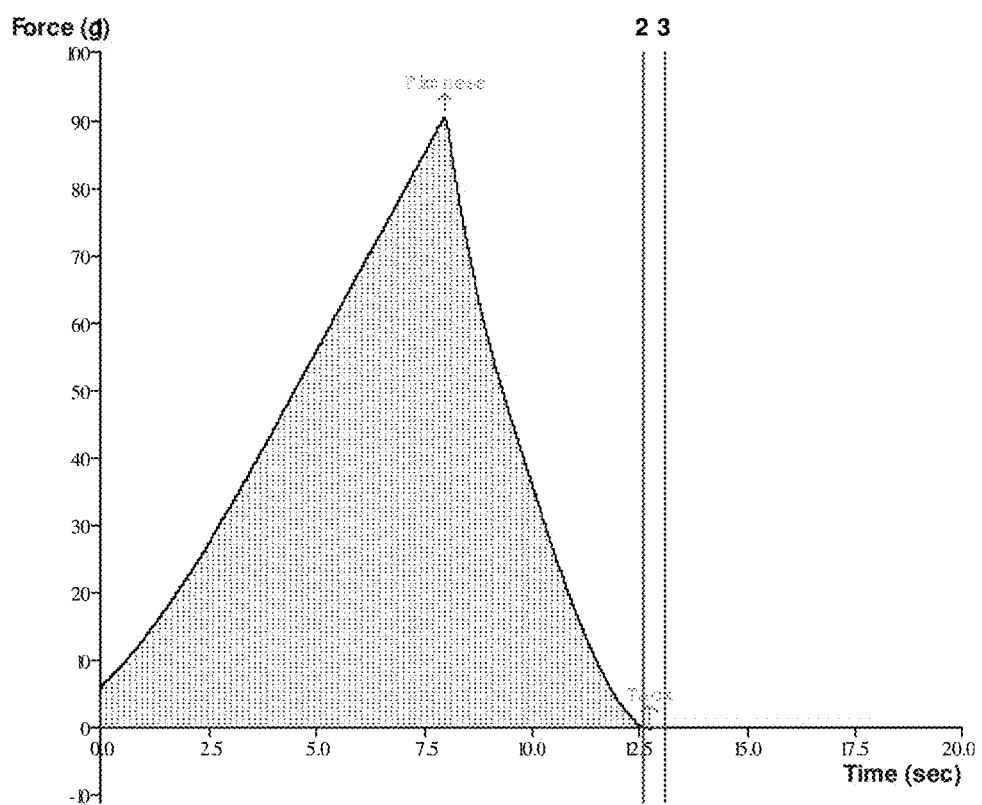
FIG. 5 shows a sample plot generated by the Texture Analyzer Exponent software running the firmness test. The peak force was recorded as the polymer firmness, which represents the point where the target penetration depth of 4 mm has been reached by the probe.

The firmness of the polymers was characterized by a Texture Analyzer model TA.XT.plus with Exponent software version 6.0.6.0. The method followed the industry standard "Bloom Test" for measuring the firmness of gelatins. In this test, the TA-8¼" ball probe was used to penetrate the polymer sample to a defined depth and then return out of the sample to the original position. The peak force measured is defined as the "firmness" of the sample. For the polymers studied, a test speed of 0.50 mm/sec, a penetration depth of 4 mm, and a trigger force of 5.0 g were used. The polymers were prepared on a 2.5 mL scale directly in a 5 mL size vial to ensure consistent sample dimensions. The vials used were ThermoScientific/Nalgene LDPE sample vials, product#6250-0005 (LOT#7163281060). Measurements were conducted at 20° C. The polymers were allowed to rest at room temperature for approximately 1 hour before measuring. Measurements were performed in triplicate for at least three samples. A sample plot generated by the Exponent software running the firmness test is given in FIG. 5. The peak of the plot represents the point at which the target penetration depth of 4 mm was reached.

Figure 6:
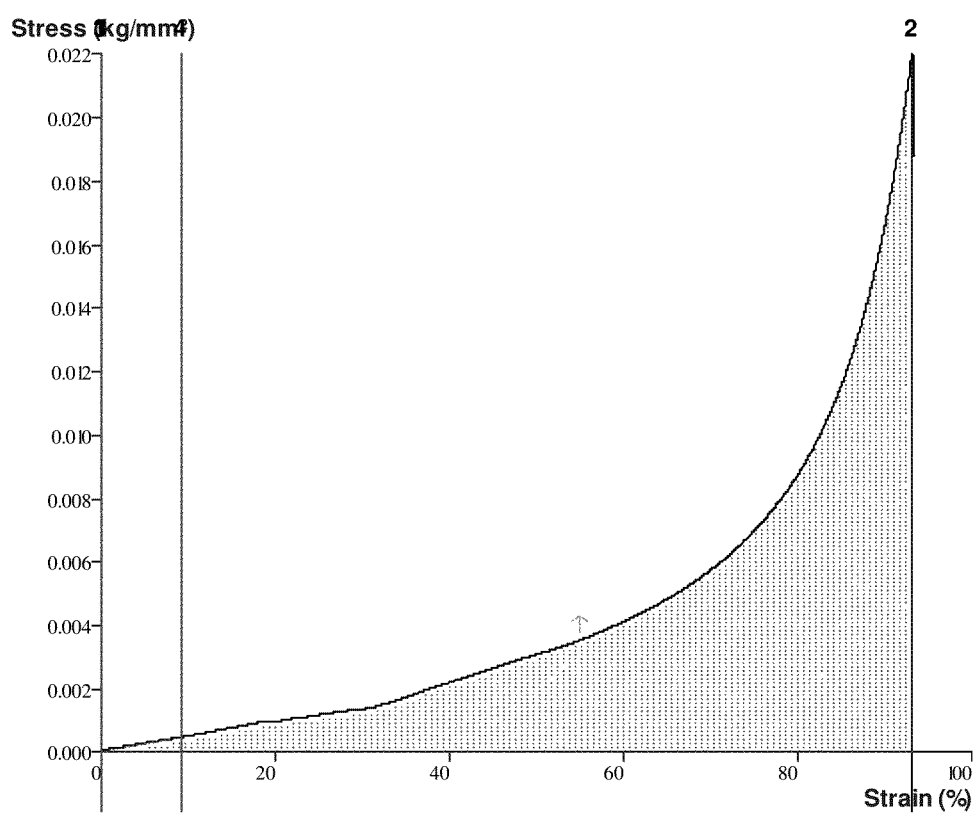
FIG. 6 shows a sample plot generated by the Texture Analyzer Exponent software running the elastic modulus test under compression. The modulus was calculated from the initial slope of the curve up to 10% of the maximum compression stress.

The elastic modulus of the polymers was characterized by a Texture Analyzer model TA.XT.plus with Exponent software version 6.0.6.0. In this test, the TA-19 Kobe probe was used to compress a polymer cylinder of known dimensions until fracture of the polymer occurs. The probe has a defined surface area of 1 cm². The modulus was calculated as the initial slope up to 10% of the maximum compression stress. For the polymers studied, a test speed of 5.0 mm/min and a trigger force of 5.0 g were used. The sample height was auto-detected by the probe. The polymers were prepared on a 2.5 mL scale directly in a 5 mL size vial cap to ensure consistent sample dimensions. The vials used were ThermoScientific/Nalgene LDPE sample vials, product#6250-0005 (LOT#7163281060). Measurements were conducted at 20° C. The polymers were allowed to rest at room temperature for approximately 1 hour before measuring. Measurements were performed for at least three samples. A sample plot generated by the Exponent software running the modulus test is given in FIG. 6. The polymers typically behaved elastically for the initial compression, as evidenced by the nearly linear plot.

Figure 7:
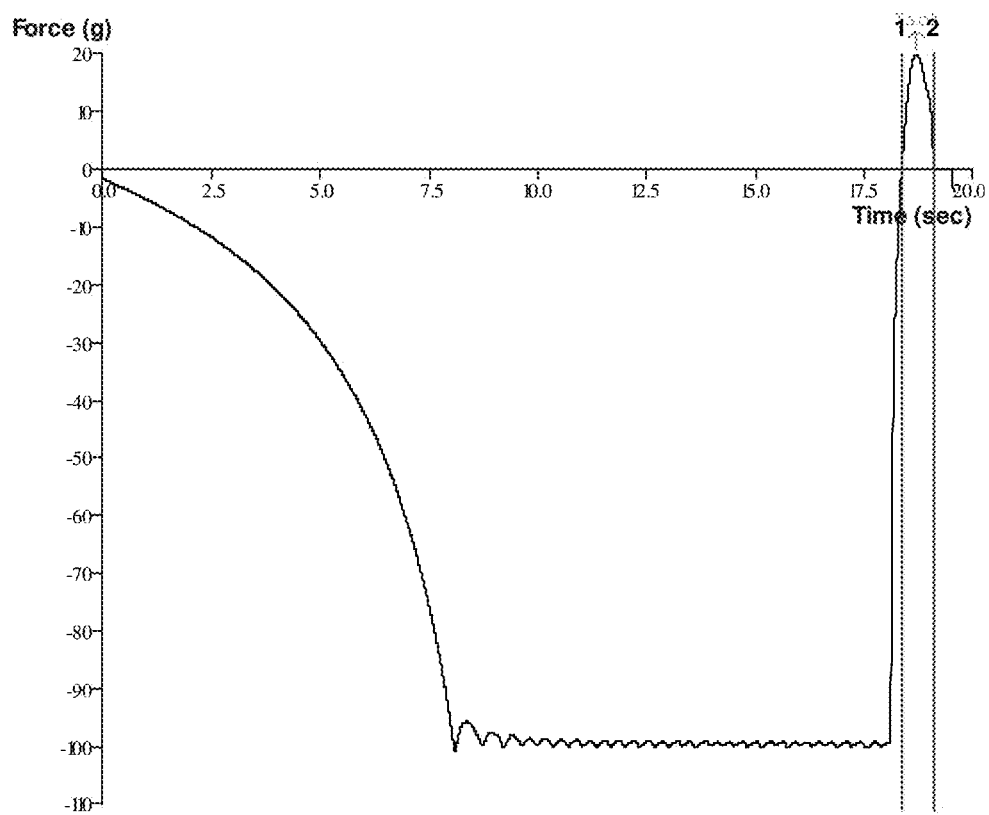
FIG. 7 shows an exemplary plot generated by the Texture Analyzer Exponent software running the adhesion test. A contact force of 100.0 g was applied for 10 seconds. The tack was measured as the peak force after lifting the probe from the sample. The adhesion energy or the work of adhesion was calculated as the area under the curve representing the tack force (points 1 to 2). The stringiness was defined as the distance traveled by the probe while influencing the tack force (points 1 and 2).

The adhesive properties of the polymers were characterized by a Texture Analyzer model TA.XT.plus with Exponent software version 6.0.6.0. In the adhesive test, the TA-57R 7 mm diameter punch probe was used to contact the polymer sample with a defined force for a certain amount of time, and then return out of the sample to the original position. An exemplary plot generated by the Exponent software running the adhesive test is given in FIG. 7. The plot begins when the probe hits the surface of the polymer. The target force is applied on the sample for a defined unit of time, represented by the constant force region in the plot. Then, the probe returns out of the sample to the original position and the adhesive force between the probe and the sample is measured as the "tack", which is the peak force required to remove the probe from the sample. Other properties that were measured include the adhesion energy or the work of adhesion, and the material's "stringiness." The adhesion energy is simply the area under the curve representing the tack force. Thus, a sample with a high tack and low adhesion energy will qualitatively feel very sticky, but may be cleanly removed with a quick pull; a sample with a high tack and high adhesion energy will also feel very sticky, but the removal of the material will be more difficult and may be accompanied by stretching of the polymer, fibril formation and adhesive residues. The elasticity of the polymer is proportional to the measured "stringiness", which is the distance the polymer stretches while adhered to the probe before failure of the adhesive bond. For the polymers studied, a test speed of 0.50 mm/sec, a trigger force of 2.0 g, and a contact force of 100.0 g and contact time of 10.0 sec were used. The polymers were prepared on a 1.0 to 2.5 mL scale directly in a 5 mL size vial to ensure consistent sample surfaces. The vials used were ThermoScientific/Nalgene LDPE sample vials. Measurements were conducted at 20° C. The polymers were allowed to rest at room temperature for approximately 1 hour before measuring. As reference materials, the adhesive properties of a standard Post-It Note® and Scotch Tape® were measured. All measurements were performed in triplicate. The averages and standard deviations were calculated.

Figure 8A:
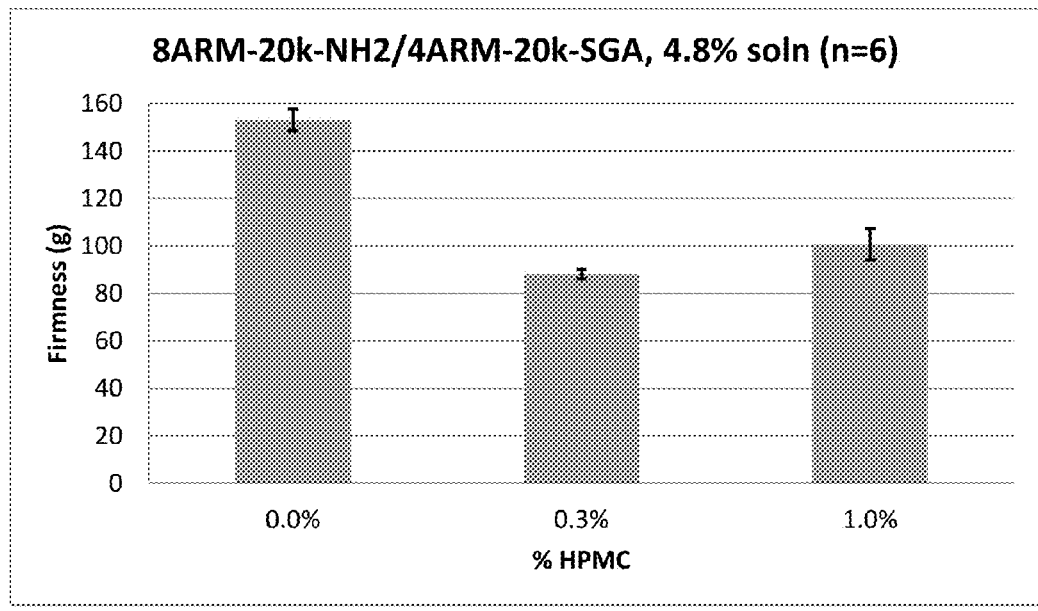
FIG. 8A-8B shows the effect of hypromellose (HPMC) addition at 0, 0.3 and 1.0% to the polymer formulations on firmness (8A). Effect of degradable acetate amine 8ARM-20k-AA addition at 0, 70 and 100% to the polymer formulations on firmness (8B).

The effect of HPMC addition to the mechanical properties of the polymers was explored, along with the effect of adding degradable 8ARM-20k-AA amine. The results are shown in FIGS. 8A-8B and FIGS. 9A-9B. Under the stated conditions of the firmness test, it was found that the addition of 0.3% HPMC decreased the firmness of the polymer by about half (FIG. 8A). This corresponds to a slight decrease in the elastic modulus (FIG. 9A). The 1.0% HPMC polymer had approximately the same firmness as the 0.3% HPMC polymer, but a slight decrease in the elastic modulus. The disparity between the firmness and modulus tests is likely due to experimental error. The polymer solutions were not filtered, so the presence of air bubbles likely increased the errors. The water content of the polymers may also change as the polymers were sitting in the air, essentially changing the physical properties of the materials.

Figure 8B:
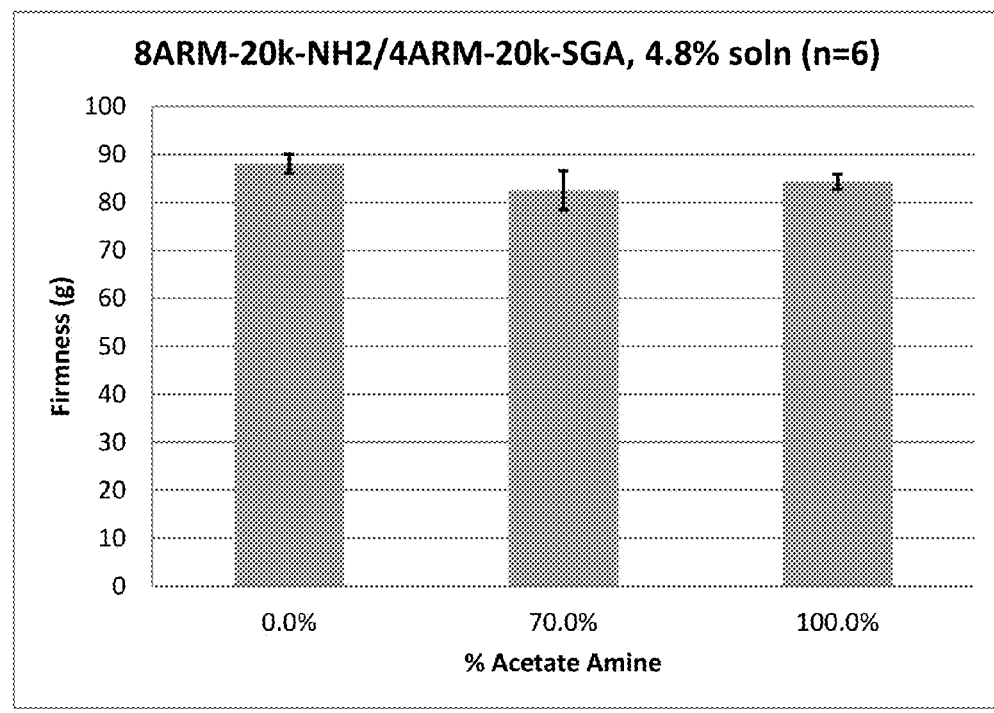
Figure 9A:
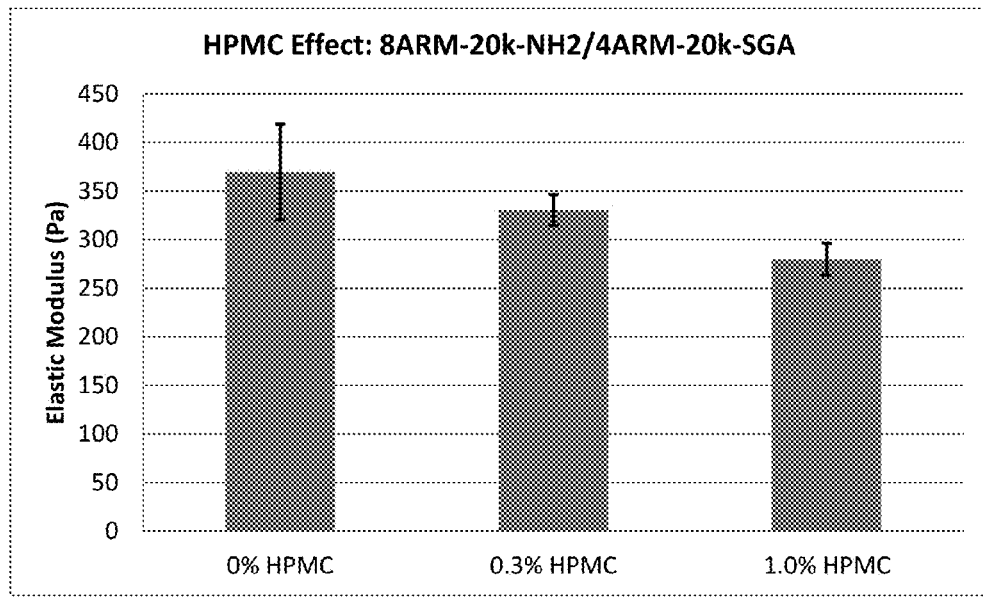
FIGS. 9A-9B shows the effect of hypromellose (HPMC) addition at 0, 0.3 and 1.0% to the polymer formulations on the elastic modulus (9A) and shows the effect Effect of degradable acetate amine 8ARM-20k-AA addition at 0, 70 and 100% to the polymer formulations on the elastic modulus (9B).
Figure 9B:
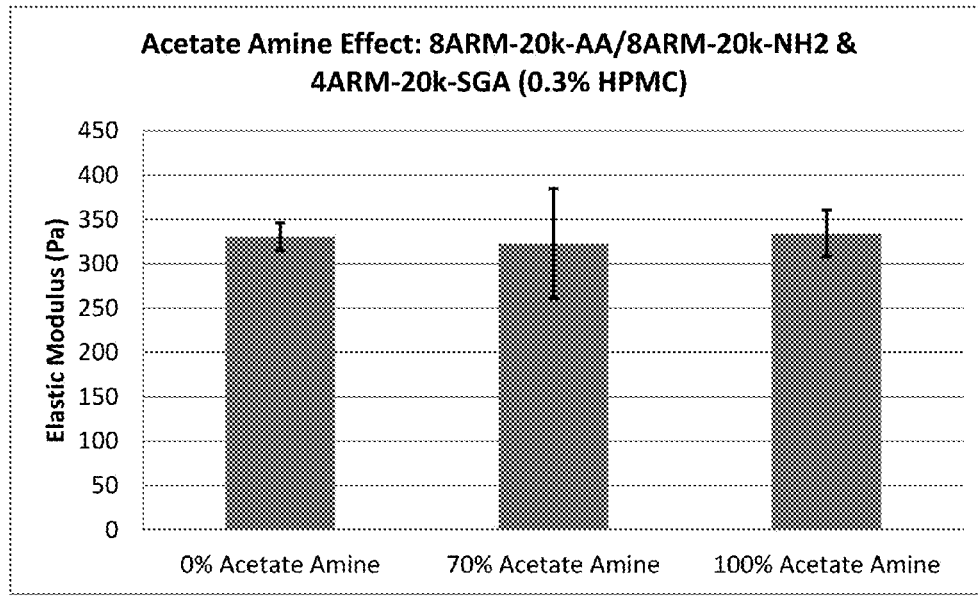
Figure 10A:
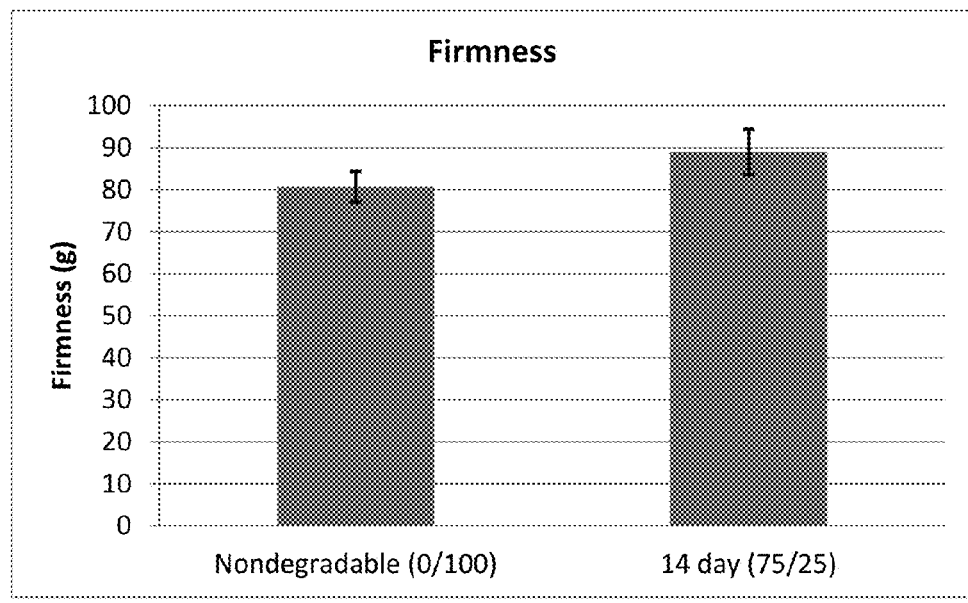
Figure 10B:
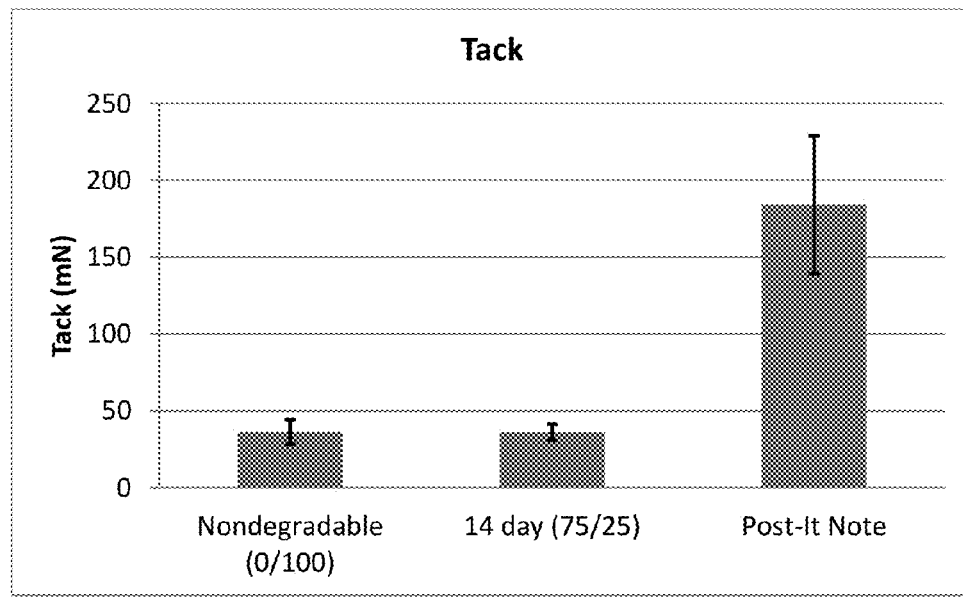

It was found that the addition of the degradable 8ARM-20k-AA amine did not substantially change the measured values of the firmness or the elastic modulus (FIG. 8B and FIG. 9B). The results of the adhesion testing are shown in FIG. 10A-10D. The measured values for a standard commercial Post-It™ Note are also included as a reference. The polymer tack was found to be around 40 mN, which is about three times less than that of a Post-It™ Note. The adhesive properties of the polymer were not found to vary with the addition of the degradable amine.

Figure 11:
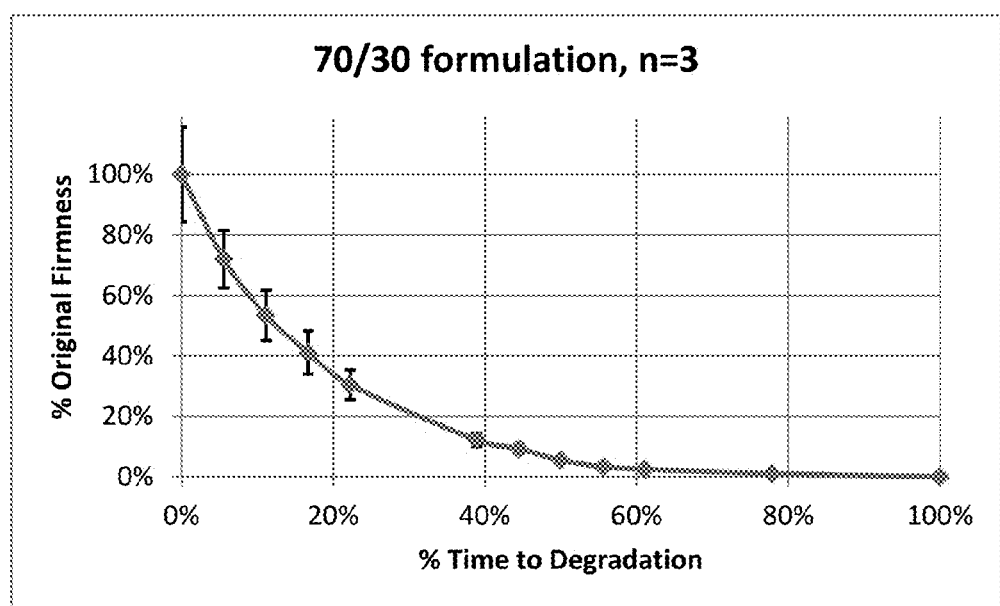
FIG. 11 shows the firmness vs. degradation time plotted as percentages for the polymer formulation: 8ARM-20k-AA/8ARM-20k-NH2 (70/30) & 4ARM-20k-SGA at 4.8% solution with 0.3% HPMC. The error bars represent the standard deviations of 3 samples. The degradation time for the polymer was 18 days.
Figure 12A:
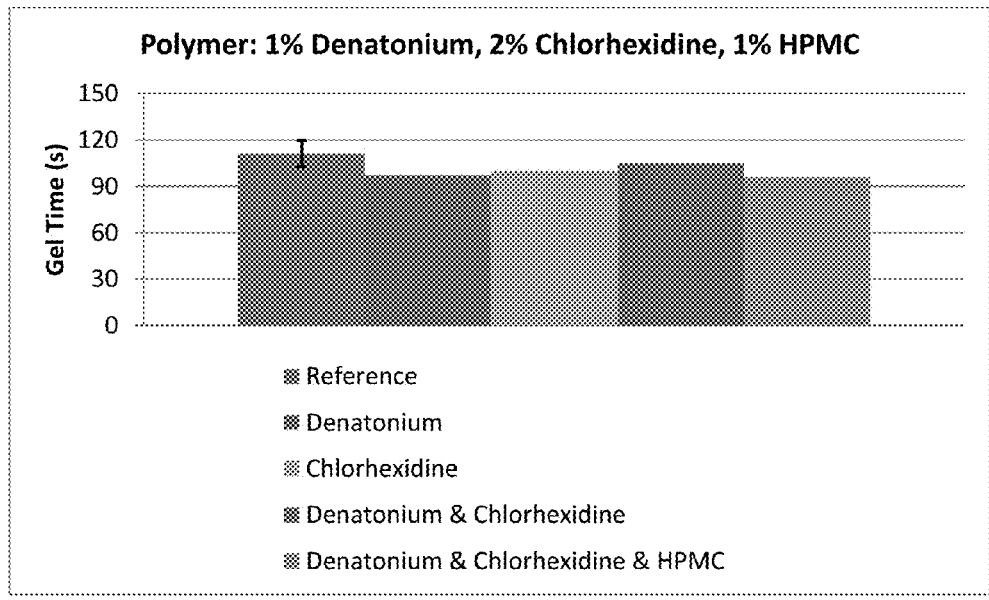
FIGS. 12A-12E shows the effect of additives on the polymer gel time (12A), degradation time (12B), firmness (12C), adhesion (12D) and elastic modulus (12E).
Figure 12B:
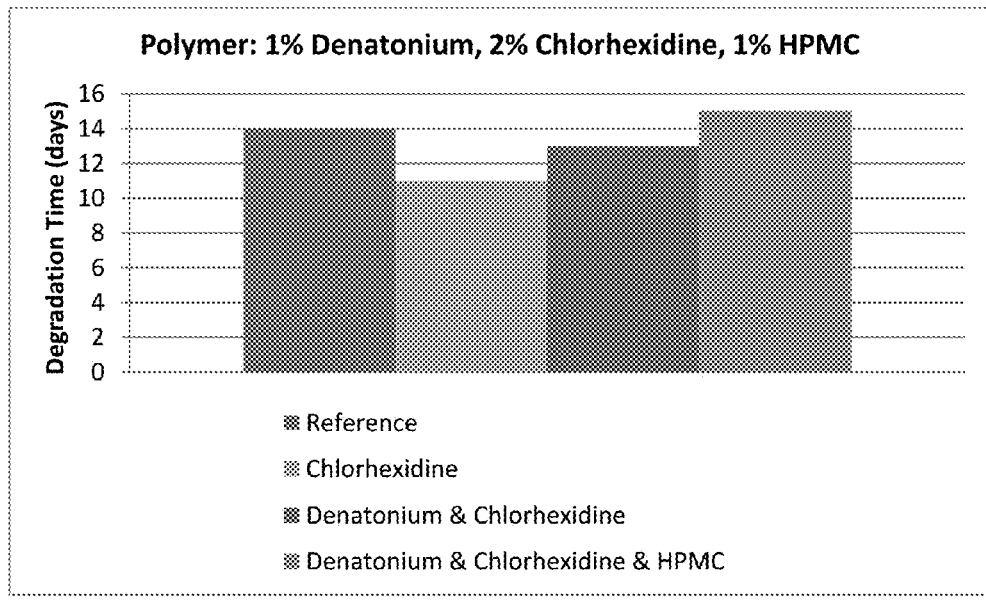
Figure 12C:
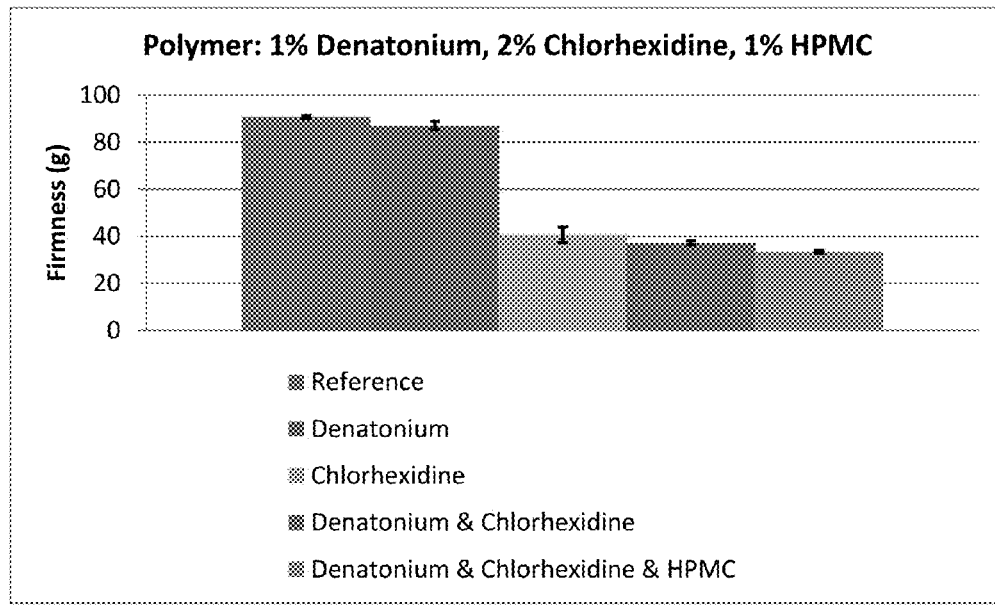
Figure 12D:
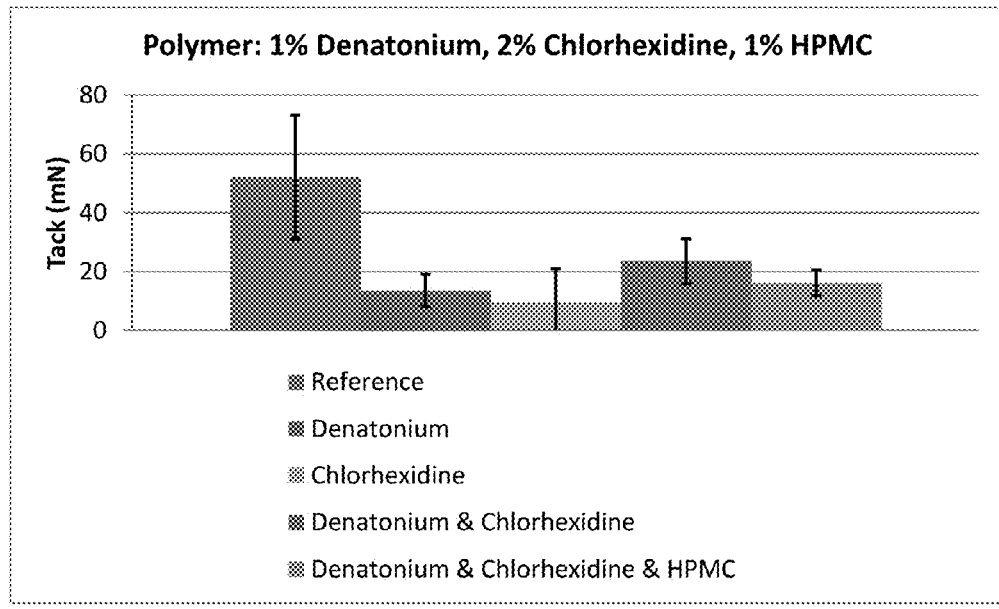
Figure 12E:
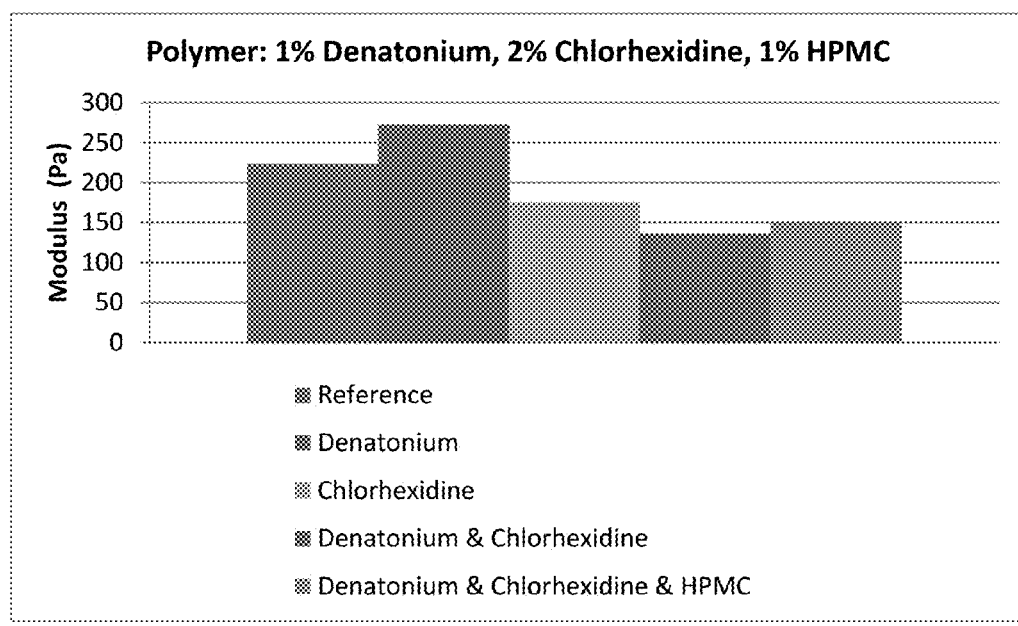

FIG. 11 shows the firmness vs. degradation time for the 8ARM-20k-AA/8ARM-20k-NH2 (70/30) & 4ARM-20k-SGA at 4.8% solution with 0.3% HPMC. The error bars represent the standard deviations of 3 samples. The degradation time for the polymer was 18 days. The firmness of the polymer strongly correlated with the extent of degradation. Swelling may also play a role during the early stages.

The effect of various additives to the formulation on the polymer properties was explored. FIG. 12A-12E shows the gel time, degradation time, firmness, adhesion and elastic modulus for polymers prepared with varying combinations of 1% HPMC, 2% chlorhexidine and 1% denatonium benzoate. Essentially no change in the polymer properties were found except for formulations containing 2% chlorhexidine, which exhibited decreased firmness and elastic modulus. It was apparent from visual inspection of the polymer that the change was due to the detergent present in the Nolvasan solution used and not the chlorhexidine; the detergent caused heavy foaming during mixing that gelled into an aerated polymer.

Figure 13A:
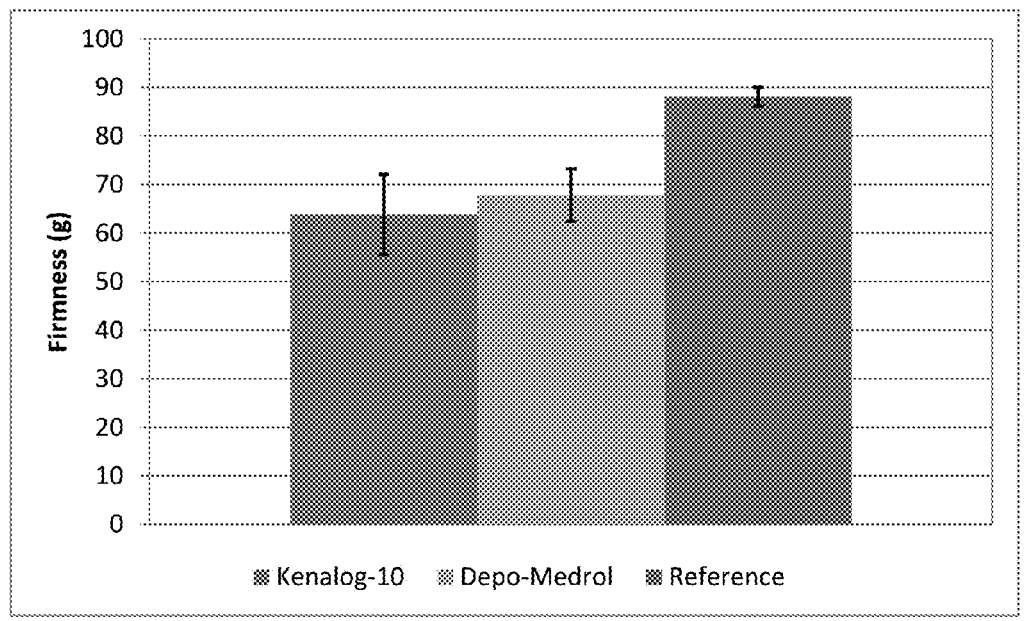
FIGS. 13A-13C shows the effect of using Kenalog-10 or Depo-Medrol with the single syringe system on the polymer firmness (13A), adhesion (13B) and elastic modulus (13C).
Figure 13B:
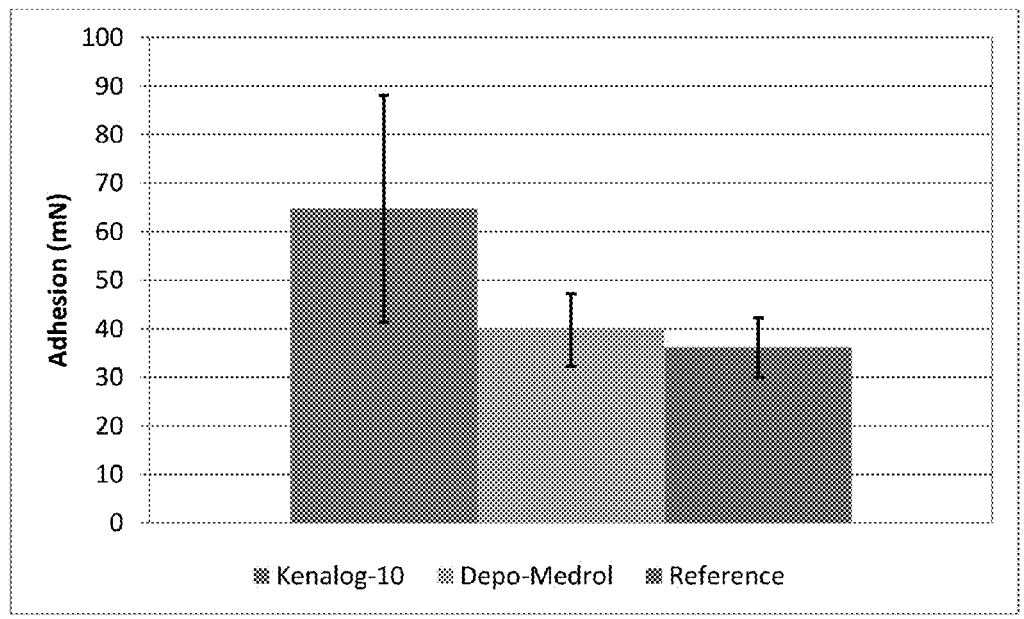
Figure 13C:
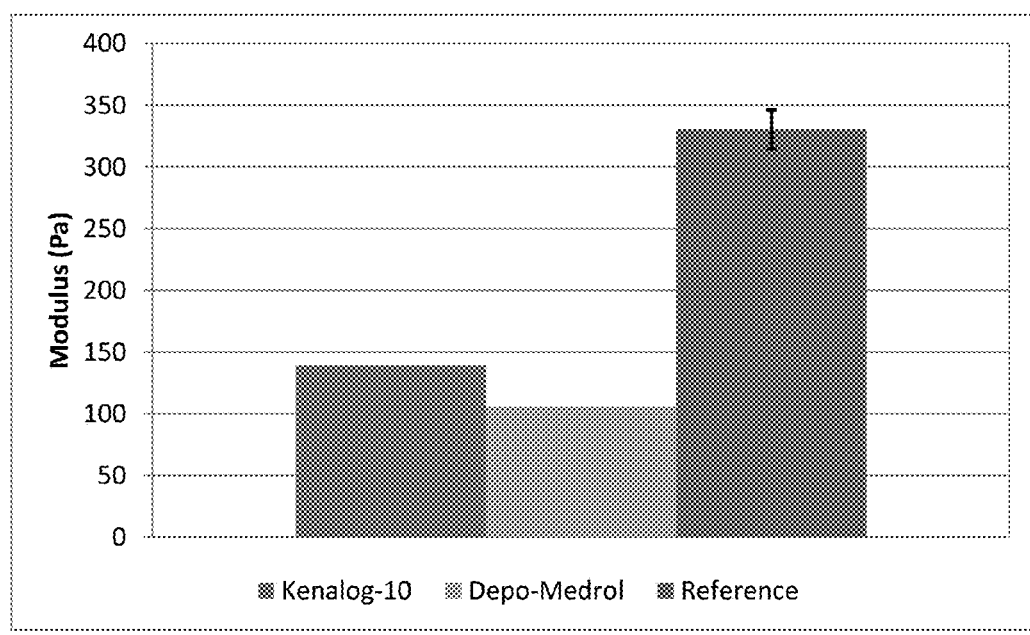

FIG. 13A-13C shows the effect of using Kenalog-10 or Depo-Medrol drug solutions with the single syringe system on the polymer properties. The drug loaded polymers are slightly softer and more elastic relative to the reference, presumably due to the presence of viscosity enhancers in the drug solutions.

Optical Clarity

A Thermo Scientific GENESYS 10S UV-Vis spectrophotometer was used to measure the optical clarity of the viscous solutions. To a quartz cuvette, 1.5 mL of the sample solution was pipetted. The buffer solution with no additives was used as the reference. The stable % transmission of the sample was recorded at 650 nm and the results are listed in Table 9C.

To measure the light transmission of the polymers, 1 mL of polymer solution was filtered with a 5 μm filter into a cuvette before gelation. The cuvette was then placed horizontally so that the polymer gelled on the side of the cuvette as a film. The film thickness was found to be 3 mm. The polymer was allowed to cure for 15 minutes at room temperature before measuring the % light transmission at 400, 525 and 650 nm with air as the reference.

All of the viscous solutions under consideration were found to have acceptable to excellent optical clarity under the concentration ranges used (greater than 97% transmission). For the highly viscous solutions, air bubble formation during mixing was observed, which may be resolved by the addition of an anti-foaming agent, or through the use of a syringe filter (See Table 9C).

Figure 14:
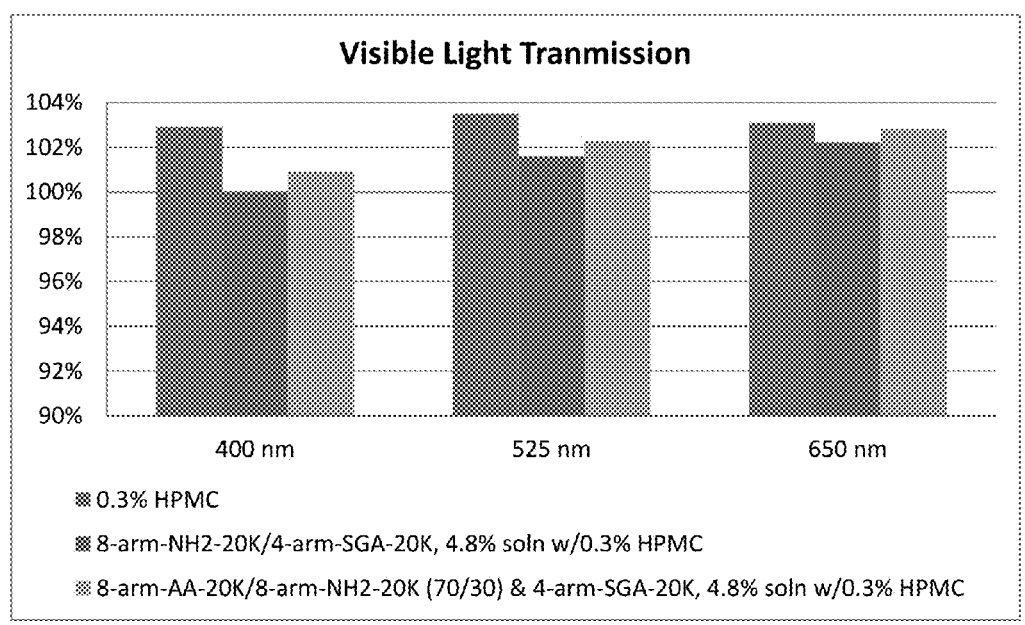
FIG. 14 shows the optical clarity of 3 mm thick polymer slices, as measured by the % transmission at 400, 525 and 650 nm.

The polymers exhibited excellent optical clarifies over the visible spectrum. The lowest % transmission relative to buffer only was 97.2% and the highest was 99.7%. The drop in the % transmission at lower wavelengths is likely due to some energy absorption as the ultraviolet region is approached. The results are shown in FIG. 14.

Drug Elution: General Procedures

A Thermo Scientific GENESYS 10S UV-Vis spectrophotometer was used to quantify the release of various drugs from several polymers. First, the reference drug or drug solution was dissolved in an appropriate solvent. Typically, phosphate buffered saline (PBS), ethanol or dimethylsulfoxide (DMSO) were used as the solvent. Next, the optimal absorption peak for identifying and quantifying the drug was determined by performing a scan of the drug solution between 200 and 1000 nm. With the absorption peak selected, a reference curve was established by measuring the peak absorbance for various concentrations of the drug. The different drug concentration solutions were prepared by standard dilution techniques using analytical pipettes. A linear fit of the absorbance vs. drug concentration resulted in a general equation that was used to convert the measured absorbance of the elution samples to the drug concentration.

The polymer was prepared with a known drug dosage in the same fashion as a doctor administering the polymer in a clinical setting. However, in this case the polymer was molded into a cylinder with a diameter of approximately 18 mm. The polymer cylinder was then placed in a 50 mL Falcon tube with a set amount of PBS and placed at 37° C. The temperature was maintained by a digitally controlled water bath.

Elution samples were collected daily by decanting the PBS solution from the polymer. The volume of sample collected was recorded. The polymer was placed in a volume of fresh PBS equivalent to the volume of sample that was collected and returned to 37° C. The elution sample was analyzed by first diluting the sample in the appropriate solvent using analytical pipettes such that the measured absorbance was in the range determined by the reference curve. The dilution factor was recorded. The drug concentration was calculated from the measured absorbance via the reference curve and the dilution factor. The drug amount was calculated by multiplying the drug concentration with the sample volume. The percent elution for that day was calculated by dividing the drug amount by the total amount of drug administered.

Drug Elution: Chlorhexidine

The peak found between 255 and 260 nm was chosen and a reference curve was established by measuring the peak absorbance for 0, 0.5, 1, 2.5, 5, 10, 20, 40, and 50 ppm of chlorhexidine. Concentrations above 50 ppm did not exhibit linear behavior in peak absorbance.

The polymer was prepared with a commercial Nolvasan solution, which corresponds to a 2% chlorhexidine dose (50 mg). The elution volume was 2 mL of PBS per 1 g of polymer. The elution samples were stored at 20° C. The elution samples were analyzed by diluting the sample 1,000-fold with dimethyl sulfoxide (DMSO) in a quartz cuvette.

Figure 15:
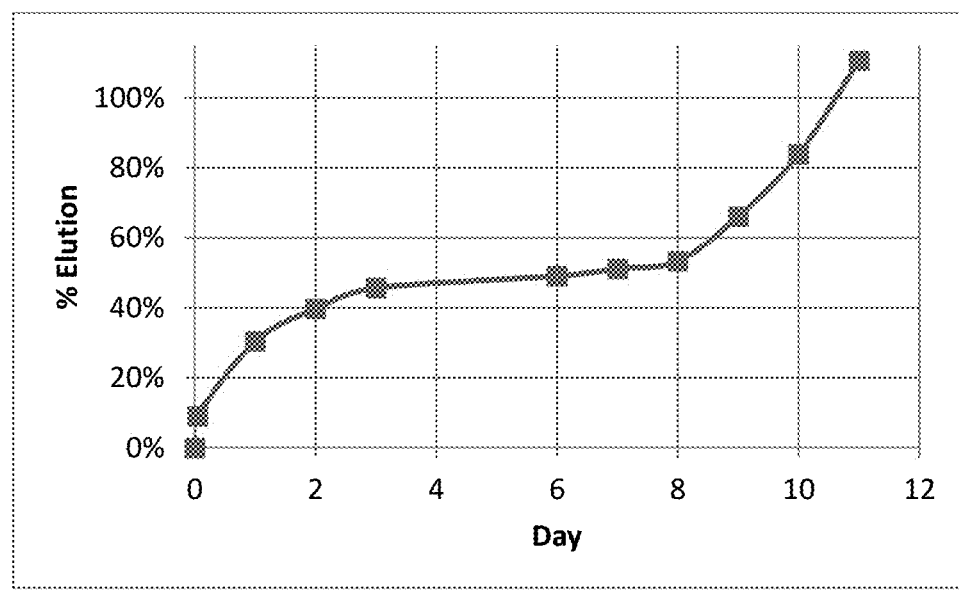
FIG. 15 shows for the polymer of Example 13A, the cumulative % elution of chlorhexidine.

The chlorhexidine elution behavior proceeded similarly to previous experiments with other small molecules. Almost half of the chlorhexidine was released within the first three days. Then, the elution rate slowed dramatically for the next three to four days followed by another large release of chlorhexidine as the polymer degrades (FIG. 15).

Drug Elution: Triamcinolone Acetonide (Kenalog)

The peak found between 235 and 245 nm was chosen and a reference curve was established by measuring the peak absorbance for 0, 0.002, 0.004, 0.008, 0.01, 0.04, 0.08 and 0.10 mg per mL of triamcinolone acetonide. Concentrations above 0.10 mg per mL did not exhibit linear behavior in peak absorbance.

The polymer was prepared with a commercial Kenalog-10 solution, which corresponds to a 10 mg per mL dose (20 mg). It should be noted that the commercial drug solution contained 0.9% of benzyl alcohol, which may interfere with the UV measurement at low concentrations of triamcinolone. However, it is significantly more soluble in PBS than the triamcinolone and was thus removed by leeching it out from the polymer with PBS at 37° C. for 2 to 4 hours. The solution was found to contain the majority of the contaminant and negligible amounts of drug by UV-Vis and was discarded. The elution volume was varied for different polymers and ranged from 2 mL of PBS per 1 g of polymer to 20 mL of PBS per 1 g of polymer. The elution samples were stored at 20° C. The elution samples were analyzed by diluting the sample with ethanol in a quartz cuvette by ½.

Drug Elution: Methylprednisolone Acetate (Depo-Medrol)

The peak found between 235 and 245 nm was chosen and a reference curve was established by measuring the peak absorbance for 0, 0.001, 0.002, 0.004, 0.005, 0.008, 0.01, 0.04, 0.05 and 0.08 mg per mL of methylprednisolone acetate. Concentrations above 0.08 mg per mL did not exhibit linear behavior in peak absorbance.

The polymer was prepared with a commercial Depo-Medrol solution, which corresponds to a 40 mg per mL dose (80 mg). It should be noted that the commercial drug solution contained 0.0195% of myristyl-gamma-picolinium chloride, which may interfere with the UV measurement at low concentrations of methylprednisolone. However, it is significantly more soluble in PBS than the methylprednisolone and was thus removed by leeching it out from the polymer with PBS at 37° C. for 2 to 4 hours. The solution was found to contain the majority of the contaminant and negligible amounts of drug by UV-Vis and was discarded. The elution volume was 2 mL of PBS per 1 g of polymer. The elution samples were stored at 20° C. The elution samples were analyzed by diluting the sample with ethanol in a quartz cuvette, typically by 1/5 or 1/10.

Figure 16:
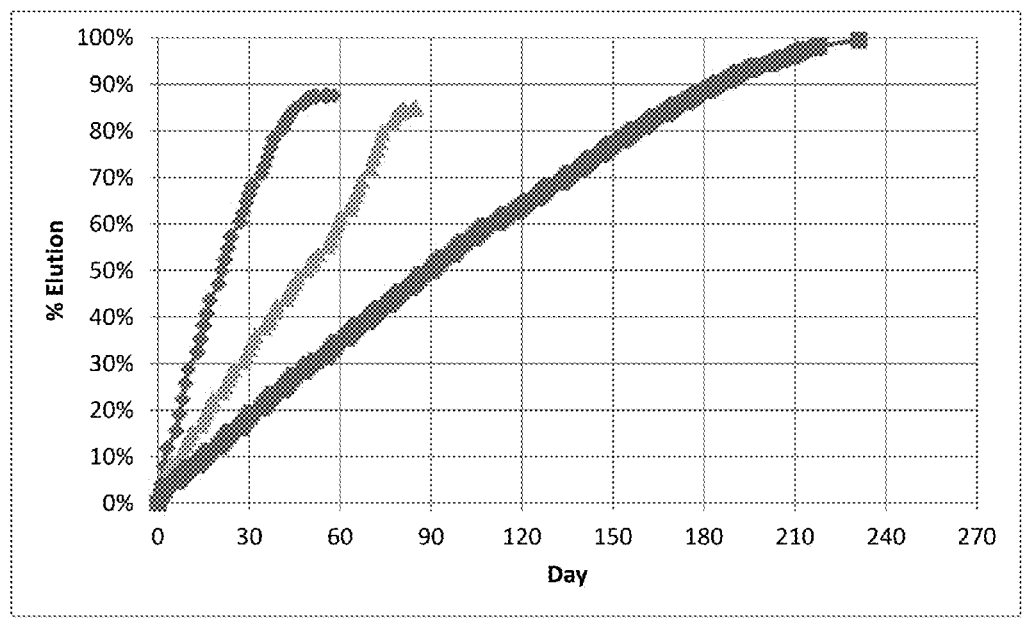
FIG. 16 shows that for the polymer of Example 13B, the triamcinolone cumulative % elution for 60, 90 and 240 day polymers.
Figure 17:
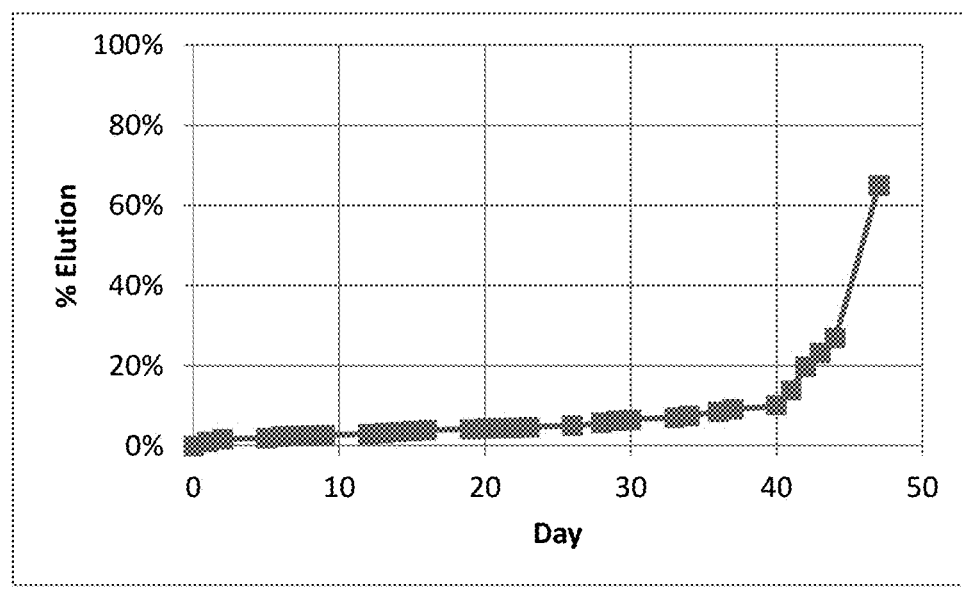
FIG. 17 shows that for short degradation time version of the polymer of Example 13B loaded with Depo-Medrol, the methylprednisolone cumulative % elution.
Figure 18:
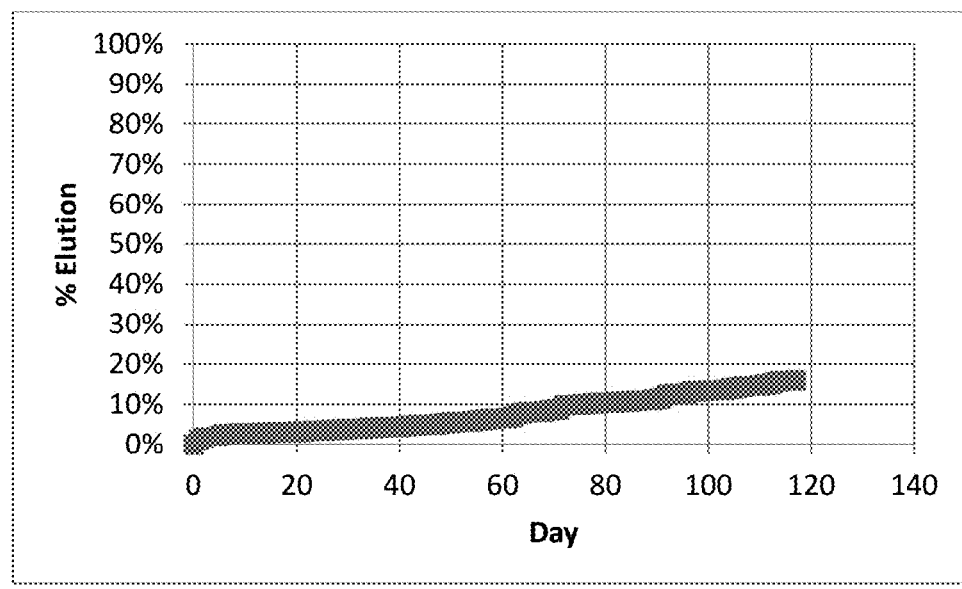
FIG. 18 shows that for long degradation time version of the polymer of Example 13B loaded with Depo-Medrol, the methylprednisolone cumulative % elution.

The elution of the steroidal drugs, triamcinolone and methylprednisolone, behaved similarly. The first few days typically exhibit an elevated elution rate, presumably as weakly bound surface drug is released. Then, the elution is relatively constant at a rate that is related to the drug solubility. Finally, the remaining drug in the polymer is released as degradation begins. Several examples are given in FIG. 16, FIG. 17, and FIG. 18 of the control over the elution behavior that was developed. Drugs may be released over a short time (weeks) or long period (years, projected).

Drug Elution: Kinetic Measurements

Several experiments were performed with Kenalog-10 loaded polymers to obtain a better understanding of the elution behavior. The polymer and a separate PBS solution were first equilibrated to 37° C. At a specified initial time point, the polymer was added to the PBS solution. Measurements were performed at specific time intervals for up to 3 days. The drug concentrations and amounts over time were plotted and analyzed.

Several preliminary experiments were performed with Kenalog-10 loaded polymers to obtain a better understanding of the elution behavior. In summary, 0th order release kinetics was observed, presumably due to the low solubility of the drug. The measured rate constant was 2.90±0.08 μg per mL per hour (37° C. in PBS). After around 16 hours, the solution becomes saturated with the drug and drug release is greatly retarded until the solution is refreshed.

Furthermore, recent experiments suggest that the shape of the polymer may play a role in drug elution behavior, especially at later stages. It was observed that the drug was released from the polymer beginning at the outer layers. As the outer layers become depleted, the remaining drug at the center of the polymer was observed to elute at a slightly slower rate.

Example 12

General Procedure for the Preparation of Polymerizable Pre-Formulations

Several representative formulations for both sticky and non-sticky films are listed in Table 10 along with specific reaction details. The films had thicknesses ranging from 100 to 500 μm, and may be layered with different formulations in a composite film.

TABLE 10

(A) Summary of the reaction details for several representative thin film formulations; (B) more detailed tabulation of a selection of the reaction details including moles (films ranged in thickness from 100 to 500 μm).

(A)

| Components | Amine/Ester Molar Ratio | Buffer | % Solution |
|---|---|---|---|
| 4ARM-20k-AA & 8ARM-15k-SG | 1 | 0.15M phosphate, pH 7.99 | 19.6 |
| 4ARM-5k-NH2 & 4ARM-10k-SG | 4.5/1 | 0.05M phosphate, pH 7.40 | 39 |
| 4ARM-5k-NH2 & 4ARM-10k-SG | 1 | 0.05M phosphate, pH 7.40 | 36.4 |
| 4ARM-5k-NH2 & 4ARM-10k-SG & HPMC (1.25%) | 4.5/1 | 0.10M phosphate, pH 7.80 | 39 |
| 4ARM-2k-NH2 & 4ARM-10k-SG & HPMC (1.5%) | 8/1 | 0.10M phosphate, pH 7.80 | 30.6 |
| 4ARM-2k-NH2 & 4ARM-20k-SGA & MC (2%) | 8/1 | 0.15M phosphate, pH 7.94 | 30 |
| 4ARM-2k-NH2 & 4ARM-20k-SGA & MC (2%) | 10/1 | 0.15M phosphate, pH 7.94 | 30 |

(B)

| Components | MW | Mmoles | Wt (g) | Arm | mmoles | Arms Eq | Polymer % Solution (w/v) |
|---|---|---|---|---|---|---|---|
| 4ARM-20k-AA | 20000 | 1000 | 0.2 | 4 | 0.01 | 0.04 | |
| 8ARM-15k-SG | 15000 | 1000 | 0.075 | 8 | 0.01 | 0.04 | |
| Buffer Volume (phosphate) | | | 1.4 | | | | 19.6 |
| 4ARM-5k-NH2 | 5000 | 1000 | 0.27 | 4 | 0.05 | 0.22 | |
| 4ARM-10k-SG | 10000 | 1000 | 0.12 | 4 | 0.01 | 0.05 | |
| Buffer Volume (phosphate) | | | 1 | | | | 39.0 |
| 4ARM-5k-NH2 | 5000 | 1000 | 0.17 | 4 | 0.03 | 0.14 | |

TABLE 10-continued (A) Summary of the reaction details for several representative thin film formulations; (B) more detailed tabulation of a selection of the reaction details including moles (films ranged in thickness from 100 to 500 μm).

| 4ARM-10k-SG | 10000 | 1000 | 0.34 | 4 | 0.03 | 0.14 | |
| Buffer Volume (phosphate) | | | 1.4 | | | | 36.4 |
| 4ARM-5k-NH2 | 5000 | 1000 | 0.27 | 4 | 0.05 | 0.22 | |
| 4ARM-10k-SG | 10000 | 1000 | 0.12 | 4 | 0.01 | 0.05 | |
| Buffer Volume (phosphate) | | | 1 | | | | 39.0 |
| Viscosity Enhancer | | | 1.25% HPMC | | | | |

Example 13

Preparation of Kits and their Use

Several kits were prepared with polymer formulation tested earlier. The materials used to assemble the kits are listed in Table 11 and the formulations used are listed in Table 12. The kits are typically composed of two syringes, one syringe containing the solid components and the other syringe containing the liquid buffer. The syringes are connected via a mixing tube and a one-way valve. The contents of the syringes are mixed via opening the valve and transferring the contents of one syringe into the other, repeatedly, for 10 to 20 seconds. The spent syringe and mixing tube are then removed and discarded, and the active syringe is fitted with a dispensing unit, such as a needle or cannula, and the polymer solution is expelled until the onset of gelation. In other embodiments, the viscous solution impedes the dissolution of the solid components and thus a third syringe is employed. The third syringe contains a concentrated viscous buffer that enhances the viscosity of the solution once all the components have dissolved. In some embodiments, the optical clarity of the resulting polymer is improved through the addition of a syringe filter.

All of the formulations tested were easily dispensed through a 22 gauge needle. The mixing action between the two syringes was turbulent and the introduction of a significant amount of air bubbles was apparent. Gentle mixing results in a clear material free of bubbles. Alternatively, the use of a syringe filter was found to remove bubbles without any change in the polymer properties.

TABLE 11

Materials used to fabricate kits including vendor, part number and lot number.

| Description | Vendor |
|---|---|
| Vincon Tubing, 1/8" I.D. 1/4" O.D. 1/16" wall, 100 Ft. | Ryan Herco Flow Solutions |
| 12 mL Luer-Lok Syringe | Tyco Healthcare, Kendall Monoject ™ |
| 3 mL Luer-Lok Syringe | Tyco Healthcare, Kendall Monoject ™ |
| One Way Stopcock, Female Luer Lock to Male Luer | QOSINA |
| Female Luer Lock Barb for 1/8" I.D. tubing, RSPC | QOSINA |
| Non-vented Luer Dispenser Tip Cap, White | QOSINA |
| 32 mm Hydrophilic Syringe Filter, 5 micron | PALL ® Life Sciences |

TABLE 12

The detailed contents for four different kits; the solid components are in one syringe, while the liquid components are in another syringe; a mixing tube connects the two syringes.

| Components | MW | wt (g) | Arm | mmoles | Arms Eq | % Solution |
|---|---|---|---|---|---|---|
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate buffer | | | 2.5 mL 0.10M, pH 7.80 | | | 4.8 |
| Viscosity Enhancer | | | No viscosity enhancer | | | |
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate buffer | | | 2.5 mL 0.10M, pH 7.80 | | | 4.8 |
| Viscosity Enhancer | | | 0.3% HPMC | | | |
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate buffer | | | 2.5 mL 0.10M, pH 7.80 | | | 4.8 |
| Viscosity Enhancer | | | 7.5% Povidone | | | |
| 8ARM-20k-NH2 | 20000 | 0.04 | 8 | 0.002 | 0.016 | |
| 4ARM-20k-SGA | 20000 | 0.08 | 4 | 0.004 | 0.016 | |
| Phosphate buffer | | | 2.5 mL 0.10M, pH 7.80 | | | 4.8 |
| Viscosity Enhancer | | | 1.0% HPMC | | | |

Several additional kits were prepared with the polymer formulation that performed the best in initial trials. The materials used to assemble the kits are listed in Table 13. The kits are typically composed of two syringes, one syringe containing the solid components and the other syringe containing the liquid buffer. The syringes were loaded by removing the plungers, adding the components, purging the syringe with a gentle flow of nitrogen gas for 20 seconds, and then replacing the plunger. Finally, the plungers were depressed as much as possible to reduce the internal volume of the syringes. The specifications for the amounts of chemical components in the kits are listed in Table 14A. A summary describing the lots of kits prepared is listed in Table 14B.

The syringes were connected directly after uncapping, the male part locking into the female part. The contents of the syringes were mixed via transferring the contents of one syringe into the other, repeatedly, for 10 to 20 seconds. The spent syringe was then removed and discarded, and the active syringe was fitted with a dispensing unit, such as a needle or cannula, and the polymer solution was expelled until the onset of gelation. In other embodiments, the viscous solution impeded the dissolution of the solid components and thus a third syringe was employed. The third syringe contained a concentrated viscous buffer that enhanced the viscosity of the solution once all the components had dissolved.

All the formulations tested were easily dispensed through a 22 gauge needle. The mixing action between the two syringes was turbulent and the introduction of a significant amount of air bubbles was apparent. The use of a syringe filter was found to remove bubbles without any change in the polymer properties.

The prepared kits were placed into foil pouches along with one oxygen absorbing packet per pouch. The pouches were heat sealed with a CHTC-280 PROMAX tabletop chamber sealing unit. Two different modes of sealing were explored: under nitrogen and under vacuum. The settings for sealing under nitrogen were: 30 seconds of vacuum, 20 seconds of nitrogen, 1.5 seconds of heat sealing, and 3.0 seconds of cooling. The settings for sealing under vacuum were: 60 seconds of vacuum, 0 seconds of nitrogen, 1.5 seconds of heat sealing, and 3.0 seconds of cooling.

TABLE 13

Materials used to fabricate kits including vendor, part number and lot number.

| Description | Vendor |
| --- | --- |
| 12 mL Male Luer-Lok Syringe | Tyco Healthcare, Kendall Monoject ™ |
| 5 mL Female Luer Lock Syringe, Purple | QOSINA |
| Male Luer Lock Cap, Non-vented | QOSINA |
| Female Non-vented Luer Dispensor Tip Cap, White | QOSINA |
| 100 cc oxygen absorbing packet | IMPAK |
| 6.25" × 9" OD PAKVF4 Mylar foil pouch | IMPAK |

TABLE 14

Specifications for kit components for the 8ARM-20k-AA/8ARM-20-NH2 & 4ARM-20k-SGA formulation with 60, 65, 70 and 75% degradable amine (A). LOT formulation summary (B).

(A)

| Components | Specifications | | | |
| --- | --- | --- | --- | --- |
| | 60/40 | 65/35 | 70/30 | 75/25 |
| 8ARM-20k-AA | 0.024-0.026 g | 0.026-0.027 g | 0.028-0.029 g | 0.030-0.031 g |
| 8ARM-20k-NH2 | 0.014-0.016 g | 0.013-0.014 g | 0.011-0.012 g | 0.009-0.010 g |
| 4ARM-20k-SGA | 0.080-0.082 g | 0.080-0.082 g | 0.080-0.082 g | 0.080-0.082 g |
| Phosphate Buffer | 2.50 mL of 0.10M phosphate, pH 7.58, 0.30% HPMC (8.48 cSt ± 0.06 @ 20° C.) | | | |

(B)

| Formulation | Buffer pH | Sealing Method | Notes |
| --- | --- | --- | --- |
| 60/40 | 7.46 | nitrogen | |
| 60/40 | 7.58 | nitrogen | |
| 60/40 | 7.72 | nitrogen | |
| 70/30 | 7.58 | vacuum | |
| 70/30 | 7.58 | vacuum | no nitrogen purging of syringe |
| 65/35 | 7.58 | vacuum | |
| 75/25 | 7.58 | vacuum | |
| 75/25 | 7.58 | vacuum | |
| 75/25 | 7.58 | nitrogen | |
| 65/35 | 7.58 | vacuum | |
| 65/35 | 7.58 | nitrogen | |

Several kits were prepared for use in beta testing. The materials used to assemble the kits are listed in Table 15. The kits are typically composed of two syringes, one syringe containing the solid components and the other syringe containing the liquid buffer. The syringes were loaded by removing the plungers, adding the components, purging the syringe with a gentle flow of inert gas for 10 seconds, and then replacing the plunger. Finally, the plungers were depressed as much as possible to reduce the internal volume of the syringes.

Alternatively, a single syringe kit may be prepared by loading the solid components into one female syringe along with a solid form of the phosphate buffer. The kit is then utilized in a similar fashion as the dual syringe kit, except the user may use a specified amount of a variety of liquids in a male syringe. Typically, any substance provided in a liquid solution for injection may be used. Some examples of suitable liquids are water, saline, Kenalog-10, Depo-Medrol and Nolvasan.

The kits are utilized in the following fashion. The syringes are connected directly after uncapping, the male part locking into the female part. The contents of the syringes are mixed via transferring the contents of one syringe into the other, repeatedly, for 10 to 20 seconds. The spent syringe is then removed and discarded, and the active syringe is fitted with a dispensing unit, such as a needle, a spray nozzle or a brush tip, and the polymer solution is expelled until the onset of gelation.

The prepared kits were placed into foil pouches along with one oxygen absorbing packet and one indicating silica gel packet per pouch. Labels were affixed to the pouches that displayed the product and company name, contact information, LOT and batch numbers, expiration date, and recommended storage conditions. A radiation sterilization indicator that changes color from yellow to red upon exposure to sterilizing radiation was also affixed to the upper left corner of the pouch. The pouches were heat sealed with a CHTC-280 PRO-MAX tabletop chamber sealing unit. The settings for sealing under vacuum were: 50 seconds of vacuum, 1.5 seconds of heat sealing, and 5.0 seconds of cooling.

An example detailing the lots of sterile kits prepared is listed in Table 16. A previous study found that if the loaded syringe was not purged with nitrogen before replacing the plunger during kit preparation, the sterile kits exhibited an increase in gel time of about 30 seconds relative to kits that had syringes flushed with nitrogen. No significant difference was found between kits that had been sealed under vacuum and kits that had been sealed under nitrogen. It was easily observable when the vacuum-sealed kits lost their seal, so it was decided to vacuum-seal all kits as standard procedure. The effects of including the oxygen absorbing packet and silica gel packet to the kits on the long term storage stability is currently under investigation.

TABLE 15

Materials used to fabricate kits including vendor, and part number.

| Description | Vendor | Part # |
| --- | --- | --- |
| 10 mL Luer-Lok Syringe | BD | 309604 |
| Non-Vented Luer Dispenser Tip Cap, White | QOSINA | 65119 |
| 5 mL Female Luer-Lock Syringe, Purple PP | QOSINA | C3610 |
| Male Luer Lock Cap, Non-Vented, PP | QOSINA | 11166 |
| Brush tip | Flumatic | BT01225R |
| 5.25" × 8" PAKVF4D Mylar foil pouch | IMPAK | 0525MFDFZ08TE |
| 3.5" × 6.5" PAKVF4W Mylar foil pouch | IMPAK | 035MFW065Z |
| Radiation Sterilization Indicator | QOSINA | 13124 |
| 100 cc oxygen absorbing packet | IMPAK | OAP100 |
| Indicating silica gel | IMPAK | 40ISG37 |

TABLE 16

Example specifications for kit components for the 8-arm-AA-20K/8-arm-NH2-20K & 4-arm-SGA-20K formulation with 75% degradable amine (A). LOT formulation summary (B).

(A)

| Components | LOT # & Specifications |
| --- | --- |
| 8ARM-20k-AA | 0.029-0.031 g |
| 8ARM-20k-NH2 | 0.009-0.011 g |
| 4ARM-20k-SGA | 0.079-0.081 g |
| Phosphate Buffer | 2.50 mL of 0.10 M phosphate, pH 7.58, 0.30% HPMC (8.48 cSt ± 0.06 @ 20° C.) |

TABLE 16-continued

Example specifications for kit components for the 8-arm-AA-20K/8-arm-NH2-20K & 4-arm-SGA-20K formulation with 75% degradable amine (A). LOT formulation summary (B).

| LOT Size | 3 | 30 | 34 | 48 |
| --- | --- | --- | --- | --- |
| Gel Time (s) | | | 110-125 | |
| Degradation Time (days) | | | 10-12 | |

(B)

| Components | LOT # & Specifications |
| --- | --- |
| 8ARM-20k-AA | 0.029-0.031 g |
| 8ARM-20k-NH2 | 0.009-0.011 g |
| 4ARM-20k-SGA | 0.079-0.081 g |
| Phosphate Buffer Powder | 0.03-0.06 g |
| Nolvasan (2% chlorhexidine) | 2.50 mL, 1% denatonium benzoate |

| LOT Size | 64 |
| --- | --- |
| Gel Time (s) | 150 |
| Degradation Time (days) | 11 |

The kit preparation time was recorded. Loading one buffer syringe took an average of 1.5 minutes, while one solids syringe took an average of 4 minutes. Vacuum sealing one kit took approximately 1.5 minutes. Thus, the time estimate for the preparation of one kit was 7 minutes, or approximately 8 kits per hour. The kit preparation time may be improved by premixing all the solids in the correct ratios such that only one mass of solids needs to be measured, and by optimizing the vacuum sealing procedure by reducing the vacuum cycle time.

All the formulations tested were easily dispensed through a 23 to 34 gauge needle. Higher gauges exhibit a lower flow rate as expected. The mixing action between the two syringes was turbulent and the introduction of a significant amount of air bubbles was apparent. The use of a syringe filter was found to remove bubbles without any change in the polymer properties.

Figure 19A:
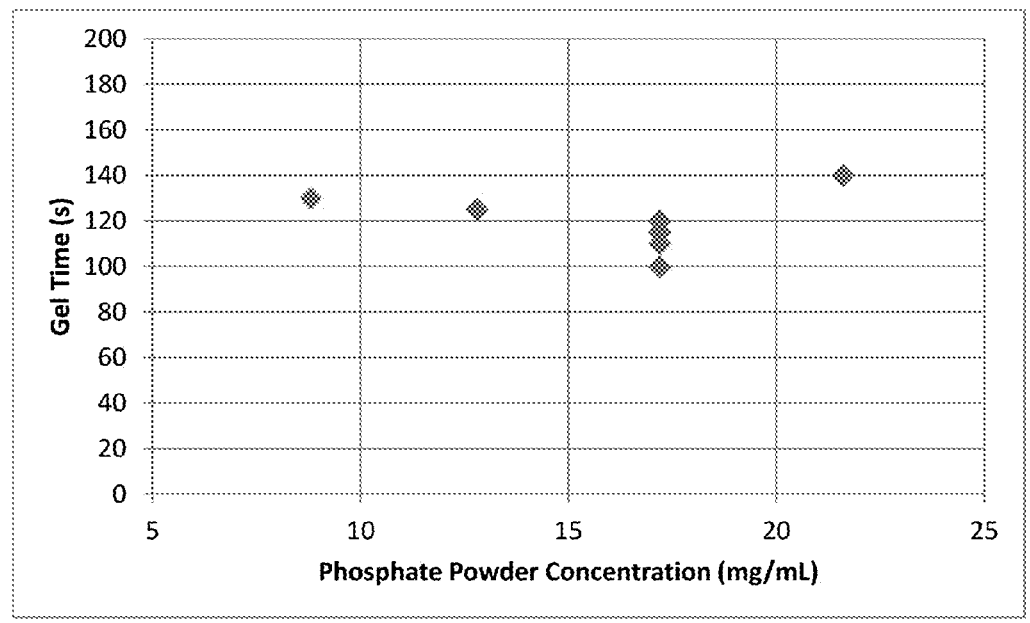
FIGS. 19A-19B shows the effect of solid phosphate powder concentration on polymer gel time (19A) and solution pH (19B).
Figure 19B:
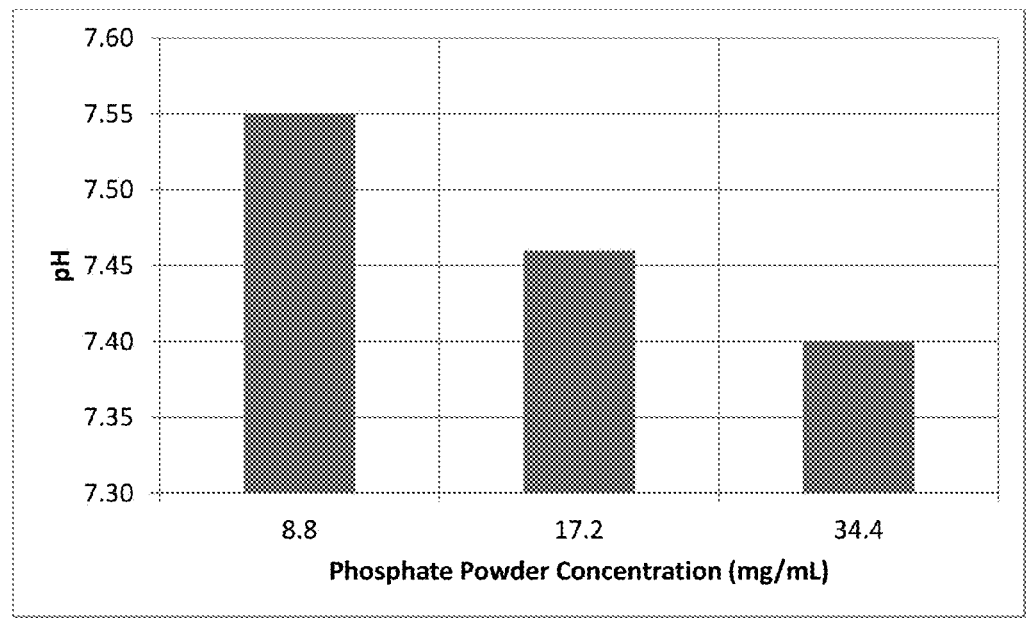

For the single syringe system, the effect of phosphate powder use was investigated. FIG. 19A-19B shows the effect of varying amounts or concentrations of the solid phosphate on polymer gel times and solution pH. The system was found to be relatively insensitive to the amount of phosphate, tolerating up to 2-fold differences without significant variation.

Kit Sterilization & Testing

The sealed kits were packed into large sized FedEx boxes. Each box was sterilized via electron-beam radiation at NUTEK Corporation according to a standard procedure that was developed. Included in this report is a copy of the standard sterilization procedure document.

For each lot of sterilized kits, a gel time and degradation time test was performed on a randomly selected kit to verify the viability of the materials. A previous study included a runner or control box of kits that was not sterilized, and concluded that environmental conditions during transit of the kits did not play a significant role in gel time changes.

Sterilized kits were sent to NAMSA for sterility verification according to USP<71>. The kits were verified as sterile.

Figure 20A:
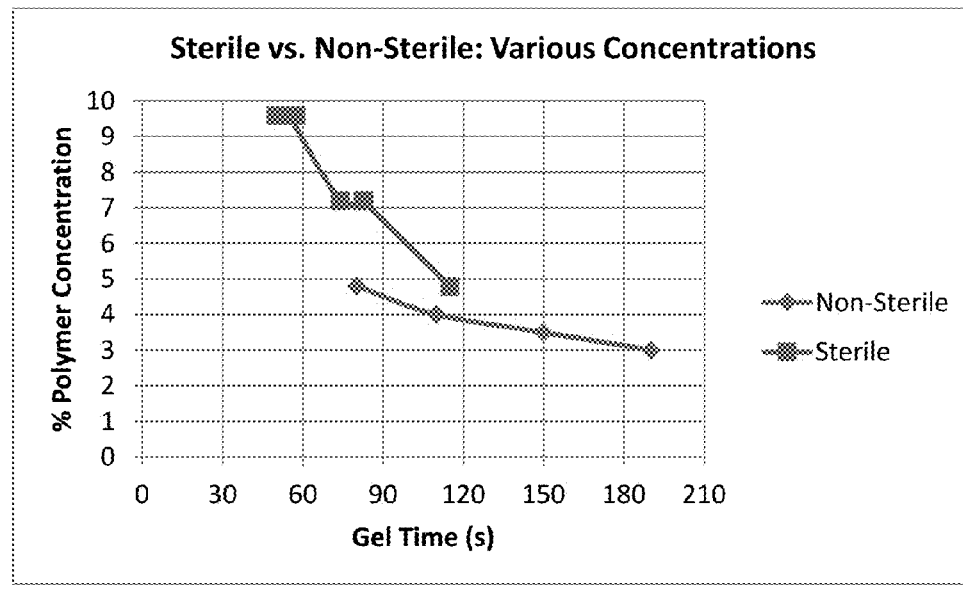
FIGS. 20A-20B shows the effect of sterilization on gel times for polymers of various concentrations (20A) and (20B). For example, a sterile 6 to 7% polymer behaves similarly to a non-sterile 4 to 5% polymer.
Figure 20B:
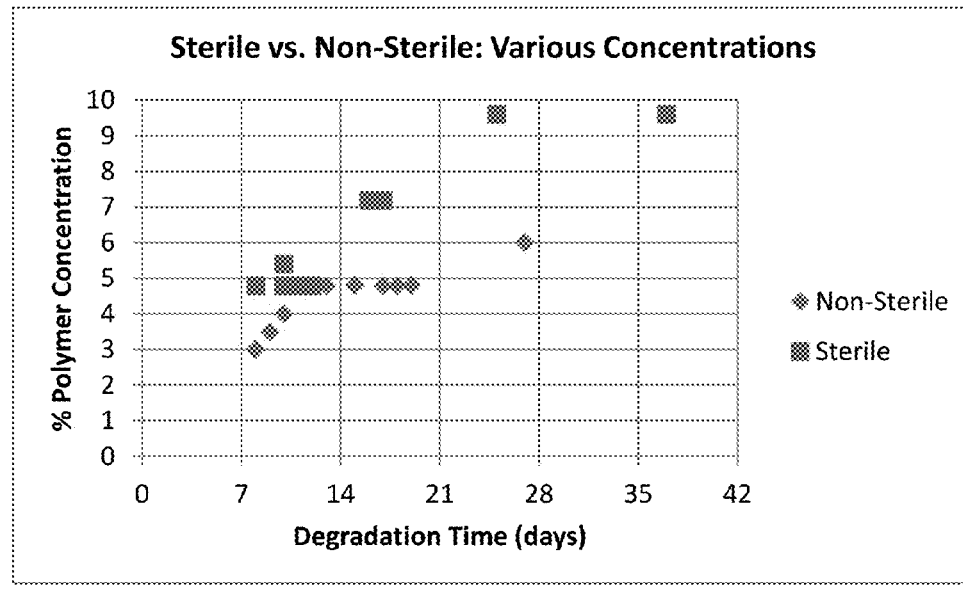

No physical changes in the monomer and phosphate buffer solutions were observed post-sterilization. Prior experiments have shown that the polymer gel times consistently increase by approximately 30 seconds after sterilization. For example, a polymer with a 90 second gel time will exhibit a 120 second gel time after sterilization. The pH of the sterile buffer was unchanged, so it was suspected that some monomer degradation during sterilization occurred. This was confirmed by preparing unsterilized polymers at various concentrations and comparing the gel times, degradation times and mechanical properties with sterilized polymers (FIG. 20A-20B). The current data shows that the monomers experience roughly 15 to 20% degradation upon sterilization. Thus, a 5% polymer after sterilization will behave similarly to a 4% polymer. Additional experiments are planned to establish a detailed quality control calibration curve.

Storage Stability

The sterilized kits were stored at 5° C. Some kits were stored at 20° C. or 37° C. to explore the effect of temperature on storage stability. The stability of the kits was primarily quantified by recording changes in gel time, which is directly proportional to the extent of monomer degradation. The 37° C. temperature was maintained by submerging the kits fully into the water bath and thus represents the worst case scenario regarding humidity.

Figure 21:
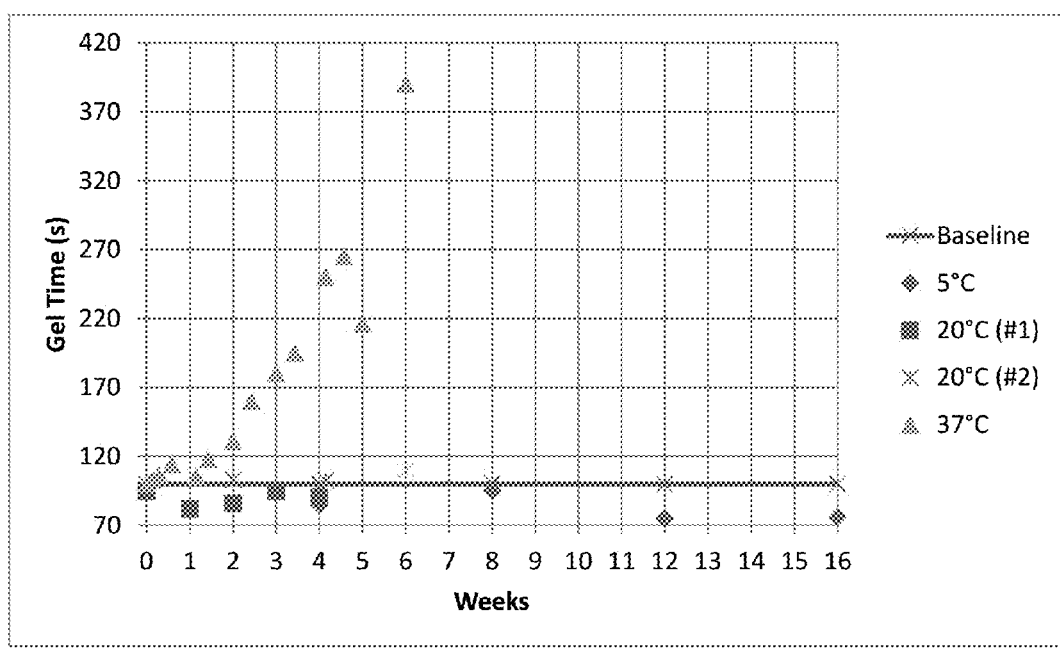
FIG. 21 shows the storage stability of kits at 5° C., 20° C. and 37° C.

The storage stability of the kits was explored by placing some kits at 5° C., 20° C. or 37° C. and measuring the change in gel times at defined intervals. The kits were prepared and sealed according to the procedures detailed in a previous section. The results are shown in FIG. 21. Over 16 weeks, no significant change in gel times were observed for kits stored at 5° C. and 20° C. At 37° C., the gel time begins to increase after roughly 1 week at a constant rate. The foil pouch proved to be an effective moisture barrier. The indicating silica gel packet exhibited only mild signs of moisture absorption as evidenced by the color. Longer term data is still in the process of being collected.

Example 13A

Example of Syringe Kit Preparation

One syringe kit was developed where the components are stored in two syringes, a male and a female syringe. The female syringe contains a mixture of white powders. The male syringe contains a buffer solution. The two syringes are connected and the contents mixed to produce a liquid polymer. The liquid polymer is then sprayed or applied over the suture wound where it covers the entire suture line. During the process, the polymer enters the voids left by sutures and protects the wound from infections. At the wound site, the liquid polymer turns into a solid gel and stays at the site for over two weeks. During this time, the wound is healed and infection free.

The components necessary to prepare the kit are disclosed in Table 17 and Table 18. To prepare the powder components of the kit to fill into the female syringe, the plunger of the 5 mL female Luer-lock syringe was removed, and the syringe was capped with the appropriate cap. 8ARM-20k-AA (0.028 g, the acceptable weight range is 0.0270 g to 0.0300 g), 8ARM-20k-NH2 (0.012 g, the acceptable weight range is 0.0100 g to 0.0130 g), 4ARM-20k-SGA (0.080 g, the acceptable weight range is 0.0790 g to 0.0820 g), and 0.043 g of freeze-dried phosphate buffer powder (0.043 g, the acceptable weight range is 0.035 g to 0.052 g) were each carefully weighed out and poured into the syringe. The syringe was then flushed nitrogen/argon gas for about 10 seconds at a rate of 5 to 10 L/min and the plunger was replaced to seal the contents. The syringe was then flipped so that the cap was facing towards the ceiling. The syringe cap was then loosened and the air space in the syringe was minimized by expelling as much air as possible from the syringe. Typical compressed powder volume is 0.2 mL. Then, the syringe cap was tighten until the cap was finger tight.

The liquid component was prepared on a 500 mL batch size, wherein 50 mL of commercial 2% chlohexidine solution, 450 mL of distilled water, and 1.5 g of HPMC were poured in to sterile container. The sterile container was then capped and shook vigorously for 10 seconds. The solution was allowed to stand under ambient conditions for 16 hours, thereby allowing for the foam to dissipate and any remaining HPMC to dissolve.

The liquid/buffer syringe was prepared by removing the plunger of the male Luer-lock syringe followed by capping the syringe with the appropriate cap. 2.50 mL of the buffer/liquid solution was transferred by pipette into the syringe. Mixing the liquid and solid components together will afford a 0.1 M phosphate buffer solution at pH 7.4. The syringe was then flushed with nitrogen/argon gas for about 5 seconds at a rate of 5 to 10 L/min. The plunger of the syringe was then replaced to seal the contents. Then the syringe was flipped so that the cap was facing towards the ceiling and the syringe cap was loosen and air space was minimized by expelling as much air as possible from the syringe. Then the syringe cap was tightened until the cap was finger tight. A configuration of this kit embodiment is shown in Table 19 (Configuration 1).

Alternately, another embodiment of the kit is where the solid components are 8-ARM-20k-AA (0.028 g), 8-ARM-20k-NH2 (0.012 g), and 4 ARM-20k-SGA (0.080 g) (Configuration 2, Table 20). The liquid component is comprised of 2.50 mL of 0.1 M phosphate buffer with 0.3% HPMC. In a further embodiment of the kit, the solid components are comprised of 8-ARM-20k-AA (0.0112 g), 8-ARM-20k-NH2 (0.0056 g), 4 ARM-20k-SGA (0.032 g), and phosphate solid buffer/HPMC powder (0.017 g) (Configuration 3, Table 21). For this formulation, 1.0 mL of liquid is used, wherein the liquid component can be saline, DI water, or therapeutic agent.

TABLE 17

Components used to fabricate the solid componentsfor the female syringe

| Components | Technical Name |
|---|---|
| 8ARM-20k-AA | 8ARM PEG Acetate amine, HCl salt, MW 20k |
| 8ARM-20k-NH2 | 8ARM PEG amine (hexaglycerol), HCl salt, MW 20k |
| 4ARM-20k-SGA | 4-arm PEG succinimidyl glutaramide (pentaerythritol), MW 20k |
| | Commercial 2% chlorhexidine solution |
| | Freeze-dried phosphate buffer powder |

TABLE 18

Materials used to fabricate kit including vendor, part number and lot number.

| Description | Vendor | Part # | Vendor Catalog # |
|---|---|---|---|
| 10 mL Luer-Lok Syringe | BD | CM-0003 | 309604 |
| Non-Vented Luer Dispenser Tip Cap, White | QOSINA | CM-0004 | 65119 |
| 5 mL Female Luer-Lock Syringe, Purple PP | QOSINA | CM-0005 | C3610 |
| Male Luer Lock Cap, Non-Vented, PP | QOSINA | CM-0006 | 11166 |

TABLE 19

Exemplary Kit Configuration 1.

| | Kit Configuration 1 | | |
| --- | --- | --- | --- |
| Components | Syringe 1 (solids) 5cc Female | Syringe 2 (Liquid) 5cc Male | Brush Holder |
| 8-ARM-20k-AA (Powder) | 0.028 g | | |
| 8-ARM-20k-NH2 (Powder) | 0.012 g | | |
| 4-ARM-20k-SGA (Powder) | 0.080 g | | |
| Phosphate Buffer (Powder) | 0.043 g | | |
| Viscous Antiseptic Solution 0.3% HPMC (hyrdoxy propyl methyl cellulose) | | 2.50 mL | |
| Brush Tip | | | 1 Brush Tip |

TABLE 20

Exemplary Kit Configuration 2.

| | Kit Configuration 2 | | |
| --- | --- | --- | --- |
| Components | Syringe 1 (solids) 5cc Female | Syringe 2 (Liquid) 5cc Male | Brush Container |
| 8-ARM-20k-AA (Powder) | 0.028 g | | |
| 8-ARM-20k-NH2 (Powder) | 0.012 g | | |
| 4-ARM-20k-SGA (Powder) | 0.080 g | | |
| 0.1M Phosphate buffer with 0.3% HPMC (hyrdoxy propyl methyl cellulose) | | 2.50 mL | |
| Brush Tip | | | 1 Brush Tip |

TABLE 21

Exemplary Kit Configuration 3.

| | Kit Configuration 3 | | |
| --- | --- | --- | --- |
| Components | Syringe 1 (solids) 5cc Female | Syringe 2 (empty) 5 cc Male | Brush Container |
| 8-ARM-20k-AA | 0.0112 g | | |
| 8-ARM-20k-NH2 | 0.0056 g | | |
| 4-ARM-20k-SGA | 0.032 g | | |
| Phosphate Buffer/ HPMC Powder | 0.017 g | | |
| Brush Tip | | | 1 Brush Tip |

Example 13B

Example of Syringe Kit Preparation

Another syringe kit was developed where the solid components, a mixture of white powders, are stored in one female syringe. A standard male syringe is used to take up the drug solution, such as one containing Kenalog. The two syringes are connected and the contents mixed to produce a liquid polymer. The liquid polymer is then delivered to the target site.

The components necessary to prepare the kit are disclosed in Table 17 and Table 18. To prepare the powder components of the kit to fill into the female syringe, the plunger of the 5 mL female Luer-lock syringe was removed, and the syringe was capped with the appropriate cap. 8ARM-20k-AA (0.0125 g, the acceptable weight range is 0.012 g to 0.013 g), 8ARM-20k-NH2 (0.075 g, the acceptable weight range is 0.007 g to 0.008 g), 4ARM-20k-SGA (0.040 g, the acceptable weight range is 0.040 g to 0.042 g), and 0.018 g of freeze-dried phosphate buffer powder (0.043 g, the acceptable weight range is 0.017 g to 0.022 g) were each carefully weighed out and poured into the syringe. The syringe was then flushed nitrogen/argon gas for about 10 seconds at a rate of 5 to 10 L/min and the plunger was replaced to seal the contents. The syringe was then flipped so that the cap was facing towards the ceiling. The syringe cap was then loosened and the air space in the syringe was minimized by expelling as much air as possible from the syringe. Then, the syringe cap was tightened until the cap was finger tight.

The liquid component for this embodiment is designed to be 1.0 mL of saline, DI water, or therapeutic agent, wherein mixing the contents of the two syringes together yields a 0.1 M phosphate buffer solution at a pH of 7.4.

Furthermore, the degradation time of the exemplified biocompatible hydrogel polymers can be controlled by adjusting the solution concentration, monomer type, and monomer amounts. 70% Acetate Amine has a degradation time of approximately 14 days while 62.5% Acetate Amine has a degradation time of approximately 180 days.

Example 14

Clinical Studies of Hydrogel Polymer on Wound Healing with Created Wounds

To test the effectiveness of the biocompatible hydrogel polymer of Example 13A to seal incisions post operatively and thereby decreasing the chances of post operative infections, a clinical study was performed under controlled settings wherein the horses used had incisions or lacerations that were specifically created in a clinical setting. One horse was used for experimental protocol and 9 clinical horses had created incisions or lacerations.

The experimental protocol horse was used to determine the safety and effectiveness of the biocompatible hydrogel polymer. A three year old, quarter horse, mare was used for the experimental protocol. Both sides of the neck were clipped and sterilely prepared. She was given 150 mg of xylazine for sedation. Twenty mls of lidocaine was used to locally to block the skin in 2 parallel lines (10 mls per site) on each side of the neck. Four incisions were made through the skin.

The two incisions on the right side were closed with staples and the cranial incision was sealed with the polymer. The two incisions on the left side were closed with 2-0 prolene in a cruciate pattern. The cranial incision was sealed with the polymer. The horse was monitored for the next 14 days. The incisions were inspected daily for any heat, pain, swelling or discharge. A 4 mm punch biopsy was taken at day 15 when the sutures and staples were removed.

The 9 other horses were clinical cases presented for surgical procedures or lacerations due to trauma. Three horses were presented for colic and the other six was seen for lacerations due to trauma. All of the clinical horses followed the same routine for post operative care. The colics were treated with antibiotics (3 days) and NSAID's (10 days). The lacerations were cleaned and the hair removed from the site. The site was cleaned as well as possible with saline and debridement. Local anesthetic was placed along the wound edges and the lacerations were closed with sutures and or staples. All six horses only received NSAID's for 5-7 days and no antibiotics.

There was no histological difference seen from the biopsies on the experimental horse between the covered sutured line and the uncovered sutured line. Thus, the hydrogel polymer was safe and effective for use in the horse. The clinical horses healed with a few complications. Two of the three colics experienced an increase in abdominal fluid formation or deposition, which is inevitable in certain colics. However, this problem can be addressed by strengthening the hydrogel polymer or applying a wider application of the polymer to cover the incision site. For the laceration horses, the hydrogel polymer sealed the lacerations with a 66.7% success rate initially without the use of systemic antibiotics. Two of the six laceration horses developed discharge, which was resolved with systemic antibiotics. With the use of antibiotics, there was a 100% recovery rate and the lacerations healed without complications. Thus, this clinical study demonstrates that the biocompatible hydrogel polymer is effective for use in wound healing in horses.

Example 15

Clinical Studies of Hydrogel Polymer for Wound Healing in Real Life Settings

Another clinical study to test of the effectiveness of the hydrogel polymer on wound healing was performed on larger sample size of 100 horses and wherein the horses had wounds that were not created in clinical setting (wounds received from real-life settings). The biocompatible hydrogel polymer was prepared as described in Example 13A from a mixture of 8ARM-20k-AA, 8-ARM-20k-NH2, and 4-ARM-20k-SGA and dissolved in phosphate buffered saline. Before the hydrogel polymer gelled, the polymer was applied over over the wound with a brush tip applicator. The hydrogel polymer gelled in about 90 seconds and covered the wound and wound edges.

On 54 horses, the biocompatible hydrogel polymer was applied over areas on the body that were sutured from laceration repairs, mass removals, and elective surgeries. No bandages were used on 19 of the 54 horses (35%) and bandages were used on the remaining 35 horses (65%). The bandages were used to prevent excessive swelling and were placed over the wound site. Of the 35 horses that received bandages, 30 received a primary bandage layer over the wound and the remaining 5 received a primary bandage layer on top of the hydrogel polymer.

29 horses had the hydrogel polymer of placed on ventral midline incisions (27 for colic surgeries, 1 for umbilical hernia repair, and 1 for bladder stone removal). The horses recovered in a 16'×16' recovery stall with head and tail ropes to assist in recovery. All of the incisions were examined daily for the next 14 days for any excessive heat, pain, swelling or discharge. Two horses had abdominal bandages placed during the recovery period. Only 24 were available for long term evaluation. Five of the horses were euthanized prior to discharge.

Nine horses had the hydrogel polymer of placed for primary wound care. Three of the wounds (33%) were in areas too difficult to bandage or in an area where bandages are not used. Six of the nine horses (67%) had wounds that were bandaged for compression. No primary bandage layer was used over the wound.

Eight horses had the hydrogel polymer placed in the inguinal area for cryptorchid surgery with scrotal ablation. None of these 8 horses were bandaged. The mild swelling associated with the procedure was managed with oral phenylbutazone at 2.2 mg/kg orally every 12 hours for 10 days. All the horses were placed on sulfamethoxazole/trimethoprin double strength (960 mg) dosed at 15 mg/kg orally given twice a day for only 5 days.

All the owners were contacted about 30 days after the surgery or injury to determine the satisfaction of the type of repair and any complications or comments associated with the hydrogel polymer.

Results

The largest group of 54 horses had the hydrogel polymer of cover surgically created or traumatically created wounds that were sutured. All the wounds healed without dehiscence or infection. For the horses with bandages, the hydrogel polymer did not interfere with the application or function of the bandages. The majority of clients in this group (48/54, 89%) were generally satisfied with the appearance of the healed wound and healing process. The remaining clients (6/54, 11%) were not completely satisfied with the results due to reasons that were not related to hydrogel polymer or hydrogel polymer performance.

In the group of 29 horses that had hydrogel polymer of cover ventral midline incisions, 24 horses were available for long term evaluation and 5 horses were euthanized for reasons not related to wound healing. All the owners were satisfied with the healing of the incisions. The majority of the wounds had no evidence of complications. However, one horse did develop slight drainage from the incision line, but this could be attributed to that fact that this horse had 18 feet of small intestine removed and a large amount of saline was placed into the abdominal cavity prior to closing the incision. For this one horse, the incision line did appear to be infected and dehiscence of the skin did occur. However, prior to placement of a new abdominal bandage, more hydrogel polymer was placed over the opened incision; and the horse healed without any other complications. For the five horses that did not survive to discharge, one horse immediately developed myopathy post operatively and was humanely euthanized. Three of the horses were euthanized due to continuous reflux for 5-7 days. The last horse was euthanized due to early signs of laminitis.

For the 9 horses that were treated with the hydrogel polymer for primary wound care, 6 horses had habronemiasis, one had a dehisced wound, and the other two had mass removals that could not be closed by primary closure. The 6 horses that were treated for habronemiasis had their wounds injected with triamcinolone, covered with the hydrogel polymer, and bandaged to add compression to the wound. The other three wounds were on the elbow (surgically removed shoe boil), and squamous cell carcinoma removal on the sheath and vaginal area. 5 of the 9 (56%) of the owners were satisfied with the results after a single injection of a corticosteroid, coverage with the hydrogel polymer followed by bandages. 4 of the 9 (44%) of the owners were not happy with the results of the steroid injection and the covering of the area. All four horses had the sites injected 3 more times every 2 weeks, and the last time a intralesional injection was done with the hydrogel polymer mixed with triamcinolone (20 mg) followed by coverage with the hydrogel polymer/triamcinolone mix. The 4 owners felt that the last injection with hydrogel polymer/triamcinolone mix helped the area heal better than just the steroid injections alone.

The 8 horses that had the scrotal ablation/cryptorchid surgery had no complications associated with the hydrogel polymer covering the incision lines. All the owners of the 8 horses were very satisfied with the results of the procedures, and no drainage or excessive pain was noticed by the owner or trainer.

DISCUSSION

In this clinical study, the hydrogel polymer was used on 100 horses to cover a wide variety of wounds in various locations and on wounds received from actual real-life settings. The hydrogel polymer was used on sutured, non-sutured, bandaged, and unbandaged wounds. The hydrogel polymer was easy to apply and appeared to provide protection to the site where applied. Furthermore, the hydrogel polymer did not interfere with bandaging of wounds, and in some instances, allowed for omission of the primary bandage layer. Furthermore, the hydrogel polymer did not appear to cause any wound irritation or delay in wound healing.

The overall response by the owners was very favorable. Out of the 94 horses used in the study, there were only 11 owners dissatisfied with the overall outcome of the procedure (8.73%), and none of the dissatisfaction was due to the use of hydrogel polymer. In fact, 6 of the complaints were related to the burden of bandaging, a problem that can be addressed by the hydrogel polymer. The results of this study highlight the utility of the hydrogel polymer in wound healing on horses in a variety of real-life settings and highlight the advantages of using the hydrogel polymer for wound healing. Applying the hydrogel polymer on the incision site may benefit horses to heal with and without a bandage. Previous studies have shown that the recovery room floor is a primary source of infection to a surgical site. The horse may recover better without the added irritation of a bandage or stent placed over the surgical site. The bandage can be placed after recovery to ensure good placement of the bandage if desired. Also, the hydrogel polymer can be used to cover sites that cannot be bandaged either due to location or type of wound.

Example 16

Pathology Studies of Hydrogel Polymer in Horses

To evaluate the biocompatibility and safety of the hydrogel polymer for use in horses, the local tissue response to hydrogel polymer was evaluated.

Ten adult quarter horses ranging from 3-19 years of age with a mean age of 11 years old were examined. The horses were not lame at a walk. Horses were fasted and injectable anesthesia (xylazine/ketamine/diazepam) was performed to allow easy placement of the hydrogel polymer of Example 13B. The hydrogel was placed into the following sites: intravitreal, intra-articular (tarsometatarsal joint), intramuscular, intra-bursal (navicular bursa), intra-peritoneal, intra,-pleural, and subcuetaneousely via aseptic techniques. The horses were examined daily for fever, lameness or any signs of discomfort. The horses were grouped into 5 groups of 2 horses. They were sacrificed at days 3, 5, 7, 14, and 21 days. A complete post mortem exam was performed along with histological examination of the tissues where the hydrogel polymer was injected.

All the carcasses were in good nutritional condition, well fleshed and with adequate fat reserves. Necropsy was performed and abnormalities were recorded. The histological examination of the tissues revealed that only minimal reactions were observed in tissues such as eyes, muscle, subcutaneous tissue and joints. Particularly, no gross abnormalities were found in the left tarso-metatarsal joint, left front navicular bursa in all of the horses examined. No lesions were found in the right eye or in the left subcutaneous sites in all of the horses examined. 70% of the horses had no lesions in the left eye and 50% of the horses had no lesions in the left intramuscular region. Furthermore, it is worth noting that all horses after the procedure had no problems standing after recovering from the procedure. Thus, these studies show that no detrimental inflammatory response was observed with the hydrogel polymer was injected into different areas of the horse body.

Example 17

Clinical Evaluation of Hydrogel Polymer for Treating Lameness in Horses

In this study, the effective of the hydrogel polymer as a drug delivery system was tested in 11 horses with palmar foot pain, which is a common cause of lameness in performance horses. The pain associated within the palmar aspect of the foot can be caused by pathologies of the bone and/or soft tissues located in the caudal heel of the horse. The response to medical treatment of caudal heel pain varies and the standard medical treatment for horses with caudal heel pain consist of the use of an oral non steroidal antinflammatory drugs, shoeing changes, stall rest, bisphosphonate (Tiludronate) or intrathecal injections of a corticosteroid with or without hyaluronic acid either into the distal interphalangeal joint or the navicular bursa. Injections into the navicular bursae can be technically difficult and may require radiographic equipment to ensure proper placement of the the needle in to the bursa. Due to the difficulties of the intra-bursal injections, studies have evaluated the concentrations of corticosteroid that will diffuse into the navicular bursa from the distal interphalangeal joint.

The use of intrathecal injections has been one of the primary ways to treat horses with caudal heel pain; however the products used within the space are limited to their pharmacokinetics. The purpose of this clinical study was to evaluate the effectiveness of the hydrogel polymer as drug delivery system for introducing triamcinalone acetonide into the navicular bursa of horses with caudal heel pain. Furthermore, the safety of the hydrogel polymer was also evaluated by noting any secondary complication associated with the use of a corticosteroid.

The hydrogel polymer used for this study is as described in Example 13B; wherein the hydrogel polymer was derived from a solid pre-formulation of 8ARM-20k-AA, 8-ARM-20k-NH2, and 4-ARM-20k-SGA and dissolved with 40 mg of triamcinalone acetonide (Kenalog 40). The hydrogel polymer was initially a liquid and then polymerized in 90 seconds after mixing and had a degradation time of two weeks.

Elevens horse were evaluated for lameness and it was confirmed that caudal heel pain was the only cause of lameness by a complete response to palmar digital nerve blocks. All horses had a prior diagnosis of navicular disease. All horses had to have little to no response to standard treatments prior to inclusion of the study. None of the horses involved in the study had a bilateral neurectomy or a single limb neurectomy. Eight quarter horses, two arabian, and one warm blood were involved with the clinical study.

Each horse was sedated with detomidine hydrochloride at 0.005 mg/kg iv and a abaxial sesamoid block using meperi- cane was performed either bilaterally or unilateral on the affected limb. The area at the caudal heel was aseptically prepared using chlorhexadine scrub and alcohol. A 22 ga 3.5 inch spinal needle was used to inject the hydrogel and steroid combination. The bursa was injected either standing on a 4 inch block or up in a podoblock. In the standing position the needle was placed about 0.5-1 cm proximal to the coronary band and advanced parallel to the ground until the navicular bone was contacted. In the non weight baring situation the needle was placed between the bulbs of the heel and directly perpendicular to the ground. Either technique was confirmed with radiographic conformation. Once the needle was in the bursa, the hydrogel polymer and steroid mixture was prepared and injected into the navicular bursa. A total volume of 1 ml was placed into the navicular bursa. After injection, the needle was removed and a small bandaged placed over the injection site for 20 minutes. All horse were discharged after injection and follow up calls were done daily for the first 3 days, then weekly for the first 8 weeks, and then every month until the horse started to show signs of lameness.

The results of the study were very promising. No complications were noted with the injection site, hydrogel polymer and/or with the corticosteroid. Furthermore, 91% of the horses responded positively to the treatment (10/11) and an average decrease in AAEP lameness scale by 90% was observed after 6 weeks. These results highlight the ability of the hydrogel polymer as a drug delivery system to deliver cortico steroids as the horses in this study did not respond to conventional treatments and improved to almost full resolution of lameness after treatment with the hydrogel polymer/corticosteroid.

What is claimed is:

1. A method of treating wounds of a mammal by delivering a solid polyglycol-based, fully synthetic, pre-formulation, comprising:
   (a) at least one solid first compound comprising more than two nucleophilic groups;
   (b) at least one solid second compound comprising more than two electrophilic groups;
   (c) optionally, a solid buffer component;
   (d) optionally, a solid therapeutic agent; and
   (e) optionally, a solid viscosity enhancer
   wherein the solid polyglycol-based, fully synthetic, pre-formulation polymerizes and/or gels at a target site of the wound to form a polyglycol-based, fully synthetic, biocompatible hydrogel polymer after addition of a liquid component, wherein the liquid component does not contain any first compound or second compound, and provided that the solid polyglycol-based, fully synthetic, pre-formulation does not contain any aqueous component.

2. The method of claim 1, wherein the mammal is a human or an animal.

3. The method of claim 1, wherein the liquid component comprises water, saline, a buffer, a therapeutic agent, or a combination thereof.

4. The method of claim 1, wherein the solid first compound is a MULTIARM (5k-50k) polyol derivative comprising polyglycol subunits and more than two nucleophilic groups, and wherein the solid second compound is a MULTIARM (5k-50k) polyol derivative comprising polyglycol subunits and more than two electrophilic groups.

5. The method of claim 4, wherein the solid first compound is a MULTIARM-(5-50k)-SH, a MULTIARM-(5-50k)-NH2, a MULTIARM-(5-50k)-AA, or a combination thereof, and the solid second compound is a MULTIARM-(5-50k)-SG, a MULTIARM-(5-50k)-SGA, a MULTIARM-(5-50k)-SS, or a combination thereof.

6. The method of claim 5, wherein the solid first compound is 4ARM-5k-SH, 4ARM-2k-NH2, 4ARM-5k-NH2, 8ARM-20k-NH2, 4ARM-20k-AA, 8ARM-20k-AA, or
   a combination thereof, and the solid second compound is 4ARM-10k-SG, 8ARM-15k-SG, 4ARM-20k-SGA, 4ARM-10k-SS, or a combination thereof.

7. The method of claim 6, wherein the solid first compound is 8ARM-20k-NH2 and/or 8ARM-20k-AA, and the solid second compound is 4ARM-20k-SGA.

8. A method of treating arthritis in a joint space in a mammal by delivering a solid polyglycol-based, fully synthetic, pre-formulation, comprising:
   (a) at least one solid first compound comprising more than two nucleophilic groups;
   (b) at least one solid second compound comprising more than two electrophilic groups;
   (c) optionally, a solid buffer component;
   (d) optionally, a solid therapeutic agent; and
   (e) optionally, a solid viscosity enhancer
   wherein the solid polyglycol-based, fully synthetic, pre-formulation polymerizes and/or gels at a target site in the joint space to form a polyglycol-based, fully synthetic, biocompatible hydrogel polymer after addition of a liquid component, wherein the liquid component does not contain any first compound or second compound, and provided that the solid polyglycol-based, fully synthetic, pre-formulation does not contain any aqueous component.

9. The method of claim 8, wherein the mammal is a human or an animal.

10. The method of claim 8, wherein the liquid component comprises water, saline, a buffer, a therapeutic agent or a combination thereof.

11. The method of claim 8, wherein the solid first compound is a MULTIARM (5k-50k) polyol derivative comprising polyglycol subunits and more than two nucleophilic groups, and wherein the solid second compound is a MULTIARM (5k-50k) polyol derivative comprising polyglycol subunits and more than two electrophilic groups.

12. The method of claim 11, wherein the solid first compound is a MULTIARM-(5-50k)-SH, a MULTIARM-(5-50k)-NH2, a MULTIARM-(5-50k)-AA, or a combination thereof, and the solid second compound is a MULTIARM-(5-50k)-SG, a MULTIARM-(5-50k)-SGA, a MULTIARM-(5-50k)-SS, or a combination thereof.

13. The method of claim 12, wherein the solid first compound is 4ARM-5k-SH, 4ARM-2k-NH2, 4ARM-5k-NH2, 8ARM-20k-NH2, 4ARM-20k-AA, 8ARM-20k-AA, or
   a combination thereof, and the solid second compound is 4ARM-10k-SG, 8ARM-15k-SG, 4ARM-20k-SGA, 4ARM-10k-SS, or a combination thereof.

14. The method of claim 13, wherein the solid first compound is 8ARM-20k-NH2 and/or 8ARM-20k-AA, and the solid second compound is 4ARM-20k-SGA.

15. A method of treating navicular disease in a hoof of a horse by delivering a solid polyglycol-based, fully synthetic, pre-formulation, comprising:
   (a) at least one solid first compound comprising more than two nucleophilic groups;
   (b) at least one solid second compound comprising more than two electrophilic groups;
   (c) optionally, a solid buffer component;
   (d) optionally, a solid therapeutic agent; and
   (e) optionally, a solid viscosity enhancer
   wherein the solid polyglycol-based, fully synthetic, pre-formulation polymerizes and/or gels at a target site in the hoof of the horse to form a polyglycol-based, fully synthetic, biocompatible hydrogel polymer after addition of a liquid component, wherein the liquid component does not contain any first compound or second compound, and provided that the solid polyglycol-based, fully synthetic, pre-formulation does not contain any aqueous component.

16. The method of claim 15, wherein the liquid component comprises water, saline, a buffer, a therapeutic agent or a combination thereof.

17. The method of claim 15, wherein the solid first compound is a MULTIARM (5k-50k) polyol derivative comprising polyglycol subunits and more than two nucleophilic groups, and wherein the solid second compound is a MULTIARM (5k-50k) polyol derivative comprising polyglycol subunits and more than two electrophilic groups.

18. The method of claim 17, wherein the solid first compound is a MULTIARM-(5-50k)-SH, a MULTIARM-(5-50k)-NH2, a MULTIARM-(5-50k)-AA, or a combination thereof, and the solid second compound is a MULTIARM-(5-50k)-SG, a MULTIARM-(5-50k)-SGA, a MULTIARM-(5-50k)-SS, or a combination thereof.

19. The method of claim 18, wherein the solid first compound is 4ARM-5k-SH, 4ARM-2k-NH2, 4ARM-5k-NH2, 8ARM-20k-NH2, 4ARM-20k-AA, 8ARM-20k-AA, or a combination thereof, and the solid second compound is 4ARM-10k-SG, 8ARM-15k-SG, 4ARM-20k-SGA, 4ARM-10k-SS, or a combination thereof.

20. The method of claim 19, wherein the solid first compound is 8ARM-20k-NH2 and/or 8ARM-20k-AA, and the solid second compound is 4ARM-20k-SGA.

* * * * *